United States Patent
Osaki et al.

(10) Patent No.: US 11,705,218 B2
(45) Date of Patent: Jul. 18, 2023

(54) NUCLEIC ACID ANALYSIS METHOD, NUCLEIC ACID ANALYSIS PROGRAM, AND DEVICE FOR LIBRARY PREPARATION

(71) Applicants: RICOH COMPANY, LTD., Tokyo (JP); FASMAC CO., LTD, Kanagawa (JP)

(72) Inventors: Yusuke Osaki, Kanagawa (JP); Hirotaka Unno, Kanagawa (JP); Yudai Kawashima, Kanagawa (JP); Michie Hashimoto, Tokyo (JP); Masayuki Yumoto, Kanagawa (JP); Satoshi Nakazawa, Kanagawa (JP); Yuki Yonekawa, Kanagawa (JP); Takahiro Matsudaira, Kanagawa (JP); Eri Nishiyama, Kanagawa (JP)

(73) Assignees: Ricoh Company, Ltd., Tokyo (JP); FASMAC CO., LTD., Kanagawa (JP)

( * ) Notice: Subject to any disclaimer, the term of this patent is extended or adjusted under 35 U.S.C. 154(b) by 658 days.

(21) Appl. No.: 16/718,390

(22) Filed: Dec. 18, 2019

(65) Prior Publication Data

US 2020/0194100 A1   Jun. 18, 2020

(30) Foreign Application Priority Data

Dec. 18, 2018 (JP) ................. 2018-236746
Jan. 31, 2019 (JP) ................. 2019-015126
Mar. 14, 2019 (JP) ................. 2019-046689
Mar. 15, 2019 (JP) ................. 2019-047881

(51) Int. Cl.
*G16B 35/10* (2019.01)
*G16B 30/00* (2019.01)
*C12Q 1/6874* (2018.01)

(52) U.S. Cl.
CPC ........... *G16B 35/10* (2019.02); *C12Q 1/6874* (2013.01); *G16B 30/00* (2019.02)

(58) Field of Classification Search
None
See application file for complete search history.

(56) References Cited

U.S. PATENT DOCUMENTS

| | | |
|---|---|---|
| 2003/0165832 A1 | 9/2003 | Sagner et al. |
| 2004/0153254 A1 | 8/2004 | Sagner et al. |
| 2010/0021923 A1 | 1/2010 | Sagner et al. |
| 2011/0118145 A1 | 5/2011 | Akmaev et al. |
| 2012/0270222 A1 | 10/2012 | Sagner et al. |
| 2016/0319339 A1 | 11/2016 | Akmaev et al. |
| 2016/0319345 A1 | 11/2016 | Gnerre et al. |
| 2017/0204406 A1 | 7/2017 | Kato et al. |
| 2018/0245131 A1 | 8/2018 | Meersseman et al. |
| 2019/0151843 A1 | 5/2019 | Kawashima et al. |

FOREIGN PATENT DOCUMENTS

| | | |
|---|---|---|
| EP | 1 138 783 A2 | 10/2001 |
| JP | 2015-204813 A | 11/2015 |
| JP | 6125731 B2 | 5/2017 |
| JP | 2018-093863 | 6/2018 |
| JP | 2018-514207 A | 6/2018 |
| JP | 2019-088268 A | 6/2019 |
| JP | 2019-092494 A | 6/2019 |
| JP | 2019-092495 A | 6/2019 |
| JP | 2019-092505 A | 6/2019 |
| JP | 2019-092506 A | 6/2019 |
| JP | 2019-092507 A | 6/2019 |
| JP | 2019-158647 A | 9/2019 |
| JP | 2019-162038 A | 9/2019 |
| WO | WO 2011/060240 A1 | 5/2011 |
| WO | WO2016/176091 A1 | 11/2016 |
| WO | WO2017/013102 A1 | 1/2017 |
| WO | WO 2018/081465 A1 | 5/2018 |
| WO | WO2019/093528 A1 | 5/2019 |
| WO | WO2019/093530 A1 | 5/2019 |
| WO | WO2019/103122 A1 | 5/2019 |
| WO | WO2019/103128 A1 | 5/2019 |

OTHER PUBLICATIONS

Ushio et al., "Quantitative monitoring of multispecies fish environmental DNA using high-throughput sequencing," Metabarcoding and Metagenomics 2018, 2:1-15, published Mar. 14, 2018. (Year: 2018).*
Tourlousse et al., "Synthetic spike-in standards for high-throughput 16S rRNA gene amplicon sequencing," Nucleic Acids Res. 2017, 45:e23. (Year: 2017).*
Extended European Search Report dated May 14, 2020 in Patent Application No. 19216648.6, citing documents AA-AG and AO-AS therein, 7 pages.
European Office Action dated Jan. 4, 2022 in European Application No. 19216648.6, 6 pages.
Moon et al., "Drop-on-Demand Single Cell Isolation and Total RNA Analysis", PLOS ONE, vol. 6, No. 3, Mar. 2011, pp. 1-10.
"Real-time PCR handbook", Life technologies, 2012, 70 pages.
Zhang et al., "Development of a facile droplet-based single-cell isolation platform for cultivation and genomic analysis in microorganisms", Scientific Reports, vol. 7, No. 1, Jan. 23, 2017, 11 pages.

(Continued)

*Primary Examiner* — Kaijiang Zhang
(74) *Attorney, Agent, or Firm* — Grüneberg and Myers PLLC

(57) ABSTRACT

In one embodiment, provided are a method for analyzing at least one nucleic acid that can conveniently and highly accurately analyze even a very small number of analyte at least one nucleic acid. In one embodiment, the present invention relates to a method for analyzing at least one nucleic acid, comprising: a library preparation step of preparing a library comprising at least one standard nucleic acid of specific copy number(s) and at least one analyte nucleic acid in a same system; a calibration curve data generation step of generating calibration curve data based on the copy number(s) of the at least one standard nucleic acid of specific copy number(s); and an analyte nucleic acid analysis step of identifying at least one nucleotide sequence of the analyte nucleic acid while identifying the number(s) of the at least one nucleotide sequence of the at least one analyte nucleic acid using the calibration curve data.

11 Claims, 37 Drawing Sheets

Specification includes a Sequence Listing.

(56) References Cited

OTHER PUBLICATIONS

Japanese Patent Application No. 2018-212607 filed Nov. 13, 2018 (Not yet published and corresponding to WO2019/093528 A1).
Japanese Patent Application No. 2018-213535 filed Nov. 14, 2018 (Not yet published and corresponding to U.S.2019/0151843 A1).
Japanese Patent Application No. 2018-216110 filed Nov. 19, 2018 (Not yet published and corresponding to WO2019/103128 A1).
Masayuki Ushio, et al, "Quantitative Monitoring of Multispecies Fish Environmental DNA using High-Throughput Sequencing" Metabarcoding & Metagenomics, vol. 2, 2018, pp. 1-15.
Japanese Office Action dated Aug. 9, 2022, in Japanese Application No. 2019-046689, with English translation, 7 pages.
Komkov A. et al., Poster No. P-08.02.5-008 "Next generation sequencing based approach for monitoring of minimal residual disease in acute lymphoblastic leukemia", The FEBS Journal, vol. 283, Suppl. 1, Sep. 2016, p. 376.

\* cited by examiner

Fig. 3

Well to be filled
with standard nucleic acid
and analyte nucleic acid

Well to be filled with sample

Fig. 4

Well to be filled with standard nucleic acid and analyte nucleic acid

Well to be filled with sample

| 1 | 1 | | | | | | |
|---|---|---|---|---|---|---|---|
| 3 | 3 | | | | | | |
| 5 | 5 | | | | | | |
| 7 | 7 | | | | | | |
| 9 | 9 | | | | | | |

$350_1$  $350_2$

```
SEQUENCE LISTING

<160> NUMBER OF SEQ ID NOS: 22

<210> SEQ ID NO 1
<211> LENGTH: 178
<212> TYPE: DNA
<213> ORGANISM: Artificial Sequence
<220> FEATURE:
<223> OTHER INFORMATION: synthetic nucleotide

<400> SEQUENCE: 1
gtcggtaaaa ctcgtgccag caactaaatc gtcttcggcg caagtcaccg cagtatcttc      60
gttggatctg tgggtaatac tcgtcataca gtccttgtta tgcggtctgg acccttgcca     120
cataaggatc ggctccgcat tgcaactgac tcaaactggg attagatacc ccactatg      178

<210> SEQ ID NO 2
<211> LENGTH: 178
<212> TYPE: DNA
<213> ORGANISM: Artificial Sequence
<220> FEATURE:
<223> OTHER INFORMATION: synthetic nucleotide

<400> SEQUENCE: 2
gtcggtaaaa ctcgtgccag ctacgtgaac cactctttct gtcctacata ggcactaagc      60
ctgtgtggag actctatgga gggcggtagc ggtctcatcc gtgctctggg actatccagt     120
agcttgcgca aagacgacct ttccttgctc tcaaactggg attagatacc ccactatg      178

<210> SEQ ID NO 3
<211> LENGTH: 178
<212> TYPE: DNA
```

<213> ORGANISM: Artificial Sequence
<220> FEATURE:
<223> OTHER INFORMATION: synthetic nucleotide

<400> SEQUENCE: 3

```
gtcggtaaaa ctcgtgccag caaacagact atcgatatga tctaagtaag agcctgaggt    60
gtttcgcgca acttcgcaga cgccttgcgc ggaaagttga tatacagcgt gtcgcaaacc   120
aaggacattt acacactgtc aggcgtcatt gcaaactggg attagatacc ccactatg    178
```

<210> SEQ ID NO 4
<211> LENGTH: 178
<212> TYPE: DNA
<213> ORGANISM: Artificial Sequence
<220> FEATURE:
<223> OTHER INFORMATION: synthetic nucleotide

<400> SEQUENCE: 4

```
gtcggtaaaa ctcgtgccag cgcggctgcg atgcaagcac agcgctcaag gggccattcc    60
aggtaatcgg cgaggaccag tccatccagc cattgagctg cctttatag acacaaacct   120
aggtacctag atagttgaat tcctcaaaac tcaaactggg attagatacc ccactatg    178
```

<210> SEQ ID NO 5
<211> LENGTH: 178
<212> TYPE: DNA
<213> ORGANISM: Artificial Sequence
<220> FEATURE:
<223> OTHER INFORMATION: synthetic nucleotide

<400> SEQUENCE: 5

```
gtcggtaaaa ctcgtgccag caacaatcgt ttcctttgtg caaagctaaa gaagccacca    60
cattctaccc tcccttattt tacagaacga gatttgatat aacattcgtt tcgagtaaaa   120
gtgaatgatg gaagccttgg tcggcgctga ccaaactggg attagatacc ccactatg    178
```

<210> SEQ ID NO 6
<211> LENGTH: 600
<212> TYPE: DNA
<213> ORGANISM: Artificial Sequence
<220> FEATURE:
<223> OTHER INFORMATION: synthetic nucleotide

<400> SEQUENCE: 6

```
attcgaaggg tgattggatc ggagatagga tgggtcaatc gtagggacaa tcgaagccag    60
aatgcaaggg tcaatggtac gcagaatgga tggcacttag ctagccagtt aggatccgac   120
tatccaagcg tgtatcgtac ggtgtatgct tcggagtaac gatcgcacta agcatggctc   180
aatcctaggc tgataggttc gcacatagca tgccacatac gatccgtgat tgctagcgtg   240
attcgtaccg agaactcacg ccttatgact gcccttatgt caccgcttat gtctcccgag   300
atcacacccg ttatctcagc cctaatctct gcggtttagt ctggccttaa tccatgcctc   360
atagctaccc tcataccatc gctcatacct tccgacattg catccgtcat tccaaccctg   420
attcctacgg tctaacctag cctctatcct acccagttag gttgcctctt agcatccctg   480
ttacgtacgc tcttaccatg cgtcttacct tggcactatc gatgggagta tggtagcgag   540
tatggaacgg actaacgtag gcagtaagct agggtgtaag gttgggacta aggatgccag   600
```

<210> SEQ ID NO 7
<211> LENGTH: 21
<212> TYPE: DNA
<213> ORGANISM: Artificial Sequence

```
<220> FEATURE:
<223> OTHER INFORMATION: synthetic nucleotide

<400> SEQUENCE: 7
gtcggtaaaa ctcgtgccag c                                          21

<210> SEQ ID NO 8
<211> LENGTH: 27
<212> TYPE: DNA
<213> ORGANISM: Artificial Sequence
<220> FEATURE:
<223> OTHER INFORMATION: synthetic primer

<400> SEQUENCE: 8
catagtgggg tatctaatcc cagtttg                                    27

<210> SEQ ID NO 9
<211> LENGTH: 54
<212> TYPE: DNA
<213> ORGANISM: Artificial Sequence
<220> FEATURE:
<223> OTHER INFORMATION: synthetic primer

<400> SEQUENCE: 9
acactctttc cctacacgac gctcttccga tctgctcaat cctaggctga tagg      54

<210> SEQ ID NO 10
<211> LENGTH: 54
<212> TYPE: DNA
<213> ORGANISM: Artificial Sequence
<220> FEATURE:
<223> OTHER INFORMATION: synthetic primer

<400> SEQUENCE: 10
gtgactggag ttcagacgtg tgctcttccg atctcgtaac agggatgcta agag      54

<210> SEQ ID NO 11
<211> LENGTH: 52
<212> TYPE: DNA
<213> ORGANISM: Artificial Sequence
<220> FEATURE:
<223> OTHER INFORMATION: synthetic primer

<400> SEQUENCE: 11
acactctttc cctacacgac gctcttccga tctgtgccag cmgccgcggt aa        52

<210> SEQ ID NO 12
<211> LENGTH: 54
<212> TYPE: DNA
<213> ORGANISM: Artificial Sequence
<220> FEATURE:
<223> OTHER INFORMATION: synthetic primer

<400> SEQUENCE: 12
gtgactggag ttcagacgtg tgctcttccg atctggacta chvgggtwtc taat      54

<210> SEQ ID NO 13
<211> LENGTH: 59
<212> TYPE: DNA
<213> ORGANISM: Artificial Sequence
<220> FEATURE:
<223> OTHER INFORMATION: synthetic primer

<400> SEQUENCE: 13
aatgatacgg cgaccaccga gatctacact cgactagaca ctctttccct acacgacgc 59
```

<210> SEQ ID NO 14
<211> LENGTH: 59
<212> TYPE: DNA
<213> ORGANISM: Artificial Sequence
<220> FEATURE:
<223> OTHER INFORMATION: synthetic primer

<400> SEQUENCE: 14
aatgatacgg cgaccaccga gatctacact tctagctaca ctctttccct acacgacgc          59

<210> SEQ ID NO 15
<211> LENGTH: 59
<212> TYPE: DNA
<213> ORGANISM: Artificial Sequence
<220> FEATURE:
<223> OTHER INFORMATION: synthetic primer

<400> SEQUENCE: 15
aatgatacgg cgaccaccga gatctacacc ctagagtaca ctctttccct acacgacgc          59

<210> SEQ ID NO 16
<211> LENGTH: 59
<212> TYPE: DNA
<213> ORGANISM: Artificial Sequence
<220> FEATURE:
<223> OTHER INFORMATION: synthetic primer

<400> SEQUENCE: 16
aatgatacgg cgaccaccga gatctacacg cgtaagaaca ctctttccct acacgacgc          59

<210> SEQ ID NO 17
<211> LENGTH: 59
<212> TYPE: DNA
<213> ORGANISM: Artificial Sequence
<220> FEATURE:
<223> OTHER INFORMATION: synthetic primer

<400> SEQUENCE: 17
aatgatacgg cgaccaccga gatctacacc tattaagaca ctctttccct acacgacgc          59

<210> SEQ ID NO 18
<211> LENGTH: 59
<212> TYPE: DNA
<213> ORGANISM: Artificial Sequence
<220> FEATURE:
<223> OTHER INFORMATION: synthetic primer

<400> SEQUENCE: 18
aatgatacgg cgaccaccga gatctacaca aggctataca ctctttccct acacgacgc          59

<210> SEQ ID NO 19
<211> LENGTH: 59
<212> TYPE: DNA
<213> ORGANISM: Artificial Sequence
<220> FEATURE:
<223> OTHER INFORMATION: synthetic primer

<400> SEQUENCE: 19
aatgatacgg cgaccaccga gatctacacg agccttaaca ctctttccct acacgacgc          59

<210> SEQ ID NO 20
<211> LENGTH: 59
<212> TYPE: DNA
<213> ORGANISM: Artificial Sequence
<220> FEATURE:
<223> OTHER INFORMATION: synthetic primer

```
<400> SEQUENCE: 20
aatgatacgg cgaccaccga gatctacact tatgcgaaca ctctttccct acacgacgc        59

<210> SEQ ID NO 21
<211> LENGTH: 54
<212> TYPE: DNA
<213> ORGANISM: Artificial Sequence
<220> FEATURE:
<223> OTHER INFORMATION: synthetic primer

<400> SEQUENCE: 21
caagcagaag acggcatacg agattcatga gcgtgactgg agttcagacg tgtg             54

<210> SEQ ID NO 22
<211> LENGTH: 54
<212> TYPE: DNA
<213> ORGANISM: Artificial Sequence
<220> FEATURE:
<223> OTHER INFORMATION: synthetic primer

<400> SEQUENCE: 22
caagcagaag acggcatacg agatcctgag atgtgactgg agttcagacg tgtg             54
```

NUCLEIC ACID ANALYSIS METHOD, NUCLEIC ACID ANALYSIS PROGRAM, AND DEVICE FOR LIBRARY PREPARATION

BACKGROUND OF THE INVENTION

Field of the Invention

In one embodiment, the present invention relates to a nucleic acid analysis method, a nucleic acid analysis program, and a device for library preparation.

In one embodiment, the present invention relates to a method for analyzing data of a high-throughput sequencing reaction, a kit for performing the method, and a program for allowing a computer to perform the method, etc.

Description of the Related Art

Next-generation sequencers (NGS) among DNA sequencing techniques are widely used in genetic testing etc., since a large number of nucleotide sequence data can be acquired from DNA extracted from specimens or samples. Particularly, research for detecting very small amounts of samples with high precision using a next-generation sequencer has flourished in recent years.

For example, an internal standard nucleic acid sample having a nucleotide sequence that is amplifiable with primers for amplifying microbial 16S rRNA gene, but is clearly distinguishable from the 16S rRNA gene has been proposed in order to accurately quantify the 16S rRNA gene (see, for example, Patent Document 1 (JP Patent Publication (Kokai) No. 2015-204813).

High-throughput sequencers such as next-generation sequencers (NGS) are techniques of sequencing a large number of DNA molecules in parallel, and widely used in genetic testing etc., since a large number nucleotide sequence data can be acquired from DNA extracted from specimens or samples. The data is managed in a unit called as "read". In the case of, for example, a sequencer from Illumina, Inc., 1 read corresponds to nucleotide sequence data obtained from 1 cluster of a flow cell. In a high-throughput sequencer, a nucleic acid molecule is amplified by PCR when preparing library. Therefore, the amplification product forms a plurality of clusters, and the same nucleotide sequence is obtained from the plurality of clusters. This is managed in a unit called "read number", and expressed as the phrase "sequence A has N reads" or "read number of sequence A is N", etc.

It is an challenge for analysis in the high-throughput sequencer to determine whether or not to use a sequence with a small read number in the analysis. The sequence with a small read number may be attributed to various error sources, for example, a sequence derived from an error resulting from sequencing, a sample-derived sequence contaminated after PCR, and a sample-derived sequence of the previous run remaining in a flow cell (in the case of a high-throughput sequencer having reusable flow cells). There has been no clear criterion so far to judge which read number suggests that the sequence thereof can be worth using in analysis. Methods for removing data based on a threshold determined using software such as cicleanseqv or Vsearch have been known in order to select sequences to be analyzed.

Patent Document 2 (JP Patent Publication (Kohyo) No. 2018-514207) discloses a method for determining a nucleic acid fragment sequence of a sample using a unique molecular identifier (UMI), with the aim of developing a method for determining a sequence of a DNA molecule in a small amount and/or with low allele frequency while suppressing the imprecision of sequencing caused by various error sources.

SUMMARY OF THE INVENTION

In one embodiment, it is an object of the present invention to provide a nucleic acid analysis method that can conveniently and highly accurately analyze even a very small number of analyte nucleic acids.

The conventional methods for removing data based on a threshold determined using software merely predict the threshold on output data, and trim reads based on this threshold. Thus, these methods cannot split the output data according to a clear criterion, since it is unclear whether the value of the read number serving as the threshold is suitable.

The invention described in Patent Document 2 is directed to suppressing the imprecision of sequencing caused by errors in sequencing reaction only, and cannot cover all reasons why a sequence not worth analyzing arises. Thus, the invention cannot solve the problem that the threshold for removing the sequence not worth analyzing, etc. cannot be determined.

In one embodiment, it is an object of the present invention to provide a method for analyzing data of high-throughput sequencing reaction, the method being capable of splitting output data based on a threshold determined according to a clear criterion.

In one embodiment, the nucleic acid analysis method of the present invention comprises: a library preparation step of preparing a library comprising at least one standard nucleic acid of specific copy number(s) and at least one analyte nucleic acid in a same system; a calibration curve data generation step of generating calibration curve data based on the copy number(s) of the standard nucleic acid of specific copy number(s); and an analyte nucleic acid analysis step of identifying at least one nucleotide sequence of the analyte nucleic acid while identifying the number(s) of the at least one nucleotide sequence of the at least one analyte nucleic acid using the calibration curve data.

In one embodiment, the present invention relates to a method for analyzing data of high-throughput sequencing reaction using at least one standard sample comprising a nucleic acid of specific copy number, the method comprising: a) preparing a library for the at least one standard sample and at least one sequence sample under a same condition; b) subjecting the library prepared in the step a) to a sequencing reaction to obtain output data comprising reads derived from the at least one standard sample and the at least one sequence sample; and c) dividing the reads in the output data, based on a threshold determined with reference to read number(s) derived from the at least one standard sample in the output data, into at least one read equal to or less than the threshold and at least one read equal to or more than the threshold.

The present specification encompasses the contents disclosed in Japanese Patent Application Nos. 2018-236746, 2019-015126, 2019-046689, and 2019-047881 to which the present application claims priority.

In one embodiment, the present invention can provide a nucleic acid analysis method that can conveniently and highly accurately analyze even a very small number of analyte nucleic acids.

In one embodiment, the present invention enables output data to be splitted based on a threshold determined according to a clear criterion. This allows, for example, to distinguish between data that should be used in analysis and other data among the output data to obtain analysis results with higher reliability.

BRIEF DESCRIPTION OF THE DRAWINGS

FIG. 3 is a diagram illustrating one example of the position of a well to be filled with a nucleic acid in the device of the present invention.

FIG. 4 is a diagram illustrating another example of the position of a well to be filled with a nucleic acid in the device of the present invention.

FIG. 30 shows raw data as well as data obtained with removing sequences having read numbers equal to or less than that of DNA600-G from the raw data (after removing ghost). FIG. 30 shows that reads of two types of microbes (*Acinetobacter* and *Bacillus firmus*) and reads of "Others" were removed when excluding sequences having a read number equal to or less than that of 10 copies of DNA600-G.

Figure 1A:
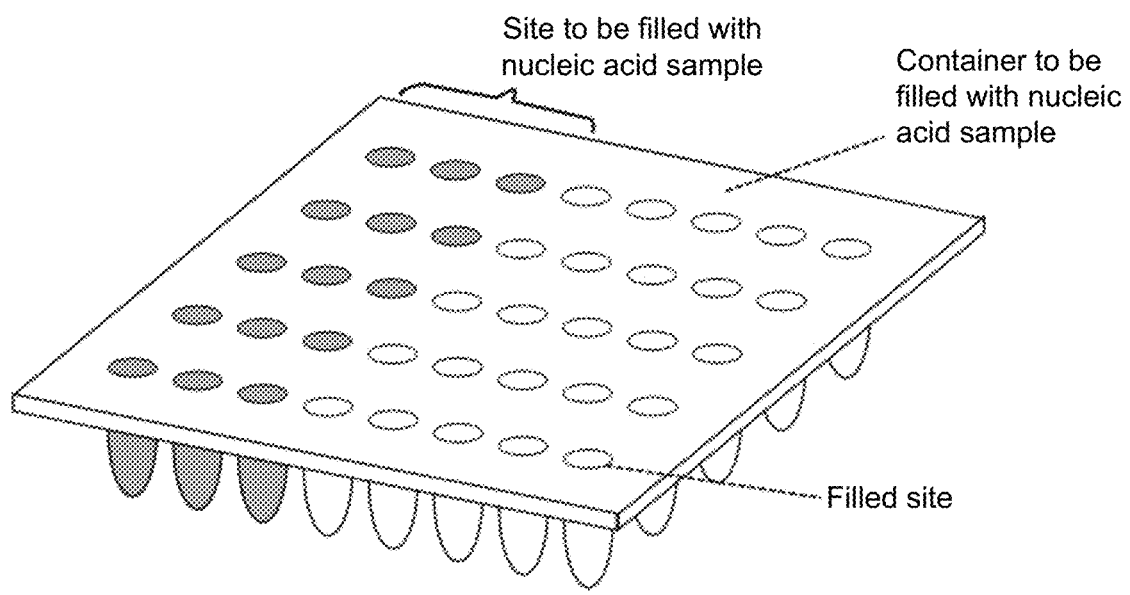
FIG. 1A is a perspective view illustrating one example of the device of the present invention.

DESCRIPTION OF THE EMBODIMENTS (Nucleic Acid Analysis Method and Nucleic Acid Analysis Program)

In one embodiment, the nucleic acid analysis method of the present invention comprises: a library preparation step of preparing a library comprising at least one standard nucleic acid of specific copy number(s) and at least one analyte nucleic acid in a same system; a calibration curve data generation step of generating calibration curve data based on the copy number(s) of the standard nucleic acid of specific copy number(s); and an analyte nucleic acid analysis step of identifying at least one nucleotide sequence of the analyte nucleic acid while identifying the number(s) of the at least one nucleotide sequence of the at least one analyte nucleic acid using the calibration curve data, and optionally further comprises an additional step.

In one embodiment, the nucleic acid analysis program of the present invention allows a computer to execute the processes of: generating calibration curve data on at least one standard nucleic acid by a calibration curve data generating unit based on the copy number of the standard nucleic acid of specific copy number(s) with respect to a library comprising the at least one standard nucleic acid of specific copy number(s) and at least one analyte nucleic acid prepared in a same system; and identifying a nucleotide sequence of the analyte nucleic acid by an analyte nucleic acid analyzing unit while identifying the number of the nucleotide sequence of the analyte nucleic acid using the calibration curve data, and optionally further allows the computer to execute an additional process.

In one embodiment, the nucleic acid analysis method can be suitably performed with a nucleic acid analyzing apparatus related to the nucleic acid analysis method. The library preparation step can be suitably performed with a library preparation unit. The calibration curve data generation step can be suitably performed with a calibration curve data generation unit. The analyte nucleic acid analysis step can be suitably performed with an analyte nucleic acid analyzing unit. The additional step can be performed with an additional unit.

The present inventors have studied a nucleic acid analysis method that can conveniently and highly accurately analyze even plural types of and a very small number of analyte nucleic acids, and consequently gained the following findings.

In a conventional technique, a sample having a known concentration has a measured value of the concentration of a nucleic acid itself, and is serially diluted before use to prepare standard samples for quantitative analysis. Therefore, for a very small amount of a standard sample with a high dilution ratio (a large number of times of dilutions), it is not certain that a diluted solution having the copy number of interest is precisely prepared. Thus, it is difficult to perform precise quantification for a very small amount of an analyte nucleic acid. In one embodiment, the present invention is based on these findings.

In one embodiment, the present invention is further based on the finding that it is not clear whether or not precise quantification can be performed for a very small amount of an analyte nucleic acid using an internal standard gene for microbial 16S rRNA gene quantification.

In one embodiment, a nucleic acid analyzing apparatus related to the nucleic acid analysis method of the present invention acts as an apparatus that carries out the nucleic acid analysis method of the present invention by retrieving and running the nucleic acid analysis program of the present invention. Specifically, the nucleic acid analyzing apparatus related to the nucleic acid analysis method of the present invention has the nucleic acid analysis program of the present invention that allows a computer to execute functions similar to those of the nucleic acid analysis method of the present invention. The nucleic acid analysis program of the present invention is not limited to the program run by the nucleic acid analyzing apparatus related to the nucleic acid analysis method of the present invention. For example, the nucleic acid analysis program of the present invention may be run by an additional computer or server or may be run by the nucleic acid analyzing apparatus related to the nucleic acid analysis method of the present invention in cooperation with any of an additional computer and server.

In other words, the nucleic acid analyzing apparatus related to the nucleic acid analysis method of the present invention is synonymous with carrying out the nucleic acid analysis method of the present invention. Hence, the details of the nucleic acid analyzing apparatus related to the nucleic acid analysis method of the present invention will also be clarified mainly with reference to the description about the nucleic acid analysis method of the present invention. Furthermore, the nucleic acid analysis program of the present invention achieves the nucleic acid analysis method of the present invention by using a hardware resource such as a computer. Hence, the details of the nucleic acid analysis program of the present invention will also be clarified through description about the nucleic acid analysis method of the present invention.

<Library Preparation Step and Library Preparation Unit>

The library preparation step is the step of preparing a library by disposing at least one standard nucleic acid of specific copy number(s) and at least one analyte nucleic acid in a same system. The library preparation step is suitably carried out by a library preparation unit.

The library means a collection comprising the analyte nucleic acid treated into a state that permits nucleic acid analysis. The library preferably comprises one or more, more preferably two or more analyte nucleic acids. The library comprising two or more analyte nucleic acids can be suitably used, for example, in an environmental survey to identify organism species.

The standard nucleic acid means a nucleic acid of a specific copy number used for acquiring calibration curve data mentioned later in nucleic acid analysis. The analysis is meant to include the identification of a nucleotide sequence and/or the identification of the copy number of each nucleotide sequence. The specific copy number is described in detail in description about a device used for the nucleic acid analysis method of the present invention mentioned later, so that the description about the specific copy number is omitted here.

The analyte nucleic acid means a nucleic acid (nucleotide sequence) to be analyzed as a sample. The type thereof is not particularly limited and can be appropriately selected according to the purpose. One type of analyte nucleic acid may be used alone, or two or more types of analyte nucleic acids may be used in combination. The number of the at least one analyte nucleic acid is not particularly limited and can be appropriately selected according to the purpose. One analyte nucleic acid may be used alone, or two or more analyte nucleic acids may be used in combination.

The analyte nucleic acid is not particularly limited and can be appropriately selected according to the purpose. Examples thereof include DNA, RNA, and cDNA. The analyte nucleic acid may comprise two or more nucleic acids (fragments) having different nucleotide sequences.

The treatment of the at least one analyte nucleic acid into a state that permits nucleic acid analysis is not particularly limited and can be appropriately selected according to the purpose. Examples thereof include a treatment to bind an adaptor sequence, and a treatment to perform nucleic acid amplification.

The treatment to hind an adaptor sequence is not particularly limited and can be appropriately selected according to the purpose. Examples thereof include a treatment to bind an oligonucleotide to at least any one of the 5' and 3' ends of the at least one analyte nucleic acid, a treatment to bind an oligonucleotide to be bound to at least any one of the 5' and 3' ends of the at least one analyte nucleic acid, and a treatment to bind a peptide or a protein.

The treatment to bind an oligonucleotide is not particularly limited and can be appropriately selected according to the purpose. Examples thereof include a method of preparing the library using same primers for the at least one standard nucleic acid and the at least one analyte nucleic acid, and a method of preparing the library using different primers for the at least one standard nucleic acid and the at least one analyte nucleic acid. Use of the method of preparing the library using the same primers for the at least one standard nucleic acid and the at least one analyte nucleic acid can render difference in amplification efficiency almost ignorable. Use of the method of preparing the library using different primers for the at least one standard nucleic acid and the at least one analyte nucleic acid allows the primers to be selected independently of the nucleotide sequence of the analyte nucleic acid and can therefore improve versatility.

Other examples of the treatment to bind an oligonucleotide include a method using transposon, a method using ligase, and a method using homologous recombination. For example, a method described in www.epibio.com/docs/default-source/forum-archive/forum-16-3---nextera-technology-for-ngs-dna-library-preparation---simultaneous-fragmentation-and-tagging-by-in-vitro-transposition.pdf?sfvrsn=4 can be suitably used as such a treatment to hind an oligonucleotide.

The treatment to bind a peptide or a protein is not particularly limited and can be appropriately selected according to the purpose. Examples thereof include a method using Rapid Sequencing Kit of MinION (Oxford Nanopore Technologies Ltd.).

For example, a method described in store.nanoporetech.com/catalog/product/view/id/219/s/rapid-sequencing-kit/category/28/ can be suitably used as the treatment to bind a peptide or a protein.

The adaptor sequence is not particularly limited and can be appropriately selected according to the purpose.

The treatment to perform nucleic acid amplification is not particularly limited and can be appropriately selected according to the purpose, as long as a specific nucleotide sequence (e.g., a gene) concerned can be amplified in the at least one analyte nucleic acid comprised in a sample.

The nucleic acid analysis method of the present invention amplifies the at least one standard nucleic acid and the at least one analyte nucleic acid in a same system, and can thereby improve the reliability of results about the at least one analyte nucleic acid because the number of the at least one standard nucleic acid has already been identified.

In this context, examples of the case of comprising the at least one standard nucleic acid and the at least one analyte nucleic acid in a same system include an embodiment comprising standard nucleic acids having different nucleotide sequences in a same system, and an embodiment comprising standard nucleic acids having the same nucleotide sequence in different systems.

The embodiment comprising standard nucleic acids having different nucleotide sequences in a same system means that the standard nucleic acids having different nucleotide sequences are comprised at specific copy numbers different from each other in a same system, i.e., two or more types of standard nucleic acids are comprised at specific copy numbers different from each other in a same system. This embodiment can improve the reliability of results of analyzing the at least one analyte nucleic acid. Examples of the case of being comprised at specific copy numbers different from each other in a same system include the amplification of mutually different nucleotide sequences A, B, and C at 3 levels, for example, 1 copy of the nucleotide sequence A, 10 copies of the nucleotide sequence B, and 50 copies of the nucleotide sequence C, in a same system. The "level" means that when a certain copy number is defined as "1", an alternative specific copy number is "10", and a further alternative specific copy number is "50", they are expressed as "3 levels".

The embodiment comprising standard nucleic acids having the same nucleotide sequence in different systems means that standard nucleic acids having the same nucleotide sequence are used, i.e., systems exist with respect to the respective levels (respective specific copy numbers) of the standard nucleic acids, and these systems comprise the same analyte nucleic acid. Use of the standard nucleic acids having the same nucleotide sequence can decrease the type of the standard nucleic acid used.

The library preparation is the step of pretreating at least one nucleic acid sample. The details of the library preparation step are known to those skilled in the art. The library preparation step may differ depending on each sequencing method and comprises, for example, but not limited to, one or more or all of the following steps: 1) enzymatically or mechanically fragmentating a nucleic acid depending on the read length of a sequencer; 2) adding an adaptor sequence necessary for a subsequent sequencing step by PCR or the like; 3) optionally amplifying a specific nucleic acid fragment by PCR or the like before or after the preceding step 2) (the amplification of a gene region can be performed by, for example, 4 to 50 cycles of an amplification step); and 4) purifying a nucleic acid molecule. Each step can be performed by a method known to those skilled in the art. See, for example, conditions described in Examples of the present application. The library preparation step may be performed using a commercially available kit, for example, TruSeq DNA PCR-Free (Illumina, Inc.), ACCEL-NGS™ library preparation kit (Swift Biosciences, Inc.), or Rapid Sequencing Kit (Oxford Nanopore Technologies Ltd:).

The library preparation step is not particularly limited and can be appropriately selected according to the purpose See, for example, an analysis method for next-generation sequencers published by Illumina, Inc. (www.adres.ehime-u.ac.jp/news/NGS1.pdf), Non-Patent document 1 (MiFish, a set of universal PCR primers for metaharcoding environmental DNA from fishes: detection of more than 230 subtropical marine species. M. Miya, et al., 2015), an analysis method for sequencing using nanopore devices (Oxford Nanopore Technologies Ltd.), an analysis method for sequencing using PacBio RS II/Sequel system (Pacific Biosciences of California, Inc.), and an analysis method for Ion Torrent™ semiconductor sequencing system series (Thermo Fisher Scientific Inc.).

Here, the phrase "the specific copy number of the standard nucleic acid has already been identified" in the nucleic acid analysis method of the present invention is described in detail. In one embodiment, the nucleic acid analysis method of the present invention is based on the premise that a device having a standard nucleic acid of an identified specific copy number is used.

—Device—

The device used in the nucleic acid analysis method of the present invention has at least one filled site, and the standard nucleic acid is contained at a specific copy number in the at least one filled site.

Use of the device in the nucleic acid analysis method of the present invention allows even a very small number of analyte nucleic acids to be analyzed (quantified) highly accurately. In the present invention, the term "very small amount" means that nucleic acids are "very few in number", and means, for example, 1,000 or less.

The specific copy number means the number of target or specific nucleic acids (or nucleotide sequences) of the standard nucleic acid contained in the filled site.

The target nucleotide sequence refers to a nucleotide sequence for which at least a primer region has been determined. Particularly, a nucleotide sequence having a determined full length is also referred to as a specific nucleotide sequence.

The specific number means that the number of target nucleic acids (nucleotide sequences) has been identified above a certain level of accuracy among the numbers of nucleic acids (nucleotide sequences).

Specifically, it can be said that the number of target nucleic acids (nucleotide sequences) actually contained in the filled site is known. In other words, the specific copy number according to the present application has higher numerical accuracy and reliability than those of a conventional predetermined number (calculated or estimated value) obtained by serial dilution, and is a controlled value independent of Poisson distribution, particularly, even for a very small amount of (1,000 or less) regions. Regarding the controlled value, a coefficient of variation (CV) which represents uncertainty preferably fall within the range of the value of either $CV<1/\sqrt{x}$ or $CV≤20\%$ with respect to mean x of specific copy numbers. Hence, use of the device having the filled site containing at least one target nucleic acid (nucleotide sequence) of specific copy number(s) enables a sample having the target nucleic acid (nucleotide sequence) to be tested qualitatively and quantitatively with higher precision than ever.

In this context, when the copy number of each target nucleotide sequence agrees with the number of nucleic acid molecules having the sequence, the "specific copy number" may correspond to the "number of molecules".

Specifically, in the case of, for example, norovirus, if the number of the virus is 1, then the number of the nucleic acid molecule is 1 and the copy number is 1. In the case of a yeast at the GI phase, if the number of the yeast is 1, then the number of the nucleic acid molecule (the number of the same chromosome) is 1 and the copy number is 1. In the case of a human cell at the G0/GI phase, if the number of the human cell is 1, then the number of the nucleic acid molecule (the number of the same chromosome) is 2 and the copy number is 2.

In the case of a yeast at the GI phase harboring target nucleotide sequences introduced at two locations, if the number of the yeast is 1, then the number of the nucleic acid molecule (the number of the same chromosome) is 1 and the copy number is 2.

In the present invention, the specific copy number of the nucleic acid is also referred to as a predetermined number or absolute number of the nucleic acid.

The specific copy number of the nucleic acid is preferably 1 (copy) or more and 1,000 (copies) or less, more preferably 100 (copies) or less, still more preferably 20 (copies) or less, further preferably 10 (copies) or less.

The specific copy number of the nucleic acid is preferably two or more different integers.

Examples of the combination of specific copy numbers of the nucleic acid include a combination of 1, 2, 3, 4, 5, 6, 7, 8, 9, and 10, a combination of 1, 3, 5, 7, and 9, and a combination of 2, 4, 6, 8, and 10.

Alternatively, the combination of specific copy numbers of the nucleic acid may be, for example, a combination of 1, 10, 50, 100, and 500 at 4 levels of 1, 10, 100, and 1,000. A calibration curve can be generated using the device in the nucleic acid analysis method of the present invention based on the combination of a plurality of different specific copy numbers.

Filled sites containing the nucleic acid at a plurality of different specific copy numbers may be the same or different. However, when a plurality of filled sites containing the nucleic acid exists, it is required to add the same analyte nucleic acid to the respective filled sites.

The method for disposing the library prepared in the library preparation step in the device having the at least one standard nucleic acid of specific copy number(s) is not particularly limited and can be appropriately selected according to the purpose. For example, it is preferred to add defined amounts of solutions or dispersion liquids prepared at a plurality of levels by the serial dilution of the library, or to add the library based on counting of a micro region or a carrier having a known number of nucleic acid molecules. The best method is preferably selected from among these methods depending on filling accuracy or a filling time required for each level. Uncertainty determined to each filled site preferably be suitably calculated by the aforementioned filling method or serial dilution preparation method.

Information on the specific copy number of the nucleic acid is not particularly limited and can be appropriately selected according to the purpose, as long as the information is related to the nucleic acid in the device. Examples thereof include uncertainty information, carrier information (mentioned later), and nucleic acid information.

The "uncertainty" is defined by ISO/IEC Guide 99: 2007 [International vocabulary of metrology—Basic and general concepts and associated terms (VIM)] as a "parameter, associated with the result of a measurement, that characterizes the dispersion of the values that could reasonably be attributed to the measurand".

In this context, the "values that could reasonably be attributed to the measurand" mean candidates of the true value of the measurand. Specifically, the uncertainty means information on the dispersion of the results of measurement attributed to an operation, an instrument, etc. related to the production of a measurement target. Larger uncertainty indicates larger dispersion predicted as the results of measurement.

The uncertainty may be, for example, standard deviation obtained from the results of measurement, or may be half the value of a confidence level represented as the width of values including the true value above predetermined probability.

The uncertainty can be calculated by a method based on, for example, Guide to the Expression of Uncertainty in Measurement (GUM: ISO/IEC Guide 98-3) or Guideline regarding Uncertainty in Measurement of the Japan Accreditation Board Note 10 test. For example, the method for calculating the uncertainty includes two methods, i.e., type A evaluation using statistics such as measurement values and type B evaluation using uncertainty information obtained from calibration certificates, manufacturers' specifications, published information, or the like.

The uncertainty can be represented by the same confidence level by converting all uncertainty components derived from an operation and measurement etc. to standard uncertainty. The standard uncertainty refers to the dispersion of means obtained from measurement values.

One exemplary method for calculating the uncertainty involves, for example, extracting components causing uncertainty, and calculating the uncertainty (standard deviation) of each component. The calculated uncertainty components are further combined by a sums-of-squares method to calculate combined standard uncertainty. Since the sums-of-squares method is used to calculate the combined standard uncertainty, a component with sufficiently small uncertainty among the components causing uncertainty can be ignored.

In the device of the present invention, a coefficient of variation of nucleic acids filled into filled sites may be used as the uncertainty information.

The coefficient of variation means the relative value of the dispersion of the numbers of nucleic acids filled into respective depressions when the nucleic acids are filled into the depressions. Specifically, the coefficient of variation means the filling accuracy of the numbers of nucleic acids filled into depressions. The coefficient of variation is a value obtained by dividing standard deviation σ by mean x of the numbers of the nucleic acid. In this context, a relational expression of the following expression 1 holds:

[Expression 1]

$$CV = \frac{\sigma}{x} \qquad \text{Expression 1}$$

wherein the coefficient of variation (CV) is a value obtained dividing standard deviation σ by mean x of the copy numbers of the nucleic acid (mean of the copy numbers of the added nucleic acid).

In general, nucleic acids are in a randomly dispersed state of Poisson distribution in a dispersion liquid. Therefore, standard deviation σ can be regarded as satisfying a relational expression of expression 2 given below with mean x of the copy numbers of the nucleic acid in a serial dilution method, i.e., in the randomly distributed state of Poisson distribution. In the case of diluting the nucleic acid dispersion liquid by the serial dilution method, the coefficient of variation (CV value) of mean x of the copy numbers of the nucleic acid is determined, as shown in Table 1 and FIG. 23, from the standard deviation σ and the mean x of the copy numbers of the nucleic acid according to expression 3 given below, which is derived from the expressions 1 and 2. The coefficient of variation (CV value) of copy numbers having dispersion based on Poisson distribution can be determined from FIG. 23.

[Expression 2]

$$\sigma = \sqrt{x} \qquad \text{Expression 2}$$

[Expression 3]

$$CV = \frac{1}{\sqrt{x}} \qquad \text{Expression 3}$$

TABLE 1

| Average copy number x | Coefficient of variation (CV) |
|---|---|
| 1.00E+00 | 100.00% |
| 1.00E+01 | 31.62% |
| 1.00E+02 | 10.00% |
| 1.00E+03 | 3.16% |
| 1.00E+04 | 1.00% |
| 1.00E+05 | 0.32% |
| 1.00E+06 | 0.10% |
| 1.00E+07 | 0.03% |
| 1.00E+08 | 0.01% |

Figure 23:
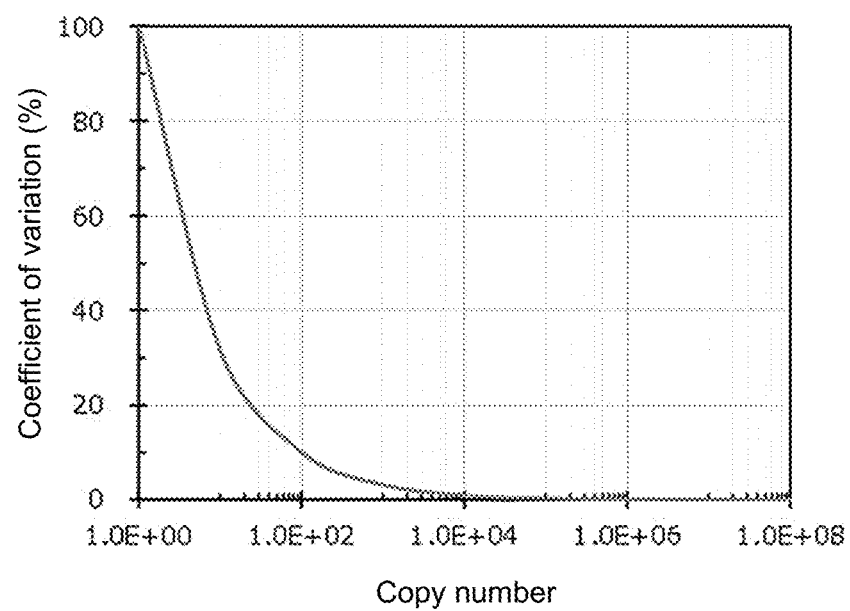
FIG. 23 is a graph illustrating the relationship between copy numbers having dispersion based on Poisson distribution and a coefficient of variation (CV).

As is evident from the results of Table 1 and FIG. 23, in the case of filling, for example, 100 copies (copy number=100) of the nucleic acid into filled sites by the serial dilution method, a mean of the copy numbers of the standard nucleic acid (nucleotide sequence) finally filled into reaction solutions has a coefficient of variation (CV value) of at least 10% even if the accuracy of other factors is ignored.

The specific copy number of the nucleic acid preferably satisfies the expression $CV<1/\sqrt{x}$, more preferably $CV<1/2\sqrt{x}$, wherein CV represents a coefficient of variation, and x represents a mean of the specific copy numbers of the nucleic acid.

The uncertainty information is preferably uncertainty information that is obtained from the whole device having a plurality of wells containing nucleic acids and is based on the specific copy number(s) of the nucleic acid(s) contained in the filled sites.

There are some possible components causing uncertainty. In the case of, for example, introducing the nucleic acid of interest into cells, and counting and dispensing the cells for preparation, examples of the components causing uncertainty include the number of nucleic acids in the cells, a unit of disposing the cells in the device (including an inkjet apparatus, or results ascribable to the action of each site in the apparatus, such as the timing of the action of the apparatus), frequency with which the cells are disposed at suitable positions in the device, and contamination (mixing of impurities) of nucleic acids into a cell suspension liquid due to the disruption of the cells in the cell suspension liquid.

Examples of the nucleic acid information, for example, information on the number of nucleic acids, include uncertainty information on the number of nucleic acids contained in the device.

<Filled Site>

The shape, number, capacity, material, color, etc. of the filled site are not particularly limited by and can be appropriately selected according to the purpose. The filled site may be synonymous with a well.

The shape of the filled site is not particularly limited and can be appropriately selected according to the purpose, as long as nucleic acids or the like can be disposed therein. Examples thereof include flat-bottomed, round-bottomed, U-bottomed, and V-bottomed depressions, and compartments on substrates. The shape of the filled site preferably agrees with the shape of a mold of a general thermal cycler.

The number of the filled site is at least 1, preferably 2 or more, more preferably 5 or more, still more preferably 50 or more.

Examples of the case where the number of the filled site is 1 include PCR tubes.

For example, a multiwell plate is suitably used when the number of the filled site is 2 or more.

Examples of the multiwell plate include 24-, 48-, 96-, 384-, or 1,536-well plates.

The capacity of the filled site is not particularly limited and can be appropriately selected according to the purpose. For example, the capacity is preferably 1 μL or larger and 1,000 μL or smaller in view of the amount of a sample used in a general nucleic acid test apparatus.

The material of the filled site is not particularly limited and can be appropriately selected according to the purpose. Examples thereof include polystyrene, polypropylene, polyethylene, fluororesin, acrylic resin, polycarbonate, polyurethane, polyvinyl chloride, and polyethylene terephthalate.

Examples of the color of the filled site include transparency, semitransparency, coloring, and complete light shielding.

The wettability of the filled site is not particularly limited and can be appropriately selected according to the purpose. For example, the filled site is preferably water-repellent. When the wettability of the filled site is a water-repellent, it can reduce the adsorption of nucleic acids to the inside wall of the filled site. Furthermore, when the wettability of the filled site is a water-repellent, nucleic acids, primers, and amplification reagents can be moved in a solution state in the filled site.

The method for rendering the inside wall of the filled site water-repellent is not particularly limited and can be appropriately selected according to the purpose. Examples thereof include a method of forming a fluororesin coating, fluorine plasma treatment, and embossing. Particularly, rendering the inside wall water-repellent so as to attain a contact angle of 100° or larger can reduce the risk of decreasing the number of nucleic acids and increasing uncertainty (or a coefficient of variation) due to a spill of a liquid.

<Base Material>

The device is preferably in a plate form having a base material provided with filled sites and may be a connected-type well tube such as an 8-strip tube, or a combination of unconnected wells.

The material, shape, size, structure, etc. of the base material is not particularly limited and can be appropriately selected according to the purpose.

The material of the base material is not particularly limited and can be appropriately selected according to the purpose. Examples thereof include semiconductors, ceramics, metals, glass, quartz glass, and plastics. Among them, a plastic is preferred.

Examples of the plastic include polystyrene, polypropylene, polyethylene, fluororesin, acrylic resin, polycarbonate, polyurethane, polyvinyl chloride, and polyethylene terephthalate.

The shape of the base material is not particularly limited and can be appropriately selected according to the purpose. For example, a sheet shape or a plate shape is preferred.

The structure of the base material is not particularly limited and can be appropriately selected according to the purpose. For example, a single-layer structure or a multi-layer structure may be used.

<Identifying Unit>

The device preferably has an identifying unit that permits identification of the specific copy number of the nucleic acid and uncertainty information thereon.

The identifying unit is not particularly limited and can be appropriately selected according to the purpose. Examples thereof include memories, IC chips, barcodes, QR Code(R), radio frequency identifiers (also referred to as "RFID" hereinafter), color codes, and prints.

The position of the identifying unit and the number of the identifying unit are not particularly limited and can be appropriately selected according to the purpose.

Examples of the information to be stored in the identifying unit include the specific copy number of the nucleic acid and uncertainty information thereon as well as analysis results (activity values, light intensity, etc.), the numbers of nucleic acids (e.g., cell counts), alive or dead cells, the copy numbers of specific nucleotide sequences, which filled sites among a plurality of filled sites nucleic acids are filled with, the types of nucleic acids, the date and time of measurement, and the names of measurers.

The information stored in the identifying unit can be read using various reading units. For example, a barcode reader is used as the reading unit when a barcode is used as the identifying unit.

The method for writing the information in the identifying unit is not particularly limited and can be appropriately selected according to the purpose. Examples thereof include manual input, a method of directly writing data therein from a liquid droplet forming apparatus that counts nucleic acids when the nucleic acids are dispensed to filled sites, the transfer of data stored in a server, and the transfer of data stored in a cloud.

<Additional Component>

The additional component is not particularly limited and can be appropriately selected according to the purpose. Examples thereof include a closing component.

—Closed Component—

The device preferably has a closing component in order to prevent the contamination of foreign matter into filled sites or the leakage of fillings, etc.

The closed member is preferably configured so as to be capable of closing at least one filled site and be capable of being detached at a cut line such that the filled site can be closed or opened individually.

The shape of the closing component is preferably a cap matching the inside wall diameter of a filled site, or a film shape that covers a well opening.

Examples of the material of the closing component include polyolefin resin, polyester resin, polystyrene resin, and polyamide resin.

The closing component preferably has a film shape capable of closing all filled sites at once. The closing component is preferably configured so as to differ in adhesion strength between a filled site that needs to be reopened and a filled site that does not need to be reopened, in order to reduce incorrect usage by users.

The filled site preferably contains at least any one of a primer and an amplification reagent.

The primer is a synthetic oligonucleotide having a complementary nucleotide sequence of 18 bases to 30 bases specific for template DNA for polymerase chain reaction (PCR). Two primers (a pair of primers), i.e., a forward primer and a reverse primer, are set so as to flank a region to be amplified.

Examples of the amplification reagent include DNA polymerase as an enzyme, 4 bases (dGTP, dCTP, dATP, and dTTP) as substrates, $Mg^{2+}$ (2 mM magnesium chloride), and buffers that retain the optimum pH (pH 7.5 to 9.5), for polymerase chain reaction (PCR).

The device preferably has a filled site for a negative control having 0 copies of a nucleic acid, and a filled site for a positive control having 10 copies or more of a nucleic acid.

When detection is sensed in the negative control and when non-detection is sensed in the positive control, it is suggested that the detection system (reagent or apparatus) has an abnormality. By using the negative control and the positive control, users can immediately notice when a problem arises, and discontinue the measurement and check where the problem arises.

The states of the nucleic acid, the primer, and the amplification reagent in the filled site are not particularly limited and can be appropriately selected according to the purpose. For example, these components may be in any state of a solution or a solid. Particularly, a solution state is preferred from the viewpoint of usability. When the components are in a solution state, users can immediately use the components in tests. Particularly, a solid state is preferred, and a dry state is more preferred, from the viewpoint of transportation. When the components are in a dry state, the reaction rate of degradation of an amplifiable reagent by a degradative enzyme or the like can be reduced, and the preservability of the nucleic acid, the primer, and the amplification reagent can be improved.

It is desirable that the filled site should be filled with suitable amounts of the nucleic acid, the primer, and the amplification reagent in a dry solid state such that these components can be dissolved in a buffer or water immediately before use of the device to be immediately used as a reaction solution.

The drying method is not particularly limited and can be appropriately selected according to the purpose. Examples thereof include freeze drying, drying by heating, hot-air drying, vacuum drying, steam drying, drying by suction, infrared drying, barrel drying, and spin drying.

Figure 1B:
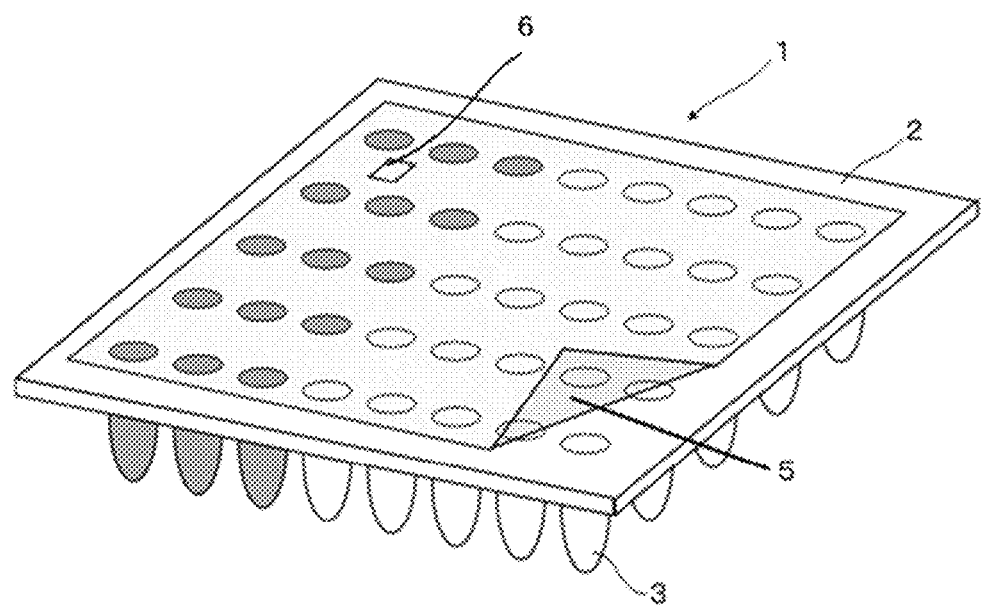
FIG. 1B is a perspective view illustrating another example of the device of the present invention.
Figure 2:
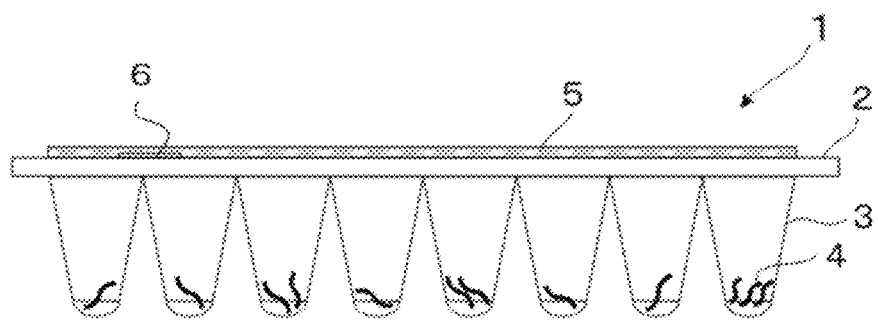
FIG. 2 is a side view illustrating one example of the device of the present invention.

In this context, FIG. 1A is a perspective view illustrating one example of device (also referred to as nucleic acid sample filled container) 1 related to the nucleic acid analysis method of the present invention. FIG. 1B is a perspective view illustrating another example of device 1 related to the nucleic acid analysis method of the present invention. FIG. 2 is a side view of the device 1 of FIG. 1B. The device 1 has base material 2 provided with a plurality of filled sites (wells) 3, and nucleic acid 4 is filled at a specific copy number into the filled sites (wells) 3 (inside space regions surrounded by filled site (well) walls constituting the filled sites (wells)) (also referred to as nucleic acid sample-filled sites). In this device 1, the specific copy number of the nucleic acid is associated with uncertainty information on the specific copy number of the nucleic acid. FIGS. 1B and 2 each illustrates an example of device 1 in which openings of filled sites (wells) 3 are covered with closing component 5.

As illustrated in FIGS. 1B and 2, for example, an IC chip or a barcode (identifying unit 6) that stores the number of a reagent filled into each filled site (well) 3, and uncertainty (probability) information on the number, or information associated with these informations is disposed at a position between the closing component 5 and the base material 2 and other than the openings of the filled sites (wells). This is suitable for preventing the unintended alteration or the like of the identifying unit.

Such a device having the identifying unit is discriminable from a general filled site (well) plate having no identifying unit. This can prevent mix-up.

FIG. 3 is a diagram illustrating one example of the position of a filled site (well) to be filled with a nucleic acid in the device related to the nucleic acid analysis method of the present invention. The numbers on the filled sites (wells) in FIG. 3 represent the specific copy numbers of the nucleic acid. The unnumbered filled sites (wells) in FIG. 3 are filled sites (wells) for sample or control measurement.

FIG. 4 is a diagram illustrating another example of the position of a filled site (well) to be filled with a nucleic acid in the device related to the nucleic acid analysis method of the present invention. The numbers on the filled sites (wells) in FIG. 4 represent the specific copy numbers of the nucleic acid. The unnumbered filled sites (wells) in FIG. 4 are filled sites (wells) for sample or control measurement.

—Nucleic Acid—

The nucleic acid or the nucleic acid molecule is a macromolecular organic compound formed by regularly binding of a nitrogen-containing base derived from purine or pyrimidine, sugar, and phosphate, and also includes a fragment of the nucleic acid, or an analog of the nucleic acid or the fragment thereof, etc.

The nucleic acid is not particularly limited and can be appropriately selected according to the purpose. Examples thereof include DNA, RNA, and cDNA.

The nucleic acid or the nucleic acid fragment may be a natural product obtained from an organism, or a processed product thereof, and may be produced through the use of a gene recombination technique or may be an artificially synthesized nucleic acid obtained by chemical synthesis, etc. These nucleic acids (fragments) may be used alone or may be used in combination of two or more thereof. The artificially synthesized nucleic acid can be prepared as a low molecule with a decreased amount of impurities, and can therefore improve initial reaction efficiency.

The artificially synthesized nucleic acid means a nucleic acid obtained by artificially synthesizing a nucleic acid composed of constituents (base, deoxyribose, and phosphate) similar to those of naturally occurring DNA or RNA. The artificially synthesized nucleic acid includes, for example, not only a nucleic acid having a nucleotide sequence encoding a protein but a nucleic acid having any nucleotide sequence.

Examples of the analog of the nucleic acid or the nucleic acid fragment include nucleic acids or nucleic acid fragments bound to a non-nucleic acid component, nucleic acids or a nucleic acid fragments labeled with a labeling agent such as a fluorescent dye or an isotope (e.g., primers or probes labeled with a fluorescent dye or a radioisotope), and artificial nucleic acids (e.g., PNA, BNA, and LNA) obtained by partially changing the chemical structures of nucleotides constituting the nucleic acid or the nucleic acid fragment.

The form of the nucleic acid is not particularly limited and can be appropriately selected according to the purpose. Examples thereof include double-stranded nucleic acids, single-stranded nucleic acids, and partially double-stranded or single-stranded nucleic acids. A circular or linear plasmid may be used.

The nucleic acid may be modified or mutated.

The nucleic acid preferably has a target nucleotide sequence.

The target nucleotide sequence is not particularly limited and can be appropriately selected according to the purpose. Examples thereof include nucleotide sequences used in infectious disease tests, non-natural nucleotide sequences that do not naturally occur, nucleotide sequences derived from animal cells, nucleotide sequences derived from plant cells, nucleotide sequences derived from fungal cells, nucleotide sequences derived from bacteria, and nucleotide sequences derived from viruses. These target nucleotide sequences may be used alone or may be used in combination of two or more thereof.

In the case of using a non-natural nucleotide sequence, GC content percentage is preferably 30% or more and 70% or less of the target nucleotide sequence, and the GC content is preferably constant (see e.g., SEQ ID NO: 6).

The base length of the target nucleotide sequence is not particularly limited and can be appropriately selected according to the purpose. Examples thereof include base lengths of 20 base pairs (or mer) or more and 10,000 base pairs (or mer) or less.

In the case of using a nucleotide sequence used in infectious disease tests, the nucleotide sequence is not particularly limited and can be appropriately selected according to the purpose, as long as the nucleotide sequence comprises a nucleotide sequence unique to the infectious disease. The nucleotide sequence preferably comprises a nucleotide sequence specified by an official method or a notified method.

The nucleic acid may be a nucleic acid derived from the cell used, or may be a nucleic acid introduced by transfection. In the case of using a nucleic acid introduced by transfection and a plasmid as the nucleic acid, it is preferred to confirm that 1 copy of the nucleic acid is introduced in 1 cell. The method for confirming that 1 copy of the nucleic acid is introduced is not particularly limited and can be appropriately selected according to the purpose. This can be confirmed by using, for example, a sequencer, PCR, or Southern blot.

The type of the nucleic acid having the target nucleotide sequence introduced by transfection may be one type or may be two or more types. In the case of introducing one type of nucleic acid by transfection, similar nucleotide sequences may be introduced in tandem according to the purpose.

The transfection method is not particularly limited and can be appropriately selected according to the purpose, as long as a specific nucleic acid sequence can be introduced at an intended copy number into an intended site. Examples thereof include homologous recombination, CRISPR/Cas9, CRISPR/Cpf1, TALEN, zinc finger nuclease, Flip-in, and Jump-in. Among them, homologous recombination is preferred for yeast fungi because of high efficiency and easy control.

—Carrier—

The nucleic acid is preferably handled in a state supported by a carrier. The nucleic acid is preferably in, for example, a form supported by (more preferably enclosed in) a carrier having a particle shape (carrier particle).

The carrier is not particularly limited and can be appropriately selected according to the purpose. Examples thereof include cells, resins, liposomes, microcapsules, metal particles, magnetic particles, ceramic particles, polymer particles, and protein particles.

—Cell—

The cell means a structural and functional unit having a nucleic acid and constituting an organism.

The cell is not particularly limited and can be appropriately selected according to the purpose. For example, every cell can be used, irrespective of whether to be a eukaryotic cell, a prokaryotic cell, a multicellular organism cell, or a unicellular organism cell. These cells may be used alone or may be used in combination of two or more thereof.

The eukaryotic cell is not particularly limited and can be appropriately selected according to the purpose. Examples thereof include animal cells, insect cells, plant cells, fungi, algae, and protozoans. These eukaryotic cells may be used alone or may be used in combination of two or more thereof. Among them, an animal cell or a fungus is preferred.

The adherent cell may be a primary cell collected directly from a tissue or an organ, or may be obtained by several passages of the primary cell collected directly from a tissue or an organ, and can be appropriately selected according to the purpose. Examples thereof include differentiated cells and undifferentiated cells.

The differentiated cell is not particularly limited and can be appropriately selected according to the purpose. Examples thereof include: hepatocytes which are parenchymal cells of the liver; stellate cells; Kupffer cells; vascular endothelial cells; endothelial cells such as sinusoidal endothelial cells and corneal endothelial cells; fibroblasts; osteoblasts; osteoclasts; periodontium-derived cells; epidermal cells such as epidermal keratinocytes; tracheal epithelial cells; gastrointestinal epithelial cells; cervical epithelial cells; epithelial cells such as corneal epithelial cells; mammary gland cells; pericytes; muscle cells such as smooth muscle cells and cardiac muscle cells; renal cells; pancreas islet cells; nerve cells such as peripheral nerve cells and optic nerve cells; chondrocytes; and bone cells.

The undifferentiated cell is not particularly limited and can be appropriately selected according to the purpose. Examples of the undifferentiated cell include: pluripotent stem cells such as embryonic stem cells and mesenchymal stem cells having multipotency; unipotent stem cells such as vascular endothelial progenitor cells having unipotency; and iPS cells.

The fungus is not particularly limited and can be appropriately selected according to the purpose. Examples thereof include molds and yeast fungi. These fungi may be used alone or may be used in combination of two or more thereof.

Among them, a yeast fungus is preferred because its cell cycle can be adjusted and a monoploid can be used.

The cell cycle means a process during which, when cells grow, cell division occurs and cells resulting from the cell division (daughter cells) become cells that undergo cell division again (mother cells) to produce new daughter cells.

The yeast fungus is not particularly limited and can be appropriately selected according to the purpose. For example, the yeast fungus is preferably synchronized-cultured in synchrony with the G0/G1 phase and fixed to the G1 phase.

The yeast fungus is preferably, for example, a Bar-1-deficient yeast with increased sensitivity to pheromone (sex hormone) that controls the cell cycle to the G1 phase. When the yeast fungus is a Bar-1-deficient yeast, the abundance ratio of a yeast fungus having an uncontrollable cell cycle can be decreased. For example, this can prevent increase in the number of a specific nucleic acid in cells contained in filled sites (wells).

The prokaryotic cell is not particularly limited and can be appropriately selected according to the purpose. Examples thereof include eubacteria and archaebacteria. These prokaryotic cells may be used alone or may be used in combination of two or more thereof.

The cell is preferably a dead cell. When the cell is a dead cell, cell division after separation can be prevented.

The cell is preferably a cell capable of emitting light upon reception of light. The cell capable of emitting light upon reception of light can be landed into filled sites (wells) with its cell count controlled highly accurately.

The reception of light means that the cell is subjected to light.

The optical sensor means a passive sensor that collects, by means of a lens, any light from visible light, which is detectable by the human eye, to light in the near-infrared, short-wavelength infrared, and thermal infrared regions with a higher wavelength than that of the visible light, and acquires the shape, etc. of the object cell as image data.

—Cell Capable of Emitting Light Upon Reception of Light—

The cell capable of emitting light upon reception of light is not particularly limited and can be appropriately selected according to the purpose, as long as the cell is capable of emitting light upon reception of light. Examples thereof include cells stained with a fluorescent dye, cells expressing a fluorescent protein, and cells labeled with a fluorescently labeled antibody.

Examples of the staining site with a fluorescent dye, the expression site of a fluorescent protein, or the labeling site with a fluorescently labeled antibody in the cell include, but are not particularly limited to, the whole cells, cell nuclei, and cell membranes.

—Fluorescent Dye—

Examples of the fluorescent dye include fluoresceins, azos, rhodamines, coumarins, pyrenes, and cyanines. These fluorescent dyes may be used alone or may be used in combination of two or more thereof. Among them, fluoresceins, azos, or rhodamines are preferred, and eosin, Evans blue, trypan blue, rhodamine 6G, rhodamine B, or rhodamine 123 is more preferred.

A commercially available product can be used as the fluorescent dye. Examples of the commercially available product include trade name: Eosin Y (manufactured by Wako Pure Chemical Industries, Ltd.), trade name: Evans blue (manufactured by Wako Pure Chemical Industries, Ltd.), trade name: Trypan blue (manufactured by Wako Pure Chemical Industries, Ltd.), trade name: Rhodamine 6G (manufactured by Wako Pure Chemical Industries, Ltd.), trade name: Rhodamine B (manufactured by Wako Pure Chemical Industries, Ltd.), and trade name: Rhodamine 123 (manufactured by Wako Pure Chemical Industries, Ltd.).

—Fluorescent Protein—

Examples of the fluorescent protein include Sirius, EBFP, ECFP, mTurquoise, TagCFP, AmCyan, mTFP1, Midoriishi-Cyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. These fluorescent proteins may be used alone or may be used in combination of two or more thereof.

—Fluorescently Labeled Antibody—

The fluorescently labeled antibody is not particularly limited and can be appropriately selected according to the purpose, as long as the fluorescently labeled antibody has a fluorescent label. Examples thereof include CD4-FITC and CD8-PE. These fluorescently labeled antibodies may be used alone or may be used in combination of two or more thereof.

The volume-average particle size of the cell is preferably 30 µm or smaller, more preferably 10 µm or smaller, particularly preferably 7 µm or smaller, in a free state. The cell having a volume-average particle size of 30 µm or smaller can be suitably used in a liquid droplet discharging unit such as an inkjet method or a cell sorter.

The volume-average particle size of the cell can be measured by, for example, the following measurement method.

A 10 µL aliquot is sampled from a prepared already stained yeast dispersion liquid, and placed on a PMMA plastic slide, and the volume-average particle size can be measured by using an automated cell counter (trade name: Countess Automated Cell Counter, manufactured by Invitrogen Corp.). A cell number can also be determined by a similar measurement method.

The concentration of the cell in a cell suspension liquid is not particularly limited and can be appropriately selected according to the purpose. The concentration is preferably $5 \times 10^4$ cells/mL or higher and $5 \times 10^8$ cells/mL or lower, more preferably $5 \times 10^4$ cells/mL or higher and $5 \times 10^7$ cells/mL or lower. Cells with a cell number of $5 \times 10^4$ cells/mL or higher and $5 \times 10^8$ cells/mL or lower can be reliably contained in discharged liquid droplets. The cell number can be measured using an automated cell counter (trade name: Countess Automated Cell Counter, manufactured by Invitrogen Corp.), as in the method for measuring the volume-average particle size.

The cell number of the cell having the nucleic acid is not particularly limited and can be appropriately selected according to the purpose, as long as the cell number is two or more.

—Resin—

The material, shape, size, and structure of the resin is not particularly limited, and can be appropriately selected according to the purpose, as long as the resin can support the nucleic acid.

—Liposome—

The liposome is a lipid vesicle formed from a lipid bilayer containing a lipid molecule, and specifically means a lipid-containing closed vesicle having a space isolated from the outside world by a lipid bilayer resulting from the polarities of a hydrophobic group and a hydrophilic group of a lipid molecule.

The liposome is a closed vesicle formed from a lipid bilayer membrane using a lipid, and the closed vesicle has an aqueous phase within its space (inner aqueous phase). The inner aqueous phase contains water and the like. The liposome may have a single lamellar structure (unilamellar structure or single bilayer membrane) or may have a multiple lamellar structure (multilamellar structure or a large number of bilayer membranes having an onion-like structure where individual layers are partitioned with water-like layers).

The liposome is preferably a liposome that can enclose the nucleic acid therein. Its form is not particularly limited. The term "enclose" means an embodiment in which the nucleic acid is contained in the inner aqueous phase and the membrane itself of the liposome. Examples thereof include an embodiment in which the nucleic acid included in the closed space formed by the membrane, or the nucleic acid enclosed in the membrane itself. A combination thereof may be used.

The size (average particle size) of the liposome is not particularly limited as long as the liposome can enclose the nucleic acid therein. The liposome preferably is in spherical or nearly spherical form.

The component constituting the lipid bilayer (membrane component) of the liposome is selected from lipids. Any lipid that is soluble in a mixed solvent of a water-soluble organic solvent and an ester organic solvent can be used. Specific examples of the lipid include phospholipid, lipids other than phospholipid, cholesterols and derivatives thereof. Such a component may be composed of a single type of component or plural types of components.

—Microcapsule—

The microcapsule means a tiny particle having a wall material and a hollow structure, and can enclose the nucleic acid in the hollow structure.

The microcapsule is not particularly limited, and its wall material, size, etc. can be appropriately selected according to the purpose.

Examples of the wall material of the microcapsule include polyurethane resin, polyurea, polyurea-polyurethane resin, urea-formaldehyde resin, melamine-formaldehyde resin, polyamide, polyester, polysulfonamide, polycarbonate, polysulfinate, epoxy, acrylic acid ester, methacrylic acid ester, vinyl acetate, and gelatin. These wall materials may be used alone or may be used in combination of two or more thereof.

The size of the microcapsule is not particularly limited and can be appropriately selected according to the purpose, as long as the microcapsule can enclose the nucleic acid therein.

The method for producing the microcapsule is not particularly limited and can be appropriately selected according to the purpose. Examples thereof include an in-situ method, an interfacial polymerization method, and a coacervation method.

Other form of the nucleic acid may be a solution of the nucleic acid molecule mentioned above, or a dispersion liquid having tiny compartments created with micro regions or carriers. The medium of the solution or the dispersion liquid is preferably water or a water-soluble solvent such as ethanol, DMSO, acetone, or DMF. The carrier may have any form such as a metal particle, a magnetic particle, a ceramic particle, a polymer particle, or a protein particle. Examples of the micro region include droplets and emulsions. The sample comprising the nucleic acid molecule may have any form such as a cell, a virus, a droplet, or an emulsion.

<Method for Producing Device>

Hereinafter, a method for producing a device using cells having a specific nucleic acid as the nucleic acid is described.

The method for producing the device related to the nucleic acid analysis method of the present invention comprises: a cell suspension liquid production step of producing a cell suspension liquid containing a plurality of cells having a specific nucleic acid, and a solvent; a liquid droplet landing step of sequentially landing liquid droplets into filled sites (wells) of a plate by discharging the cell suspension liquid as the liquid droplets; a cell counting step of counting the cells contained in the liquid droplets using a sensor after discharging the liquid droplets and before landing the liquid droplets into filled sites (wells); and a nucleic acid extraction step of extracting the nucleic acid from the cells in the filled sites (wells). This method preferably comprises an uncertainty calculation step for each step, an output step, and a recording step and optionally further comprises an additional step.

<<Cell Suspension Liquid Production Step>>

The cell suspension liquid production step is the step of producing a cell suspension liquid containing a plurality of cells having a specific nucleic acid, and a solvent.

The solvent means a liquid for use in dispersing the cells.

The suspension for the cell suspension liquid means a state where the cells are dispersed in the solvent.

The production means creation.

—Cell Suspension Liquid—

The cell suspension liquid contains a plurality of cells having a specific nucleic acid, and a solvent. The cell suspension liquid preferably contains an additive and optionally further comprises an additional component.

The plurality of cells having a specific nucleic acid are as mentioned above.

—Solvent—

The solvent is not particularly limited and can be appropriately selected according to the purpose. Examples thereof include water, culture media, separator liquids, diluent liquids, buffer solutions, organic matter lysis solutions, organic solvents, polymer gel solutions, colloidal dispersion liquids, aqueous electrolyte solutions, aqueous solutions of inorganic salts, aqueous metal solutions, and mixed liquids thereof. These solvents may be used alone or may be used in combination of two or more thereof. Among them, water or a buffer solution is preferred, and water, phosphate-buffered saline (PBS), or a Tris-EDTA buffer solution (TE) is more preferred.

—Additive—

The additive is not particularly limited and can be appropriately selected according to the purpose. Examples thereof include surfactants, nucleic acids, and resins. These additives may be used alone or may be used in combination of two or more thereof.

The surfactant can prevent the aggregation between cells and improve continuous discharge stability.

The surfactant is not particularly limited and can be appropriately selected according to the purpose. Examples thereof include ionic surfactants and nonionic surfactants. These surfactants may be used alone or may be used in combination of two or more thereof. Among them, a nonionic surfactant is preferred, since the nonionic surfactant neither denatures nor deactivates proteins, although depending on the amount of the surfactant added.

Examples of the ionic surfactant include fatty acid sodium salt, fatty acid potassium salt, sodium alpha-sulfo fatty acid ester, sodium linear alkylbenzenesulfonate, sodium alkyl sulfuric acid ester, sodium alkyl ether sulfuric acid ester, and sodium alpha-olefinsulfonate. These ionic surfactants may be used alone or may be used in combination of two or more thereof. Among them, fatty acid sodium salt is preferred, and sodium dodecyl sulfate (SDS) is more preferred.

Examples of the nonionic surfactant include alkyl glycoside, alkyl polyoxyethylene ether (Brij series, etc.), octyl phenol ethoxylate (Triton X series, Igepal CA series, Nonidet P series, Nikkol OP series, etc.), polysorbates (Tween series such as Tween 20, etc.), sorbitan fatty acid ester, polyoxyethylene fatty acid ester, alkyl maltoside, sucrose fatty acid ester, glycoside fatty acid ester, glycerin fatty acid ester, propylene glycol fatty acid ester, and fatty acid monoglyceride. These nonionic surfactants may be used alone or may be used in combination of two or more thereof. Among them, polysorbates are preferred.

The content of the surfactant is not particularly limited and can be appropriately selected according to the purpose. The content is preferably 0.001% by mass or more and 30% by mass or less with respect to the total amount of the cell suspension liquid. The content of 0.001% by mass or more can produce effects provided by the addition of the surfactant. The surfactant having a content of 30% by mass or less can suppress cell aggregation and can therefore strictly control the copy number of the nucleic acid in the cell suspension liquid.

The nucleic acid is not particularly limited and can be appropriately selected according to the purpose, as long as the nucleic acid has no influence on the detection of the nucleic acid to be detected. Examples thereof include ColE1 DNA. The nucleic acid can prevent the nucleic acid having a target nucleotide sequence from adhering to the wall surface of filled sites (wells), etc.

The resin is not particularly limited and can be appropriately selected according to the purpose. Examples thereof include polyethylenimide.

—Other Material—

Other material is not particularly limited and can be appropriately selected according to the purpose. Examples thereof include cross-linking agents, pH adjusters, antiseptics, antioxidants, osmotic pressure adjusters, wetting agents, and dispersants.

[Method for Dispersing Cell]

The method for dispersing the cells is not particularly limited and can be appropriately selected according to the purpose. Examples thereof include medium modes such as bead mills, ultrasonic modes such as ultrasonic homogenizers, and modes that exploit difference in pressure, such as French presses. These methods may be used alone or may be used in combination of two or more thereof. Among them, an ultrasonic mode is more preferred, since this mode does less damage to the cells. A medium mode might disrupt cell membranes or cell walls due to strong cracking ability, or the medium may be mixed into the cell dispersion liquid as contamination.

[Method for Screening Cell]

The method for screening the cells is not particularly limited and can be appropriately selected according to the purpose. Examples thereof include wet classification, and screening using a cell sorter or a filter. These methods may be used alone or may be used in combination of two or more thereof. Among them, screening using a cell sorter or a filter is preferred, since this method does less damage to the cells.

It is preferred for the cells to estimate the number of the nucleic acid having a target nucleotide sequence from the cell number of the cell suspension liquid by measuring the cell cycles of the cells.

The measuring the cell cycles means that a cell number based on cell division is numerically converted.

The estimation of the number of the nucleic acid means that the copy number of the nucleic acid is determined from the cell number.

The counting target may be the number of the incorporated target nucleotide sequence, not the cell number. Usually, the number of the target nucleotide sequence can be considered as being equal to the cell number, since cells in which one region is incorporated as the target nucleotide sequence per cell are selected, or the target nucleotide sequence is introduced by gene recombination. However, cells undergo cell division at a specific cycle to intracellularly replicate a nucleic acid. Although the cell cycle differs depending on the types of cells, the expectation and uncertainty of the number of the target nucleotide sequence contained per cell can be calculated by sampling a predetermined amount of a solution from the cell suspension liquid, and measuring the cycles of a plurality of cells. This is attained, for example, by observing nuclear stained cells using a flow cytometer.

The uncertainty means information on the dispersion of the results of measurement attributed to an operation, an instrument, etc. related to the production of a measurement target.

The calculation means that a numerical value is calculated.

Figure 5:
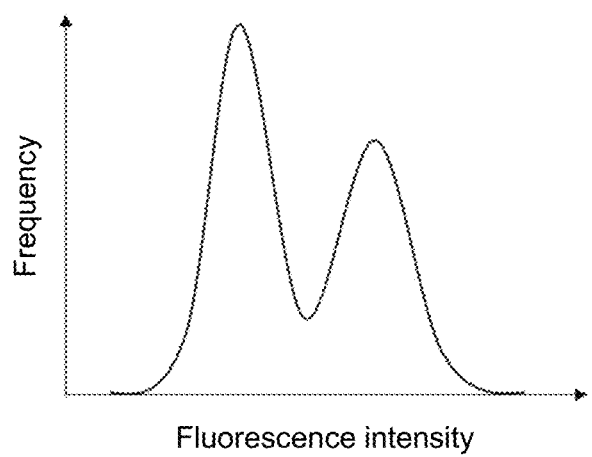
FIG. 5 is a graph illustrating one example of the relationship between frequency of cells that have already replicated DNA and fluorescence intensity.

FIG. 5 is a graph illustrating one example of the relationship between frequency of cells that have already replicated DNA and fluorescence intensity. As illustrated in FIG. 5, two peaks appear on a histogram depending on the presence or absence of replication of the target nucleotide sequence. Therefore, the percentage of presence of the cells that have already replicated DNA can be calculated. The average number of the target nucleotide sequence contained per cell can be calculated from the calculation results, and can be multiplied by the aforementioned cell counting results to calculate the estimated value of the target nucleotide sequence.

It is also preferred to perform treatment of controlling cell cycles before preparation of the cell suspension liquid. The number of the target nucleotide sequence can be accurately calculated from the cell number by controlling the cell cycles into a state before or after occurring the replication as mentioned above.

It is preferred to calculate uncertainty for the specific copy number to be estimated. The uncertainty thus calculated can be represented as variance or standard deviation based on the numerical value, and then output. In the case of combining a plurality of influencing factors, the square-root of sum of squares of standard deviation generally used may be used. For example, the percentage of correct answers about the number of discharged cells, the DNA numbers of the cells, and the landing rate at which the discharged cells are landed into filled sites (wells) can be used as the factors. Among them, a significant item may be selected and calculated.

<<Liquid Droplet Landing Step>>

The liquid droplet landing step is the step of sequentially landing liquid droplets into filled sites (wells) of a device by discharging the cell suspension liquid as the liquid droplets.

The liquid droplet means a mass of a liquid bounded by surface tension.

The discharge means that the cell suspension liquid is allowed to fly as liquid droplets.

The term "sequentially" means in sequence and in order.

The landing means that the liquid droplet is allowed to reach a filled site (well).

A unit of discharging the cell suspension liquid as liquid droplets (hereinafter, also referred to as a "discharging head") can be suitably used as a discharging unit.

Examples of the mode of discharging the cell suspension liquid as liquid droplets include on-demand modes and continuous modes in an inkjet method. Among them, a continuous mode tends to increase the dead volume of the cell suspension liquid used, since liquid droplet formation is continuously performing even during empty discharge before achieving a stable discharge state, adjustment of the amount of the liquid droplets, and moving between filled sites (wells). In the present invention, it is preferred to reduce the influence of dead volume, from the viewpoint of adjusting the cell number. Therefore, among the two modes described above, an on-demand mode is more suitable.

Examples of the on-demand mode include a plurality of known modes such as a pressure application mode of discharging a liquid by applying pressure to the liquid, a thermal mode of discharging a liquid by film boiling through heating, and an electrostatic mode of forming liquid droplets by pulling the liquid droplets through electrostatic attraction. Among them, a pressure application mode is preferred for the following reasons.

The electrostatic mode requires establishing an electrode that faces a discharging part which retains the cell suspension liquid and forms liquid droplets. In the method for producing the device according to the present invention, a plate for receiving liquid droplets is disposed such that the plate faces the discharging part. Thus, the absence of electrode disposement is preferred for enhancing the degree of freedom of a plate configuration.

The thermal mode generates local heat, which might influence cells which are biomaterials or cause a stick to a heater part (kogation). The influence of heat depends on the contents and the purpose of the plate and is therefore not necessarily required to be excluded. However, the pressure application mode is preferred, since this mode is less susceptible to a stick to a heater part than the thermal mode.

Examples of the pressure application mode include a mode of applying pressure to a liquid using a piezoelectric element, and a mode of applying pressure thereto using a valve such as an electromagnetic valve. Configuration examples of a liquid droplet formation device usable in the liquid droplet discharge of the cell suspension liquid are illustrated in FIGS. 6A to 6C.

Figure 6A:
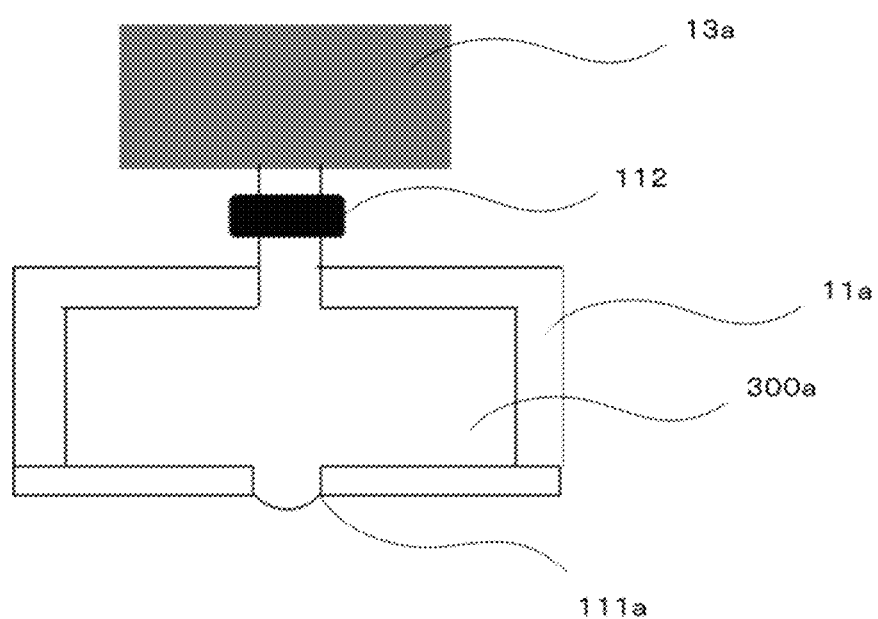
FIG. 6A is a schematic view illustrating one example of a discharging head in an electromagnetic valve mode.

FIG. 6A is a schematic view illustrating one example of a discharging head in an electromagnetic valve mode. The discharging head in an electromagnetic valve mode has electric motor 13a, solenoid valve 112, liquid chamber 11a, cell suspension liquid 300a, and nozzle 111a.

For example, a dispenser from TechElan LLC can be suitably used as the discharging head in an electromagnetic valve mode.

Figure 6B:
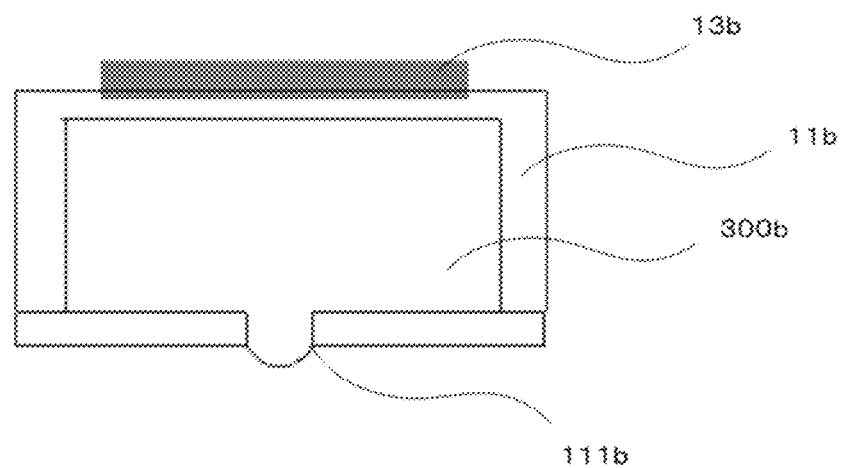
FIG. 6B is a schematic view illustrating one example of a discharging head in a piezoelectric mode.
Figure 6C:
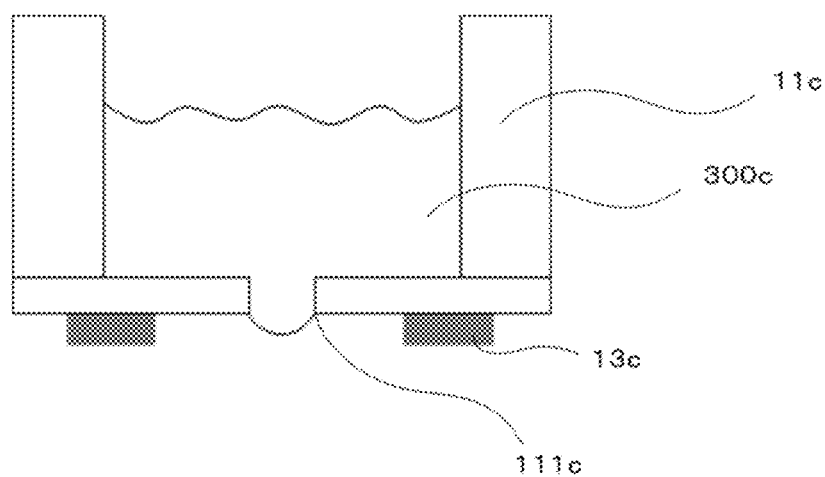
FIG. 6C is a schematic view of a modified example of the discharging head in a piezoelectric mode of FIG. 6B.

FIG. 6B is a schematic view illustrating one example of a discharging head in a piezoelectric mode. The discharging head in a piezoelectric mode has piezoelectric element 13b, liquid chamber 11b, cell suspension liquid 300b, and nozzle 111b.

For example, a single-cell printer from Cytena GmbH can be suitably used as the discharging head in a piezoelectric mode.

Although any of these discharging heads may be used, the pressure application mode using an electromagnetic valve cannot form liquid droplets repetitively at a high speed. Therefore, a piezoelectric mode is preferably used for enhancing the throughput of plate production. Furthermore, a problem of a general discharging head in a piezoelectric mode using piezoelectric element 13b may be uneven cell concentrations due to sedimentation, or nozzle clogging.

Hence, a more preferable configuration includes a configuration illustrated in FIG. 6C. FIG. 6C is a schematic view of a modified example of the discharging head in a piezoelectric mode using a piezoelectric element in FIG. 6B. The discharging head of FIG. 6C has piezoelectric element 13c, liquid chamber 11c, cell suspension liquid 300c, and nozzle 111c.

In the discharging head of FIG. 6C, a control apparatus (not illustrated) applies a voltage to the piezoelectric element 13c so that compressive stress can be generated in the lateral direction on the sheet of FIG. 6C to deform a membrane in the vertical direction on the sheet of FIG. 6C.

Examples of a mode other than the on-demand mode include a continuous mode of continuously forming liquid droplets. In the continuous mode, a piezoelectric element or a heater provides a fluctuation at regular intervals when liquid droplets are pushed out of a nozzle under pressure. As a result, tiny liquid droplets can be continuously created. It is further possible to choose between landing into filled sites (wells) or recovery into a recovery part by controlling liquid droplets during flying by applying a voltage in the direction of discharging. Such a mode is used in a cell sorter or a flow cytometer. For example, an apparatus under the name of cell sorter SH800 manufactured by Sony Corp. can be used.

Figure 7A:
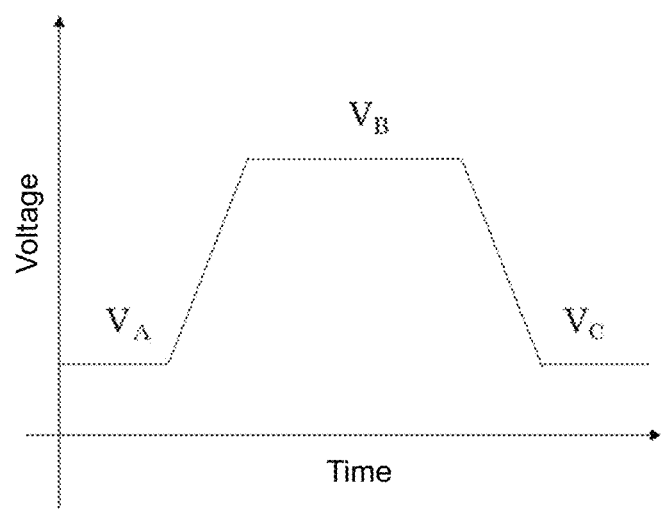
FIG. 7A is a schematic view illustrating one example of a voltage to be applied to a piezoelectric element.
Figure 7B:
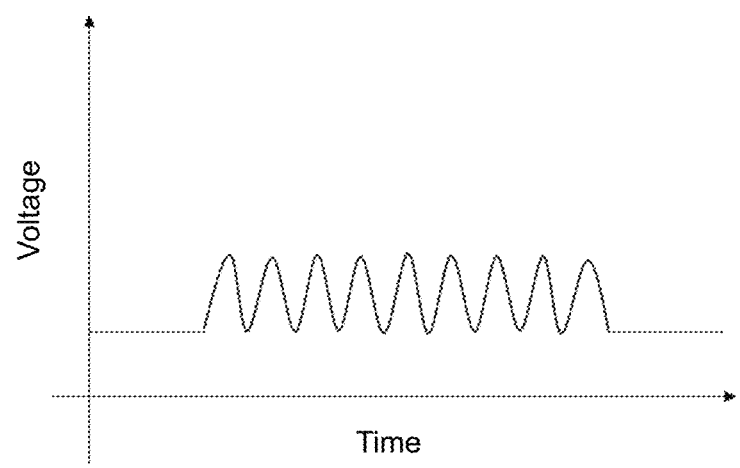
FIG. 7B is a schematic view illustrating another example of a voltage to be applied to a piezoelectric element.

FIG. 7A is a schematic view illustrating one example of a voltage to be applied to the piezoelectric element. FIG. 7B is a schematic view illustrating another example of a voltage to be applied to the piezoelectric element. FIG. 7A shows a driving voltage for forming liquid droplets. The liquid droplets can be formed depending on the amplitude of the voltage ($V_A$, $V_B$, and $V_C$). FIG. 7B shows a voltage for stirring the cell suspension liquid without discharging liquid droplets.

The cell suspension liquid in the liquid chamber can be stirred by inputting a plurality of pulses that are not so strong as to discharge liquid droplets, during a period when liquid droplets are not discharged. This can prevent concentration distribution ascribable to cell sedimentation.

The liquid droplet formation action of the discharging head that can be used in the present invention is described below.

Figure 8A:
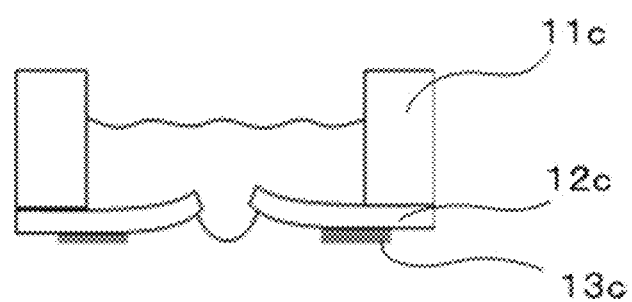
FIG. 8A is a schematic view illustrating one example of the state of a liquid droplet.
Figure 8B:
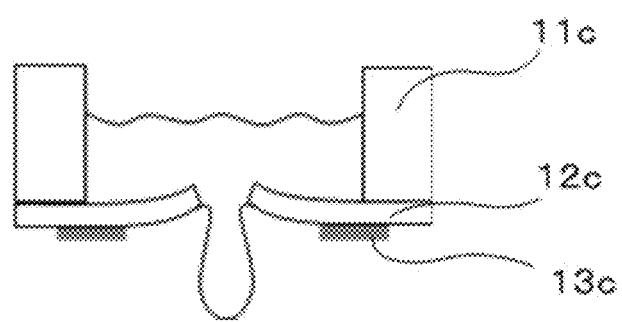
FIG. 8B is a schematic view illustrating one example of the state of a liquid droplet.
Figure 8C:
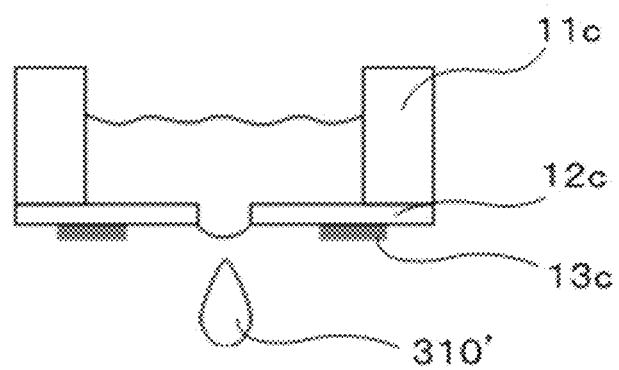
FIG. 8C is a schematic view illustrating one example of the state of a liquid droplet.

The discharging head applies a pulsed voltage to upper and lower electrodes formed in the piezoelectric element, and can thereby discharge liquid droplets. FIGS. 8A to 8C are schematic views illustrating the state of a liquid droplet at respective timings.

In FIG. 8A, first, membrane 12c is rapidly deformed by applying a voltage to piezoelectric element 13c so that high pressure occurs between the cell suspension liquid retained in liquid chamber 11c and the membrane 12c. Through this pressure, a liquid droplet is pushed out of a nozzle part.

Next, as illustrated in FIG. 8B, liquids are continuously pushed out of the nozzle part for the time to relax the pressure upward so that the liquid droplet grows.

Finally, as illustrated in FIG. 8C, liquid pressure drops in the vicinity of the interface between the cell suspension liquid and the membrane 12c when the membrane 12c is restored to its original state, to form liquid droplet 310'.

In the method for producing the device, a plate provided with filled sites (wells) is fixed onto a movable stage, and liquid droplets are sequentially landed into the depressions by combining the drive of the stage with liquid droplet formation from the discharging head. Here, the method of moving the plate is illustrated as moving the stage. As a matter of course, the discharge head may be moved.

The plate is not particularly limited, and a plate provided with filled sites (wells) which is generally used in the biotechnological field may be used.

The number of filled sites (wells) in the plate is not particularly limited and can be appropriately selected according to the purpose. One or more filled sites (wells) may be used.

Figure 9:
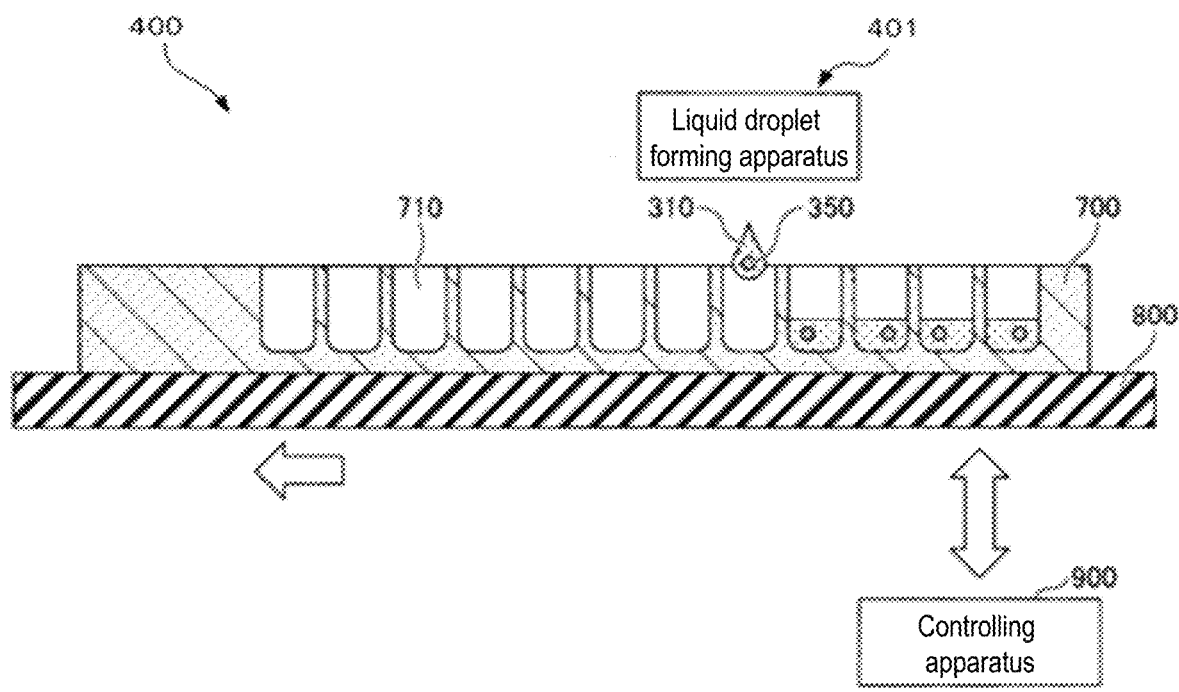
FIG. 9 is a schematic view illustrating one example of a dispensing apparatus for sequentially landing liquid droplets into wells.

FIG. 9 is a schematic view illustrating one example of dispensing apparatus 400 for sequentially landing liquid droplets into filled sites (wells) of a plate.

As illustrated in FIG. 9, the dispensing apparatus 400 for landing liquid droplets has liquid droplet forming apparatus 401, plate 700, stage 800, and controlling apparatus 900.

In the dispensing apparatus 400, the plate 700 is disposed on the stage 800 configured to be movable. The plate 700 is provided with a plurality of filled sites (wells) 710 (depressions) into which liquid droplets 310 discharged from a discharging head of the liquid droplet forming apparatus 401 are landed. The controlling apparatus 900 controls the relative positional relationship between the discharging head of the liquid droplet forming apparatus 401 and each of the filled sites (wells) 710 by moving the stage 800. Thus, the liquid droplets 310 containing fluorescently stained cells 350 can be sequentially discharged into the respective filled sites (wells) 710 from the discharging head of the liquid droplet forming apparatus 401.

The controlling apparatus 900 can be configured to comprise, for example, CPU, ROM, RAM, or a main memory. In this case, various functions of the controlling apparatus 900 can be achieved by the main memory which reads a program recorded in ROM or the like, and CPU which runs the program. However, the controlling apparatus 900 may be partially or wholly achieved only by a hardware. The controlling apparatus 900 may be physically constituted by a plurality of apparatuses, etc.

It is preferred for the liquid droplets to be discharged to land the liquid droplets into filled sites (wells) so as to obtain a plurality of levels when the cell suspension liquid is landed into the filled sites (wells).

The plurality of levels mean a plurality of references serving as a standard. It is preferred for the plurality of levels that a plurality of cells having a specific nucleic acid should have a predetermined concentration gradient in filled sites (wells). Such cells having the concentration gradient can be suitably used as a reagent for calibration curves. The plurality of levels can be controlled using values counted in a sensor.

For example, a 1-well microtube, an 8-strip tube, or a 96-well or 384-well filled site (well) plate is preferably used as the plate. In the case of a plurality of filled sites (wells), the cells may be dispensed at the same number to these filled sites (wells) in the plate, or may be placed therein at different levels of numbers. Also, cell-free filled sites (wells) may exist. For example, it is possible to prepare a plate in which the cells (or the nucleic acid) are dispensed at 7 levels of about 1, 2, 4, 8, 16, 32, and 64.

<<Cell Counting Step>>

The cell counting step is the step of counting the cells contained in the liquid droplets using a sensor after discharging the liquid droplets and before landing the liquid droplets into filled sites (wells).

The sensor means an apparatus that replaces or the mechanical, electromagnetic, thermal, acoustic, or chemical properties of a natural phenomenon or an artificial material, or spatial or temporal information indicated thereby with signals of another medium easily handleable by humans or machines, through the application of some scientific principle.

The counting means the determination of the number.

The cell counting step is not particularly limited and can be appropriately selected according to the purpose, as long as the cells contained in the liquid droplets are counted using a sensor after discharging the liquid droplets and before landing the liquid droplets into filled sites (wells). The cell counting step may comprise treatment of observing the cells before the discharge, or treatment of counting the cells after the landing.

For counting the cells contained in the liquid droplets after discharging the liquid droplets and before landing the liquid droplets into filled sites (wells), it is preferred to observe the cells in the liquid droplets at a timing when the liquid droplets are positioned immediately above filled site (well) openings where the liquid droplets are predicted to reliably enter the filled sites (wells) of the plate.

Examples of the method for observing the cells in the liquid droplets include an optical detection method and an electric or magnetic detection method.

—Optical Detection Method—

Figure 10:
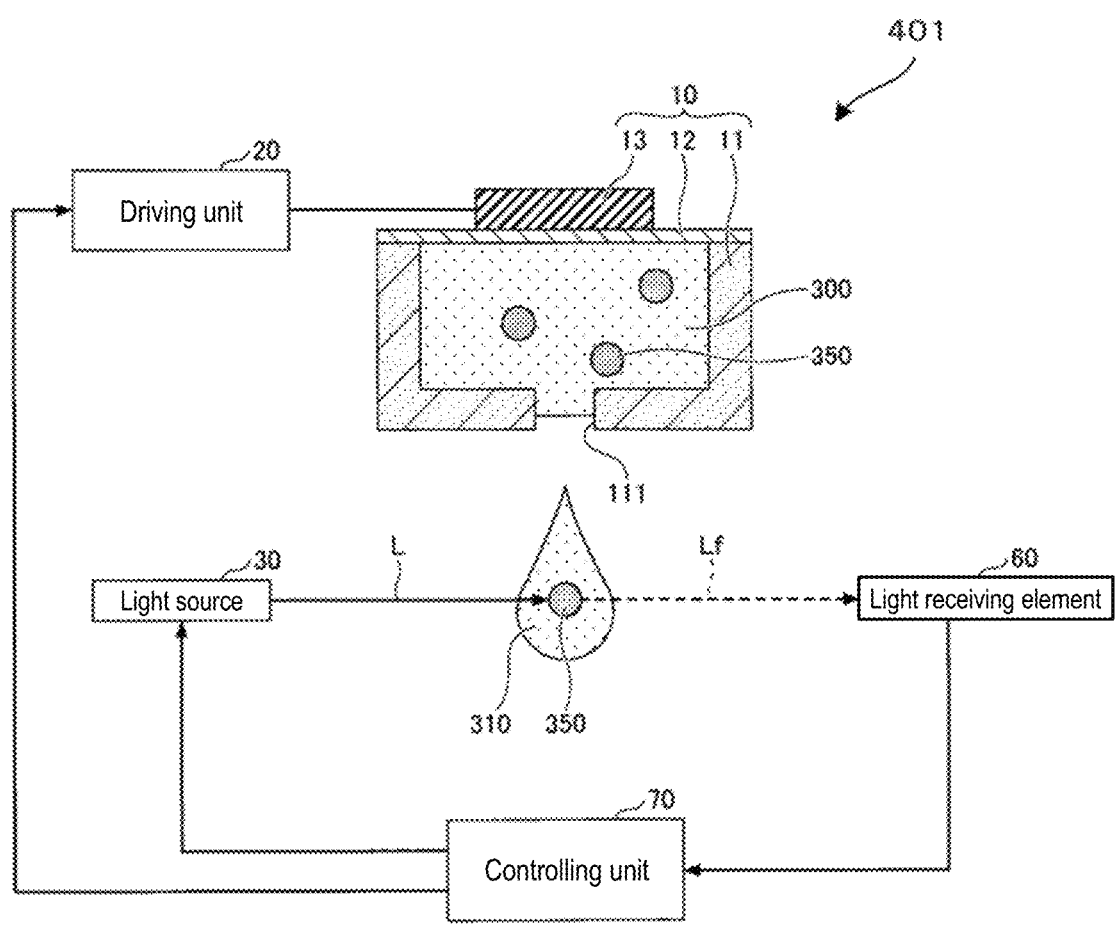
FIG. 10 is a schematic view illustrating one example of a liquid droplet forming apparatus.
Figure 14:
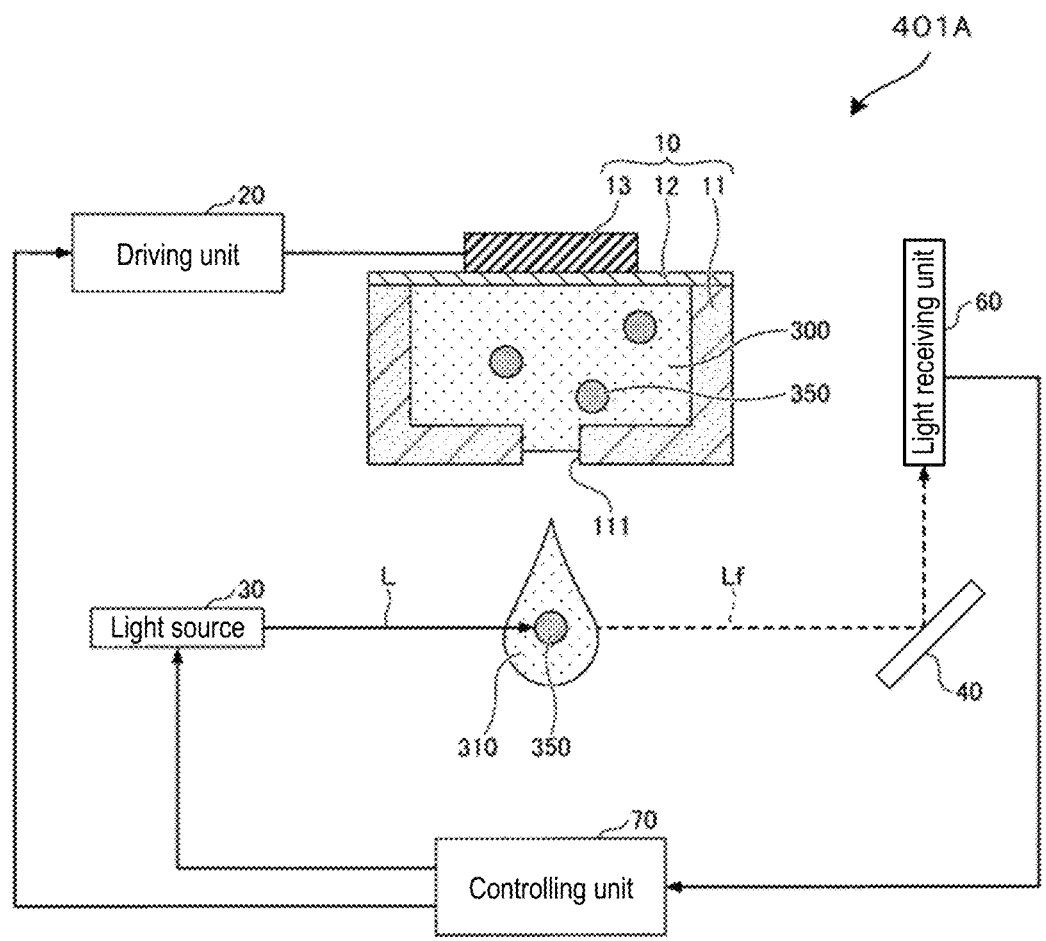
FIG. 14 is a schematic view illustrating a modified example of the liquid droplet forming apparatus.
Figure 15:
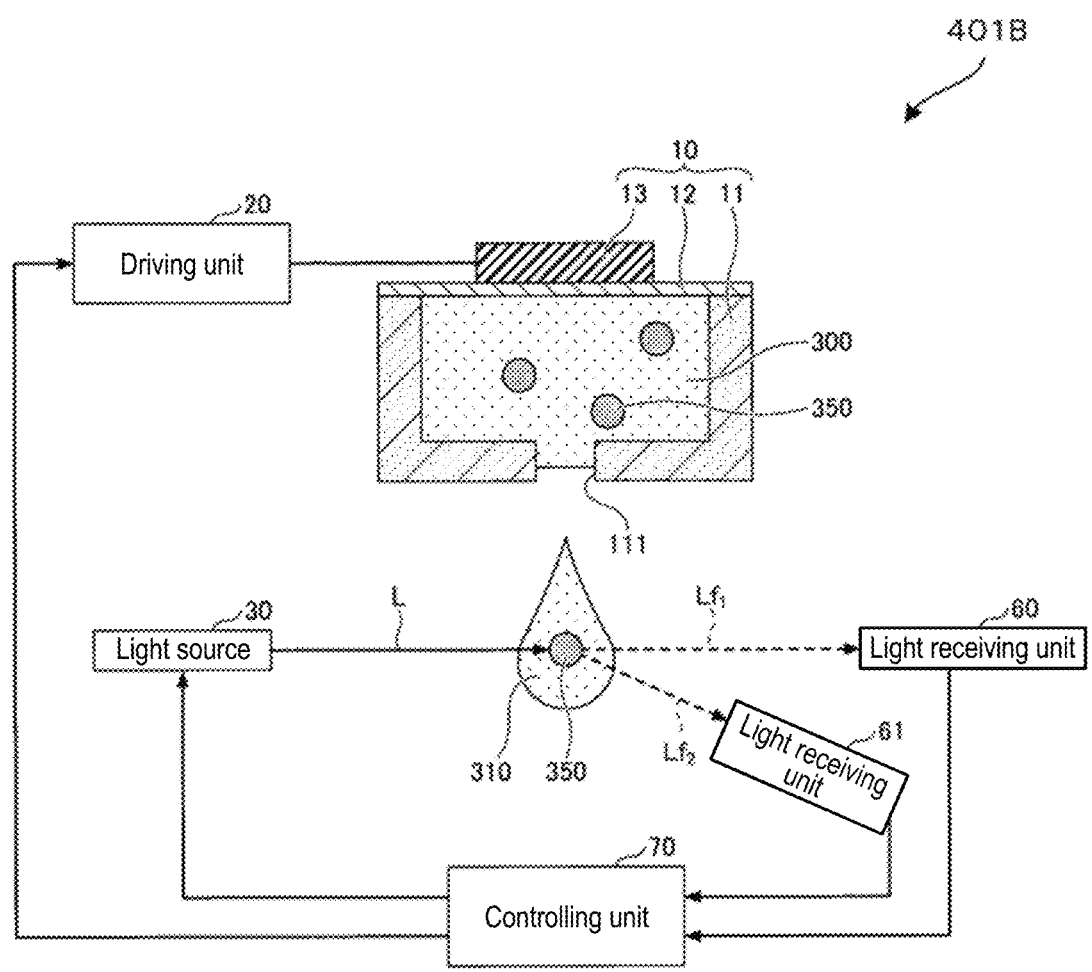
FIG. 15 is a schematic view illustrating another modified example of the liquid droplet forming apparatus.

The optical detection method is described below with reference to FIGS. 10, 14, and 15. FIG. 10 is a schematic view illustrating one example of liquid droplet forming apparatus 401. FIGS. 14 and 15 are schematic views illustrating another example of the liquid droplet forming apparatus (401A and 401B, respectively). As illustrated in FIG. 10, the liquid droplet forming apparatus 401 has a discharging head (liquid droplet discharging unit) 10, driving unit 20, light source 30, light receiving element 60, and controlling unit 70.

In FIG. 10, a liquid obtained by fluorescently staining cells with a specific dye and then dispersing the cells in a predetermined solution is used as a cell suspension liquid. Liquid droplets formed from the discharging head are irradiated with light having a specific wavelength emitted from the light source, and fluorescence emitted by the cells is detected by the light receiving element to count the cells. In this respect, a method of staining cells with a fluorescent dye as well as autofluorescence emitted by a molecule originally contained in the cells may be utilized, or the cells may be caused to emit fluorescence by introducing a gene for fluorescent protein (e.g., GFP (green fluorescent protein)) production to the cells in advance.

The irradiation with light means that exposure to light.

The discharging head 10 has liquid chamber 11, membrane 12, and driving element 13, and can discharge cell suspension liquid 300 containing fluorescently stained cells 350 suspended therein, as liquid droplets.

The liquid chamber 11 is a liquid reservoir that retains the cell suspension liquid 300 containing the fluorescently stained cells 350 suspended therein, and is provided on the underside with nozzle 111, which is a through-hole. The liquid chamber 11 can be formed from, for example, a metal, silicon, or ceramic. Examples of the fluorescently stained cells 350 include inorganic fine particles and organic polymer particles stained with a fluorescent dye.

The membrane 12 is a membranous member fixed to the upper end portion of the liquid chamber 11. The planar shape of the membrane 12 can be round, for example, and may be oval or quadrangular, for example.

The driving element 13 is provided on the top side of the membrane 12. The shape of the driving element 13 can be designed according to the shape of the membrane 12. For example, round driving element 13 is preferably provided when the planar shape of the membrane 12 is round.

The membrane 12 can be vibrated by supplying driving signals from the driving unit 20 to the driving element 13. The vibration of the membrane 12 allows the nozzle 111 to discharge liquid droplets 310 containing the fluorescently stained cells 350.

In the case of using a piezoelectric element as the driving element 13, this driving element can have, for example, a structure provided on the upper and lower faces of a piezoelectric material with electrodes for voltage application. In this case, the driving unit 20 applies a voltage to between the upper and lower electrodes of the piezoelectric element so that compressive stress can be generated in the lateral direction on the sheet of FIG. 10 to vibrate the membrane 12 in the vertical direction on the sheet of FIG. 10. For example, lead zirconate titanate (PZT) can be used as the piezoelectric material. In addition, various piezoelectric materials can be used, such as bismuth iron oxide, metal niobite, barium titanate, and these materials supplemented with a metal or a distinctive oxide.

The light source 30 irradiates the liquid droplets 310 during flying with light L. The term "during flying" means a state from the discharge of the liquid droplet 310 from the liquid droplet discharging unit 10 to its landing to a landing target. The liquid droplet 310 during flying is substantially spherical at an irradiation position with the light L. The beam shape of the light L is a substantially circular shape.

In this context, the beam diameter of the light L is preferably on the order of 10 times to 100 times the diameter of the liquid droplet 310. This is because the liquid droplets 310 are reliably irradiated with the light L from the light source 30 even if the liquid droplets 310 are present at varying positions.

However, it is not preferred that the beam diameter of the light L should go significantly beyond 100 times the diameter of the liquid droplet 310. This is because, since the energy density of the light for the irradiation of the liquid droplets 310 is decreased, fluorescence Lf emitted with the light L as excitation light is decreased, and difficult to be detected by the light receiving element 60.

The light L to be emitted from the light source 30 is preferably pulsed light. For example, solid-state laser, semiconductor laser, or dye laser is suitably used. When the light L is pulsed light, its pulse width is preferably 10 μs or less, more preferably 1 μs or less. The energy per unit pulse depends largely on an optical system such as the presence or absence of light collection, and is generally preferably 0.1 μJ or larger, more preferably 1 μJ or larger.

The light receiving element 60 receives fluorescence Lf emitted from the fluorescently stained cells 350 absorbing the light L as excitation light, when the liquid droplets 310 during flying contain the fluorescently stained cells 350. The fluorescence Lf is emitted in all directions from the fluorescently stained cells 350. Therefore, the light receiving element 60 can be disposed at any position that permits reception of the fluorescence Lf. In this respect, for improving contrast, it is preferred to dispose the light receiving element 60 at a position upon which the outgoing light L from the light source 30 is not directly incident.

The light receiving element 60 is not particularly limited and can be appropriately selected according to the purpose, as long as the element can receive fluorescence Lf emitted from the fluorescently stained cells 350. The light receiving element is preferably an optical sensor that irradiates light having a specific wavelength and receives fluorescence from cells in liquid droplets. Examples of the light receiving element 60 include one-dimensional elements such as photodiodes and photosensors. A photomultiplier tube or an avalanche photodiode is preferably used when highly sensitive measurement is necessary. For example, a two-dimensional element such as CCD (charge coupled device), CMOS (complementary metal oxide semiconductor), or gate CCD may be used as the light receiving element 60.

Since the fluorescence Lf emitted by the fluorescently stained cells 350 is weaker than the light L emitted by the light source 30, a filter that attenuates the wavelength region of the light L may be established at a stage prior to the light receiving element 60 (on the light receiving face side). Thus, an image of the fluorescently stained cells 350 with very high contrast can be obtained in the light receiving element 60. For example, a notch filter that attenuates a specific wavelength region including the wavelength of the light L can be used as the filter.

As mentioned above, the light L emitted from the light source 30 is preferably pulsed light. The light L emitted from the light source 30 may be continuously oscillated light. In this case, the light receiving element 60 is preferably controlled so as to be capable of taking up light at a timing when the liquid droplets 310 during flying are irradiated with the continuously oscillated light, and thereby receives fluorescence Lf.

The controlling unit 70 has a function of controlling the driving unit 20 and the light source 30. The controlling unit 70 also has a function of obtaining information based on the quantity of light received by the light receiving element 60, and counting the fluorescently stained cells 350 (also including the case of being zero) contained in the liquid droplets 310. Hereinafter, the action of the liquid droplet forming apparatus 401 including the action of the controlling unit 70 is described with reference to FIGS. 11 to 16.

Figure 11:
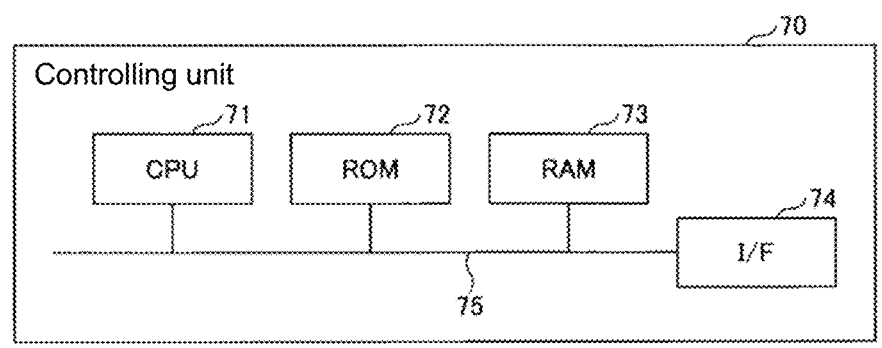
FIG. 11 is a diagram illustrating a hardware block of a controlling unit in the liquid droplet forming apparatus of FIG. 10.
Figure 12:
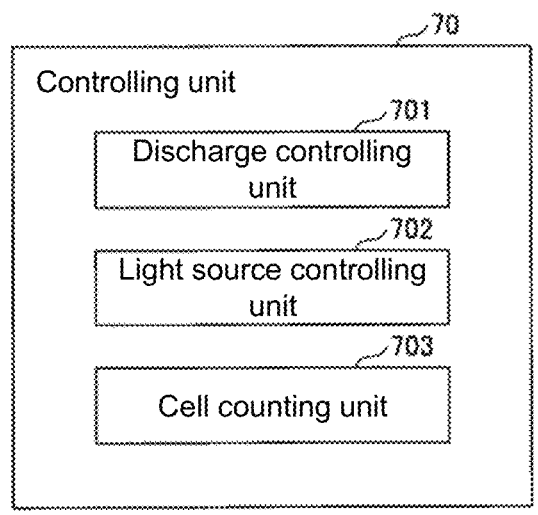
FIG. 12 is a diagram illustrating a functional block of the controlling unit in the liquid droplet forming apparatus of FIG. 10.
Figure 13:
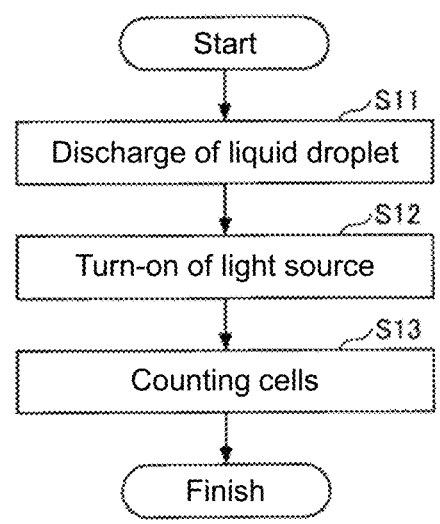
FIG. 13 is a flow chart illustrating one example of the action of the liquid droplet forming apparatus.

FIG. 11 is a diagram illustrating a hardware block of the controlling unit in the liquid droplet forming apparatus of FIG. 10. FIG. 12 is a diagram illustrating a functional block of the controlling unit in the liquid droplet forming apparatus of FIG. 10. FIG. 13 is a flow chart illustrating one example of the action of the liquid droplet forming apparatus.

As illustrated in FIG. 11, the controlling unit 70 has CPU 71, ROM 72, RAM 73, I/F 74, and bus line 75. The CPU 71, the ROM 72, the RAM 73, and the I/F 74 are mutually connected via the bus line 75.

The CPU 71 controls each function of the controlling unit 70. The ROM 72, which is a storage unit, stores a program that is run by the CPU 71 to control each function of the controlling unit 70, and various pieces of information. The RAM 73, which is a storage unit, is used as the work area or the like of the CPU 71. The RAM 73 can also temporarily store predetermined information. The I/F 74 is an interface for connecting the liquid droplet forming apparatus 401 to an additional instrument or the like. The liquid droplet forming apparatus 401 may be connected to an external network or the like via the I/F 74.

As illustrated in FIG. 12, the controlling unit 70 has discharge controlling unit 701, light source controlling unit 702, and cell counting unit (cell number sensing unit) 703 as functional blocks.

The cell (particle) counting of the liquid droplet forming apparatus 401 is described with reference to FIGS. 12 and 13. First, in step S11, the discharge controlling unit 701 of the controlling unit 70 issues a command of discharge to the driving unit 20. The driving unit 20 that has received the command of discharge from the discharge controlling unit 701 supplies driving signals to the driving element 13 to vibrate the membrane 12. The vibration of the membrane 12 allows the nozzle 111 to discharge the liquid droplets 310 containing the fluorescently stained cells 350.

Next, in step S12, the light source controlling unit 702 of the controlling unit 70 issues a command of turn-on to the light source 30 in synchronization with the discharge of the liquid droplets 310 (in synchronization with the driving signals supplied from the driving unit 20 to the liquid droplet discharging unit 10). Thus, the light source 30 is turned on so that the liquid droplets 310 during flying are irradiated with light L.

In this context, the synchronization does not mean that the light source emits light at the same time with the discharge of the liquid droplets 310 by the liquid droplet discharging unit 10 (at the same time with the supply of the driving signals to the liquid droplet discharging unit 10 by the driving unit 20), but means that the light source 30 emits light at a timing when the liquid droplets 310 are irradiated with light L after the flying liquid droplets 310 arrive at a predetermined position. In other words, the light source controlling unit 702 controls the light source 30 so as to emit light after a delay of a predetermined time with respect to the discharge of the liquid droplets 310 by the liquid droplet discharging unit 10 (the supply of the driving signals from the driving unit 20 to the liquid droplet discharging unit 10).

For example, velocity v of the liquid droplet 310 to be discharged upon supply of driving signals to the liquid droplet discharging unit 10 is measured in advance. Then, time t of the discharged liquid droplet 310 to reach a predetermined position is calculated based on the measured velocity v. The timing of light irradiation from the light source 30 is delayed by t with respect to the timing of supply of the driving signals to the liquid droplet discharging unit 10. This enables light emission to be controlled favorably, and allows the liquid droplets 310 to be reliably irradiated with light from the light source 30.

Next, in step S13, the cell counting unit 703 of the controlling unit 70 counts the fluorescently stained cells 350 (also including the case of being zero) contained in the liquid droplets 310 based on information from the light receiving element 60. In this context, the information from the light receiving element 60 is the luminance value (quantity of light) or area value of the fluorescently stained cells 350.

The cell counting unit 703 can count the fluorescently stained cells 350, for example, by comparing the quantity of light received in the light receiving element 60 with a preset threshold. In this case, a one-dimensional element or a two-dimensional element may be used as the light receiving element 60.

In the case of using a two-dimensional element as the light receiving element 60, the cell counting unit 703 may employ an approach of performing image processing for calculating the luminance value or area of the fluorescently stained cells 350 based on a two-dimensional image obtained from the light receiving element 60. In this case, the cell counting unit 703 can count the fluorescently stained cells 350 by calculating the luminance value or area value of the fluorescently stained cells 350 through image processing, and comparing the calculated luminance value or area value with a preset threshold.

The fluorescently stained cells 350 may be cells or stained cells. The stained cells mean cells stained with a fluorescent dye, or cells capable of expressing a fluorescent protein.

The fluorescent dye for the stained cells is not particularly limited and can be appropriately selected according to the purpose. Examples thereof include fluoresceins, rhodamines, coumarins, pyrenes, cyanines, and azos. These fluorescent dyes may be used alone or may be used in combination of two or more thereof. Among them, eosin, Evans blue, trypan blue, rhodamine 6G, rhodamine B, or rhodamine 123 is more preferred.

Examples of the fluorescent protein include Sirius, EBFP, ECFP, mTurquoise, TagCFP, AmCyan, mTFP1, Midoriishi-Cyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. These fluorescent proteins may be used alone or may be used in combination of two or more thereof.

Thus, in the liquid droplet forming apparatus 401, the driving unit 20 supplies driving signals to the liquid droplet discharging unit 10 which retains cell suspension liquid 300 containing fluorescently stained cells 350 suspended therein, to discharge liquid droplets 310 containing the fluorescently stained cells 350, and the liquid droplets 310 during flying are irradiated with light L from the light source 30. Then, the fluorescently stained cells 350 contained in the flying liquid droplets 310 emit fluorescence Lf with the light L as excitation light, and the light receiving element 60 receives the fluorescence Lf. The cell counting unit 703 further counts the fluorescently stained cells 350 contained in the flying liquid droplets 310, based on information from the light receiving element 60.

In other words, in the liquid droplet forming apparatus 401, the number of the fluorescently stained cells 350 contained in the flying liquid droplets 310 is actually observed on the spot. This can improve the counting accuracy of the fluorescently stained cells 350 than ever. Since the fluorescently stained cells 350 contained in the flying liquid droplets 310 is irradiated with fluorescence Lf to emit light L and light L is received by the light receiving element 60, an image of the fluorescently stained cells 350 can be obtained with high contrast. This can reduce the frequency of occurrence of miscounting of the fluorescently stained cells 350.

FIG. 14 is a schematic view illustrating a modified example of the liquid droplet forming apparatus 401 of FIG. 10. As illustrated in FIG. 14, liquid droplet forming apparatus 401A differs from the liquid droplet forming apparatus 401 (see FIG. 10) in that mirror 40 is disposed at a stage prior to the light receiving element 60. Description may be omitted about the same component parts as those of the already described embodiments.

Thus, in the liquid droplet forming apparatus 401A, the mirror 40 disposed at a stage prior to the light receiving element 60 can improve the degree of freedom of layout of the light receiving element 60.

For example, the layout of FIG. 10 might cause the interference between a target to be landed and the optical system (particularly, the light receiving element 60) of the liquid droplet forming apparatus 401 when the nozzle 111 is brought close to the target to be landed. On the other hand, the layout of FIG. 14 can avoid causing the interference.

As illustrated in FIG. 14, the changed layout of the light receiving element 60 can reduce the gap between the target to be landed into which the liquid droplets 310 are landed, and the nozzle 111, and can prevent variations of a droplet landed position. As a result, the accuracy of dispensing can be improved.

FIG. 15 is a schematic view illustrating another modified example of the liquid droplet forming apparatus 401 of FIG. 10. As illustrated in FIG. 15, liquid droplet forming apparatus 401B differs from the liquid droplet forming apparatus 401 (see FIG. 10) in that light receiving element 61 which receives fluorescence $Lf_2$ emitted from the fluorescently stained cells 350 is provided in addition to light receiving element 60 which receives fluorescence $Lf_1$ emitted from the fluorescently stained cells 350. Description may be omitted about the same or similar component parts as those of the already described embodiments.

In this context, the fluorescence $Lf_1$ or $Lf_2$ refers to a portion of fluorescence emitted in all directions from the fluorescently stained cells 350. The light receiving elements 60 and 61 can be disposed at any positions that permit reception of fluorescence emitted in different directions from the fluorescently stained cells 350. Three or more light receiving elements may be disposed at positions that permit reception of fluorescence emitted in different directions from the fluorescently stained cells 350. The respective light receiving elements may have the same specifications or may have different specifications.

In the case of using a single light receiving element, the cell counting unit 703 might miscount (cause a counting error) the fluorescently stained cells 350 contained in the liquid droplets 310, due to the overlap of the fluorescently stained cells 350 when the flying liquid droplet 310 contains a plurality of fluorescently stained cells 350.

Figure 16A:
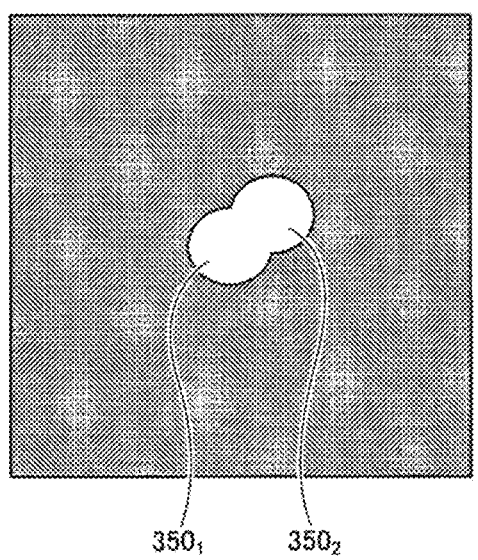
FIG. 16A is a diagram illustrating the case where a flying liquid droplet contains two fluorescent particles.
Figure 16B:
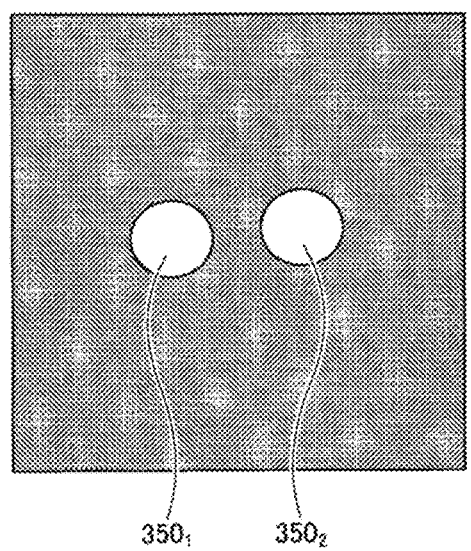
FIG. 16B is a diagram illustrating the case where a flying liquid droplet contains two fluorescent particles.

FIGS. 16A and 16B are diagrams illustrating the case where a flying liquid droplet contains two fluorescently stained cells. For example, fluorescently stained cells $350_1$ and $350_2$ may overlap with each other as illustrated in FIG. 16A, while the fluorescently stained cells $350_1$ and $350_2$ may not overlap with each other as illustrated in FIG. 16B. The provision of two or more light receiving elements can reduce the influence of overlapping fluorescently stained cells.

As mentioned above, the cell counting unit 703 can count fluorescent particles by calculating the luminance value or area value of the fluorescent particles through image processing, and comparing the calculated luminance value or area value with a preset threshold.

In the case of setting two or more light receiving elements, a counting error can be prevented by adopting data that exhibits the largest value among the luminance values or area values obtained from the respective light receiving elements. This is described in more detail with reference to FIG. 17.

Figure 17:
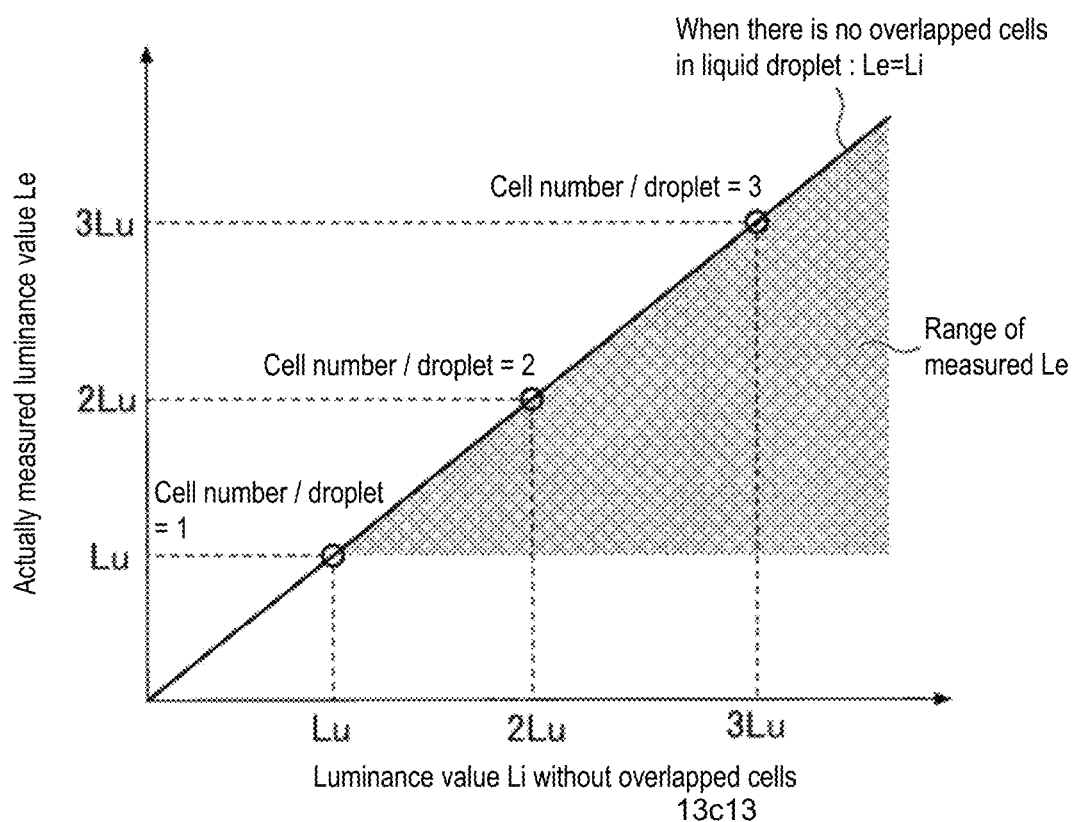
FIG. 17 is a diagram illustrating the relationship between luminance value Li and actually measured luminance value Le without particle overlapping.

FIG. 17 is a diagram illustrating the relationship between luminance value Li and actually measured luminance value Le without overlapping of particles. As illustrated in FIG. 17, Le=Li holds without overlapping of particles in the liquid droplet. For example, when the luminance value of one cell is defined as Lu, Le=Lu holds at cell number/droplet=1, and Le=nLu (n: natural number) holds at particle number/droplet=n.

However, in actual, the particles may overlap with each other when n is 2 or larger. Therefore, the actually measured luminance value is Lu≤Le≤nLu (shaded area of FIG. 16A). Accordingly, for example, the threshold can be set to (nLu−Lu/2)≤threshold<(nLu+Lu/2) at cell number/droplet=n. In the case of setting a plurality of light receiving elements, a counting error can be prevented by adopting data that exhibits the largest value among those obtained from the respective light receiving elements. An area value may be used instead of the luminance value.

In the case of setting a plurality of light receiving elements, the particle number may be determined using an algorithm for estimating a cell number based on plural pieces of obtained shape data.

Thus, the liquid droplet forming apparatus 401B has a plurality of light receiving elements which receive fluorescence emitted in different directions by the fluorescently stained cells 350, and can therefore further reduce the frequency of occurrence of miscounting of the fluorescently stained cells 350.

Figure 18:
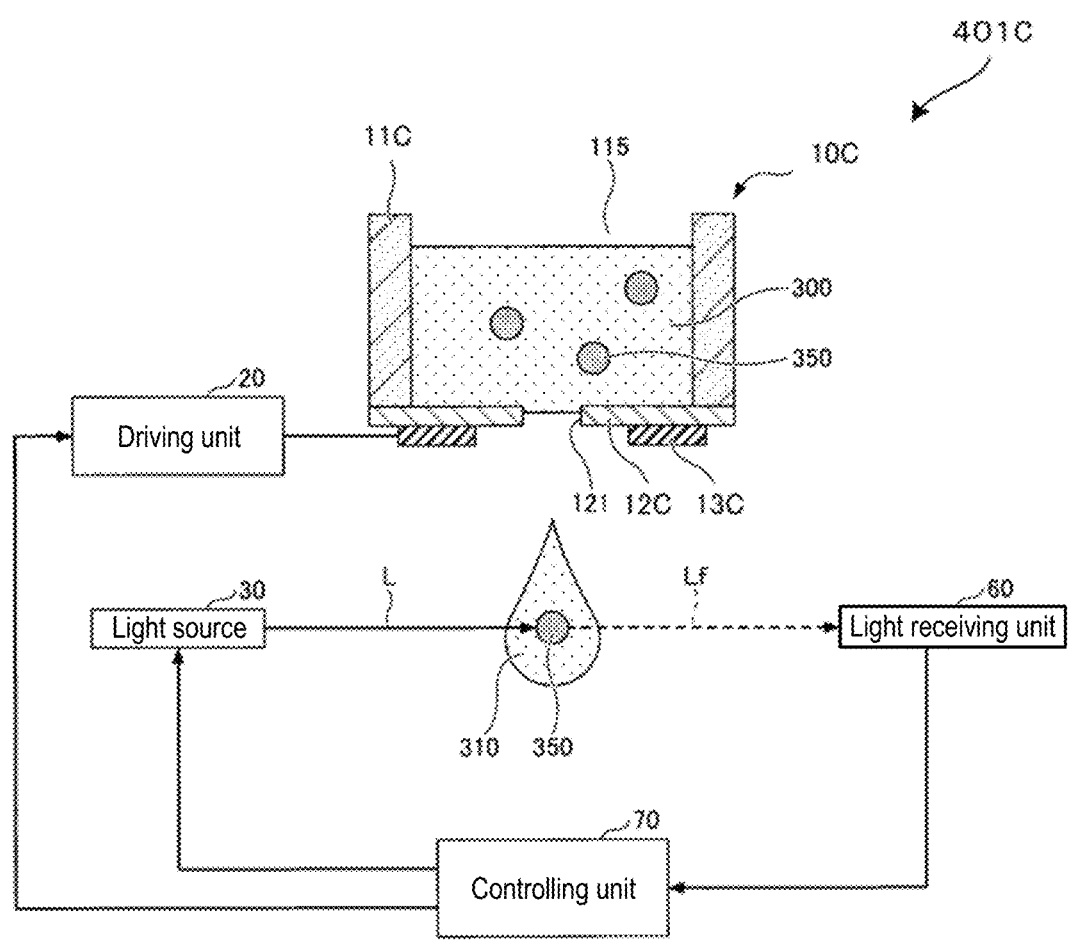
FIG. 18 is a schematic view illustrating an alternative modified example of the liquid droplet forming apparatus.

FIG. 18 is a schematic view illustrating an alternative modified example of the liquid droplet forming apparatus 401 of FIG. 10. As illustrated in FIG. 18, liquid droplet forming apparatus 401C differs from the liquid droplet forming apparatus 401 (see FIG. 10) in that the liquid droplet discharging unit 10 is replaced with liquid droplet discharging unit 10C. Description may be omitted about the same component parts as those of the already described embodiments.

The liquid droplet discharging unit 10C has liquid chamber 11C, membrane 12C, and driving element 13C. The liquid chamber 11C has, in its upper portion, atmospheric relieving part 115 which renders the inside of the liquid chamber 11C open to the atmosphere, and is configured so as to be capable of ejecting air bubbles mixed into the cell suspension liquid 300 from the atmospheric relieving part 115.

The membrane 12C is a membranous member fixed to the lower end portion of the liquid chamber 11C. Nozzle 121, which is a through-hole, is formed at substantially the center of the membrane 12C. The cell suspension liquid 300 retained in the liquid chamber 11C is discharged as liquid droplets 310 from the nozzle 121 by the vibration of the membrane 12C. Since the liquid droplets 310 are formed through the inertia of the vibration of the membrane 12C, even the cell suspension liquid 300 having high surface tension (high viscosity) can be discharged. The planar shape of the membrane 12C can be round, for example, and may be oval or quadrangular, for example.

The material of the membrane 12C is not particularly limited. When the material is too soft, the membrane 12C is easily vibrated, and thus it is difficult to suppress the vibration immediately in the absence of discharge. It is therefore preferred to use a material having hardness to some extent. For example, a metal material, a ceramic material, or a polymer material having hardness to some extent can be used as the material of the membrane 12C.

Particularly, when cells are used as the fluorescently stained cells 350, the material is preferably low adhesive to the cells or proteins. In general, the adhesiveness to cells is said to depend on the contact angle between the material and water, and a highly hydrophilic or highly hydrophobic material is low adhesive to cells. Various metal materials or ceramic (metal oxide) may be used as the highly hydrophilic material. Fluororesin or the like may be used as the highly hydrophobic material.

Other examples of such a material can include stainless steel, nickel, aluminum, silicon dioxide, alumina, and zirconia. In addition, it is also possible to reduce the adhesiveness to cells by coating the material surface. For example, the material surface may be coated with the aforementioned metal or metal oxide material, or may be coated with a synthetic phospho lipid polymer (e.g., manufactured by NOF Corp., Lipidure) that mimics a cell membrane.

The nozzle 121 is preferably formed as a substantially true circular through-hole at substantially the center of the membrane 12C. In this case, the diameter of the nozzle 121 is not particularly limited and is preferably 2 or more times the size of the fluorescently stained cells 350 in order to avoid clogging the nozzle 121 with the fluorescently stained cells 350. When the fluorescently stained cells 350 are, for example, animal cells, particularly, human cells, the diameter of the nozzle 121 is preferably 10 µm or larger, more preferably 100 µm or larger, according to the cells used, since the size of the human cells is generally on the order of 5 µm to 50 µm.

On the other hand, when liquid droplets are too large, it is difficult to achieve the purpose of forming tiny liquid droplets. Therefore, the diameter of the nozzle 121 is preferably 200 µm or smaller. In other words, the diameter of the nozzle 121 in the liquid droplet discharging unit 10C is typically in the range of 10 µm to 200 µm.

The driving element 13C is formed on the underside of the membrane 12C. The shape of the driving element 13C can be designed depending on the shape of the membrane 12C. For example, driving element 13C having a ring-like planar shape is preferably formed around the nozzle 121 when the planar shape of the membrane 12C is round. The driving mode of the driving element 13C can be similar to that of the driving element 13.

The driving unit 20 can selectively (e.g., alternately) impart, to the driving element 13C, a discharge waveform for vibrating the membrane 12C to form the liquid droplets 310, and a stirring waveform for vibrating the membrane 12C without forming the liquid droplets 310.

For example, formation of the liquid droplets 310 by applying the stirring waveform can be prevented by shaping both the discharge waveform and the stirring waveform into a rectangular wave, and lowering the driving voltage of the discharge waveform than that of the stirring waveform. In other words, the vibrated state (degree of vibration) of the membrane 12C can be controlled by the amplitude of the driving voltage.

In the liquid droplet discharging unit 10C, the driving element 13C is formed on the underside of the membrane 12C. Therefore, the vibration of the membrane 12C by the driving element 13C enables a flow to be generated in a direction from the lower portion to the upper portion of the liquid chamber 11C.

At this time, the motion of the fluorescently stained cells 350 is a motion from the bottom to the top so that a convection flow occurs within the liquid chamber 11C to stir the cell suspension liquid 300 containing the fluorescently stained cells 350. The flow in the direction from the lower portion to the upper portion of the liquid chamber 11C uniformly disperses the sedimented and aggregated fluorescently stained cells 350 inside the liquid chamber 11C.

In other words, the driving unit 20 allows the nozzle 121 to discharge the cell suspension liquid 300 retained in the liquid chamber 11C as the liquid droplets 310, by applying the discharge waveform to the driving element 13C, and controlling the vibrated state of the membrane 12C. The driving unit 20 can also stir the cell suspension liquid 300 retained in the liquid chamber 11C, by applying the stirring waveform to the driving element 13C, and controlling the vibrated state of the membrane 12C. No liquid droplet 310 is discharged from the nozzle 121 during stirring.

Thus, the fluorescently stained cells 350 can be prevented from being sedimented and aggregated on the membrane 12C, and can be evenly dispersed into the cell suspension liquid 300, by stirring the cell suspension liquid 300 during when no liquid droplet 310 is formed. This can prevent the nozzle 121 from being clogged, and the number of the fluorescently stained cells 350 in the discharged liquid droplets 310 from varying. As a result, the cell suspension liquid 300 containing the fluorescently stained cells 350 can be discharged as the liquid droplets 310 continuously for a long time and stably.

In the liquid droplet forming apparatus 401C, air bubbles may be mixed into the cell suspension liquid 300 within the liquid chamber 11C. In this case as well, the liquid droplet forming apparatus 401C can eject air bubbles mixed into the cell suspension liquid 300 to the outside air through the atmospheric relieving part 115, since the atmospheric relieving part 115 is provided in the upper portion of the liquid chamber 11C. This enables the liquid droplets 310 to be formed continuously and stably without discarding a large amount of liquid for air bubble ejection.

Specifically, when air bubbles are mixed into the vicinity of the nozzle 121, or a large number of air bubbles is mixed onto the membrane 12C, they influence the discharged state. Therefore, the stable formation of liquid droplets for a long time requires ejecting air bubbles thus mixed. Usually, the air bubbles mixed onto the membrane 12C move upward either spontaneously or by the vibration of the membrane 12C. The atmospheric relieving part 115 is provided in the liquid chamber 11C and is therefore capable of ejecting the mixed air bubbles. Hence, discharge failure can be prevented even if air bubbles are mixed onto the liquid chamber 11C. Thus, the liquid droplets 310 can be formed continuously and stably.

Air bubbles may be actively allowed to move upward in the liquid chamber 11C, by vibrating the membrane 12C, at a timing when no liquid droplet is formed, without forming liquid droplets.

—Electric or Magnetic Detection Method—

Figure 19:
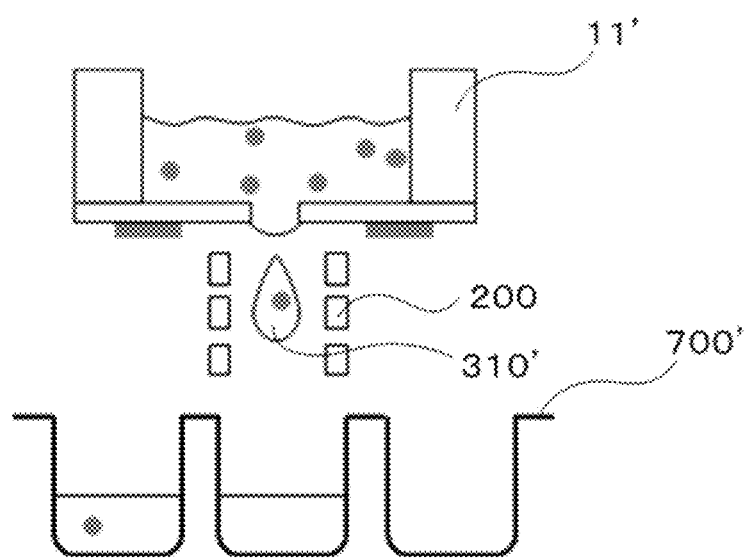
FIG. 19 is a schematic view illustrating another example of the liquid droplet forming apparatus.

For the electric or magnetic detection method, as illustrated in FIG. 19, coil 200 for cell counting is established as a sensor immediately below a discharging head which discharges a cell suspension liquid as liquid droplets 310' from liquid chamber 11' to plate 700'. The cells may be modified with a specific protein, and covered with magnetic beads capable of adhering to the cells. Thus, the presence or absence of the cells in flying liquid droplets can be detected based on induced current that occurs while the cells attached to the magnetic beads pass through the coil. In general, cells have a protein unique to the cells on their surface. The magnetic beads are modified with an antibody capable of binding to this protein, and can thereby be attached to the cells. A ready-made article may be used as such magnetic beads. For example, Dynabeads(R) manufactured by VERITAS Corp. are available.

[Treatment of Observing Cell Before Discharge]

Figure 20:
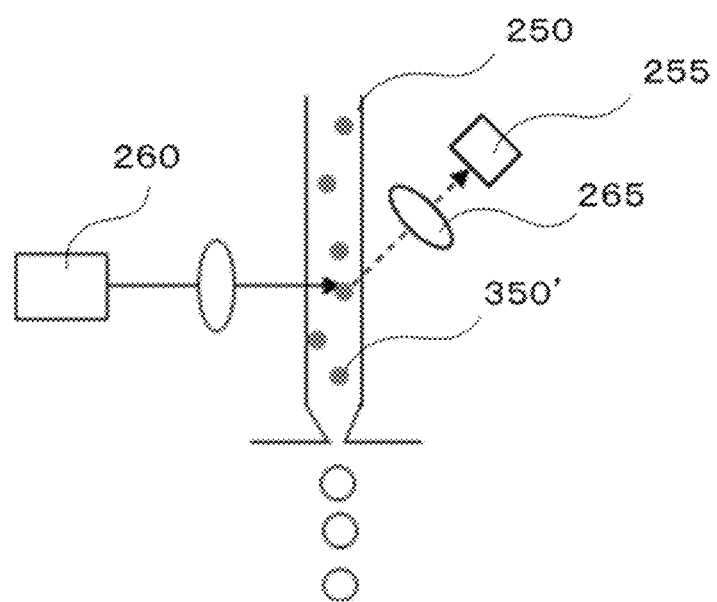
FIG. 20 is a schematic view illustrating one example of a method for counting cells that have passed through a microchannel.
Figure 21:
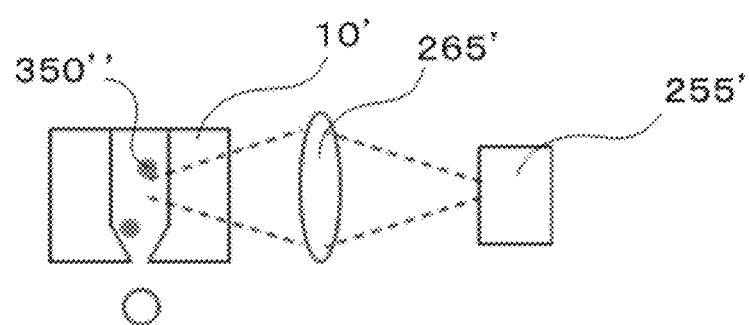
FIG. 21 is a schematic view illustrating one example of a method for acquiring an image of the vicinity of a nozzle part of a discharging head.

Examples of the treatment of observing the cells before the discharge include a method for counting cells 350' that have passed through microchannel 250 as illustrated in FIG. 20, and a method for acquiring an image of the vicinity of a nozzle part of a discharging head as illustrated in FIG. 21. The method of FIG. 20 is used in a cell sorter apparatus, and can employ, for example, cell sorter SH800 manufactured by Sony Corp. In FIG. 20, liquid droplets can be formed while the presence or absence of the cells or the type of the cells is identified by irradiating the inside of the microchannel 250 with laser light from light source 260, and detecting scattered light or fluorescence by detector 255 using condenser lens 265. By use of this method, the number of cells landed into a predetermined filled site (well) can be predicted from the number of cells that have passed through the microchannel 250.

A single-cell printer manufactured by Cytena GmbH may be used as discharging head 10' illustrated in FIG. 21. In FIG. 21, the number of cells landed into a predetermined filled site (well) can be predicted before the discharge by estimating that cells 350" in the vicinity of a nozzle part have been discharged, from results of acquiring an image in image acquisition part 255' via lens 265' in the vicinity of the nozzle part, or by estimating the number of cells that have probably been discharged, from the difference between images obtained before and after the discharge. Liquid droplets are continuously formed in the method for counting cells that have passed through a microchannel as illustrated in FIG. 20, whereas on-demand liquid droplet formation is possible in FIG. 21, which is more preferred.

[Treatment of Counting Cell After Landing]

The treatment of counting the cells after the landing includes a method of detecting fluorescently stained cells by observing filled sites (wells) in a plate under a fluorescence microscope. This method is described in, for example, Sangjun et al., PLoS One, Volume 6 (3), e17455.

The method for observing the cells before the discharge of the liquid droplets and after the landing thereof has problems mentioned below. Depending on the type of the plate to be produced, it is most preferred to observe the cells in the liquid droplets during discharge. In the method of observing the cells before the discharge, cells that seem to have been landed are counted based on cells that have passed through a channel or from image observation before the discharge (and after the discharge), and thus it is not confirmed whether the cells have actually been discharged and an unexpected error may arise. For example, the case occurs where a dirty nozzle part fails to correctly discharge liquid droplets, which are in turn attached to a nozzle plate; thus, the cells in the liquid droplets cannot be landed. In addition, the problem may arise that the cells remain in a narrow region in the nozzle part, or the cells move more than expected by discharge action and fall out of the range of observations.

The approach of detecting the cells on a plate after the landing may also have problems. First of all, a microscopically observable plate needs to be prepared. A plate having a transparent and flat bottom, particularly, a plate having a glass bottom, is generally used as the observable plate. Since such a plate is special, there is a problem that general filled sites (wells) are unusable. There is also a problem that cells with a cell number as large as dozens, etc. overlap with each other and therefore, cannot be precisely counted. Hence, it is preferred to perform the treatment of observing the cells before the discharge or the treatment of counting the cells after the landing, in addition to counting the cells contained in the liquid droplets using a sensor and a particle (cell) counting unit after the discharge of the liquid droplets and before the landing of the liquid droplets into filled sites (wells).

A light receiving element having one or a few light receiving parts, for example, a photodiode, an avalanche photodiode, or a photomultiplier tube, may be used as the light receiving element. In addition, a two-dimensional sensor, such as CCD (charge coupled device), CMOS (complementary metal oxide semiconductor), or gate CCD, which is provided with light receiving elements in the form of a two-dimensional array may be used.

Figure 22:
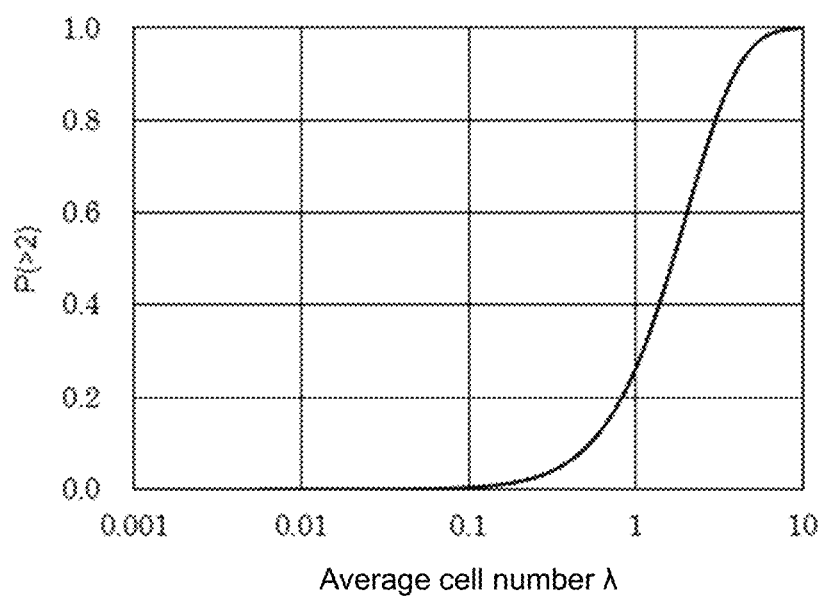
FIG. 22 is a graph illustrating the relationship between probability P (>2) and an average cell number.

In the case of using a light receiving element having one or a few light receiving parts, the number of cells incorporated in liquid droplets may be determined from fluorescence intensity using a calibration curve prepared in advance. Typically, the presence or absence of the cells in flying liquid droplets is binarily detected. When the cell suspension liquid has a sufficiently low cell concentration and is discharged substantially in a state where only one or zero cells are incorporated into a liquid droplet, the binary detection is capable of counting the cells with adequate accuracy. Assuming that the cells are randomly disposed in the cell suspension liquid, the number of cells in flying liquid droplets probably follows Poisson distribution. Thus, probability P (>2) that two or more cells are incorporated in a liquid droplet is represented by expression (1) given below. FIG. 22 is a graph illustrating the relationship between probability P (>2) and an average cell number. In this context, $\lambda$ represents an average cell number in liquid droplets and is obtained by multiplying the cell concentration of the cell suspension liquid by the volume of discharged liquid droplets.

$$P(>2)=1-(1+\lambda)\times e^{-\lambda} \quad \text{Expression (1)}$$

In the case of counting the cells by binary detection, a sufficiently small value of probability P (>2) is preferred for securing accuracy, and $\lambda<0.15$ is preferred at which probability P (>2) is 1% or less. The light source is not particularly limited and can be appropriately selected according to the purpose, as long as the fluorescence of the cells can be excited. For example, a general lamp, such as a mercury lamp or a halogen lamp, filtered so as to emit a specific wavelength, LED (light emitting diode), or laser may be used. However, particularly, for forming 1 nL or smaller tiny liquid droplets, it is preferred to use laser, since a narrow region needs to be irradiated with light having high intensity. Generally known various lasers such as solid-state laser, gas laser, and semiconductor laser may be used as a laser light source. The excitation light source may be a continuously irradiated region through which liquid droplets pass, or may emit pulsed light, at a timing delayed by a predetermined time with respect to liquid droplet discharge action, in synchronization with the discharge of liquid droplets.

<<Uncertainty Calculation Step>>

The uncertainty calculation step is the step of calculating uncertainty for each of the steps such as the cell suspension liquid production step, the liquid droplet landing step, and the cell counting step.

The uncertainty can be calculated in the same way as in the uncertainty in the cell suspension liquid production step.

As for the timing of calculation of the uncertainty, the uncertainty may be collectively calculated in a step next to the cell counting step. Alternatively, the uncertainty may be calculated at the final stage of each of the steps such as the cell suspension liquid production step, the liquid droplet landing step, and the cell counting step, and the calculated uncertainty components can be combined in a step next to the cell counting step to calculate combined uncertainty. In other words, the uncertainty for each of the steps described above can be appropriately calculated before calculation of combined uncertainty.

<<Output Step>>

The output step is the step of outputting the counted value of the cells contained in the cell suspension liquid landed in filled sites (wells) by the particle counting unit based on the detection results obtained by the measurement using the sensor.

The counted value means the number of cells contained in the filled sites (wells), counted by the particle counting unit from the detection results obtained by the measurement using the sensor.

The output means that the counted value is transmitted as electronic information by an apparatus such as a prime mover, communication equipment, or a calculator to a server as an external counting result storage unit in response to input, or the counted value is printed as printed matter.

The output step involves observing or predicting the cell number or nucleic acid number of each filled site (well) in the plate at the time of plate production, and outputting the observed value or the predicted value to an external storage part.

The output may be performed at the same time with the cell counting step, or may be performed after the cell counting step.

<<Recording Step>>

The recording step is the step of recording the observed value or the predicted value output in the output step.

The recording step can be suitably carried out in a recording part.

The recording may be performed at the same time with the output step, or may be performed after the output step.

The recording is meant to include not only imparting information to a recording medium, but storing information in the recording part.

<<Nucleic Acid Extraction Step>>

The nucleic acid extraction step is the step of extracting the nucleic acid from the cells in the filled sites (wells).

The extraction means that the nucleic acid is got out of the cells by disrupting their cell membranes or cell walls.

A heat treatment method at 90° C. to 100° C. is known as a method for extracting the nucleic acid from the cells. Heat treatment at lower than 90° C. might fail to extract DNA, whereas heat treatment at higher than 100° C. might degrade DNA. This heat treatment is preferably performed by the addition of a surfactant.

The surfactant is not particularly limited and can be appropriately selected according to the purpose. Examples thereof include ionic surfactants and nonionic surfactants. These surfactants may be used alone or may be used in combination of two or more thereof. Among them, a nonionic surfactant is preferred, since the nonionic surfactant neither denatures nor deactivates proteins although depending on the amount of the surfactant added.

Examples of the ionic surfactant include fatty acid sodium salt, fatty acid potassium salt, sodium alpha-sulfo fatty acid ester, sodium linear alkylbenzenesulfonate, sodium alkyl sulfuric acid ester, sodium alkyl ether sulfuric acid ester, and sodium alpha-olefinsulfonate. These ionic surfactants may be used alone or may be used in combination of two or more thereof. Among them, fatty acid sodium salt is preferred, and sodium dodecyl sulfate (SDS) is more preferred.

Examples of the nonionic surfactant include alkyl glycoside, alkyl polyoxyethylene ether (Brij series, etc.), octyl phenol ethoxylate (Triton X series, Igepal CA series, Nonidet P series, Nikkol OP series, etc.), polysorbates (Tween series such as Tween 20, etc.), sorbitan fatty acid ester, polyoxyethylene fatty acid ester, alkyl maltoside, sucrose fatty acid ester, glycoside fatty acid ester, glycerin fatty acid ester, propylene glycol fatty acid ester, and fatty acid monoglyceride. These nonionic surfactants may be used alone or may be used in combination of two or more thereof. Among them, polysorbates are preferred.

The content of the surfactant is preferably 0.01% by mass or more and 5.00% by mass or less with respect to the total amount of the cell suspension liquid in the filled site (well). The content of 0.01% by mass or more can exert effects on DNA extraction. The surfactant having a content of 5.00% by mass or less can prevent the inhibition of PCR amplification. Therefore, the content is preferably 0.01% by mass or more and 5.00% by mass or less, as described above, in terms of a numerical range that produces both the effects.

The method described above may not sufficiently extract DNA from cells having a cell wall. In this case, examples of the extraction method include modes such as an osmotic shock method, a freeze-thaw method, an enzymatic digestion method, use of kits for DNA extraction, an ultrasonication method, a French press method, and homogenizers. Among them, an enzymatic digestion method is preferred, since this method exhibits smaller loss capability of extracted DNA.

<<Other Step>>

Other step is not particularly limited and can be appropriately selected according to the purpose. Examples thereof include enzyme deactivation step.

—Enzyme Deactivation Step—

The enzyme deactivation step is the step of deactivating an enzyme.

Examples of the enzyme include DNase, RNase, and enzymes used for extracting the nucleic acid in the nucleic acid extraction step.

The method for deactivating the enzyme is not particularly limited and can be appropriately selected according to the purpose. A method known in the art can be suitably used.

The device for use in the nucleic acid analysis method of the present invention can be produced by the method as mentioned above.

<Calibration Curve Data Generation Step and Calibration Curve Data Generating Part>

The calibration curve data generation step is the step of generating calibration curve data on the at least on standard nucleic acid based on the copy number of the standard nucleic acid of specific copy number(s). The calibration curve data generation step is suitably carried out by a calibration curve data generating part and a calibration curve data generating unit.

The calibration curve data means data on the number(s) of the nucleotide sequence(s) (copy number(s)) of the at least one standard nucleic acid. The calibration curve data may be the generated data itself, and is also meant to include a calibration curve itself derived from the data.

The calibration curve means a relational expression between a parameter such as the amount or activity of a substance having a known amount or activity for use in analysis, and a parameter different from the parameter. The parameter is not particularly limited and can be appropriately selected according to the purpose. Examples thereof include the "copy number (copy)" of a specific nucleotide sequence, and the "read number" of a specific nucleotide sequence.

The calibration curve data can be generated from data on the copy number of the standard nucleic acid in the library acquired by a calibration curve data generating unit. The calibration curve data is not particularly limited and can be appropriately selected according to the purpose, as long as the data is related to the copy number of the standard nucleic acid in the library acquired using an analyzing instrument mentioned later. The method for generating the calibration curve data from the standard nucleic acid of a specific copy number is not particularly limited and can be appropriately selected according to the purpose. Examples thereof include a method of amplifying the standard nucleic acid of a specific copy number by a nucleic acid amplification method, and representing the relationship between the amplification results and the original specific copy number by a relational expression.

The nucleic acid analysis method of the present invention can highly accurately analyze (quantify) even a very small number of analyte nucleic acids by using the standard nucleic acid of a specific copy number in the calibration curve data generation step.

In the calibration curve data generation step, preferably, the at least one standard nucleic acid of specific copy number(s) is comprised at specific copy numbers different from each other in two or more different systems, and the calibration curve data thus obtained from the standard nucleic acid is normalized and combined to generate a calibration curve. The type of the standard nucleic acid used can be decreased by the embodiment in which the at least one standard nucleic acid of specific copy number(s) is comprised at specific copy numbers different from each other in two or more different systems, and the calibration curve data thus obtained from the standard nucleic acid is normalized and combined to generate a calibration curve.

<Analyte Nucleic Acid Analysis Step and Analyte Nucleic Acid Analyzing Part>

The analyte nucleic acid analysis step is the step of identifying a nucleotide sequence of the analyte nucleic acid while identifying the number of the nucleotide sequence of the analyte nucleic acid. The analyte nucleic acid analysis step is suitably carried out by an analyte nucleic acid analyzing part.

The identification of a nucleotide sequence of the analyte nucleic acid means that the nucleotide sequence of the analyte nucleic acid is read.

The identification of the number of the nucleotide sequence of the analyte nucleic acid means that the copy number of the nucleotide sequence comprised in the analyte nucleic acid is counted from the measurement value (read number, etc.) of the analyte nucleic acid using the calibration curve generated in the calibration curve data generation step. When the analyte nucleic acid comprises two or more nucleic acids (fragments) having different nucleotide sequences, the identification of a nucleotide sequence and the identification of the number of the nucleotide sequence are performed with respect to each of the nucleotide sequences comprised in the analyte nucleic acid. Data of the read analyte nucleic acid may be managed in a unit called "read number" with respect to each of the nucleotide sequences.

The number of the analyte nucleic acid is also referred to as a "copy number", the "number of molecules", etc.

The analyte nucleic acid analysis step may be performed (processed) in parallel with the aforementioned calibration curve data generation step.

For the analyte nucleic acid analysis step, see, for example, methods described in an analysis method for next-generation sequencers published by Illumina, (www.a-dres.ehime-u.ac.jp/news/NGS1.pdf), Non-Patent Document 1, an analysis method for sequencing using nanopore devices (Oxford Nanopore Technologies Ltd..), an analysis method for sequencing using PacBio RS II/Sequel system (Pacific Biosciences of California, Inc.), and an analysis method for Ion Torre semiconductor sequencing system series (Thermo Fisher Scientific Inc.). The analyte nucleic acid analysis step can be performed with an analyzing instrument for use in each of these analysis methods.

The analyzing instrument is not particularly limited and can be appropriately selected according to the purpose.

Examples thereof include sequencers manufactured by Illumina. Inc., nanopore devices, single-molecule sequencers manufactured by Pacific Biosciences of California, Inc., and Ion Torrent™ semiconductor sequencers manufactured by Thermo Fisher Scientific Inc. A commercially available product can be used as the analyzing instrument. Examples of the commercially available product include: Miseq (manufactured by Illumina, Inc.); MiION, GridION, and PromethION (manufactured by Oxford Nanopore Technologies Ltd.); PacBio RS H (manufactured by Pacific Biosciences of California, Inc.); and Ion Gene Studio S5 (Thermo Fisher Scientific Inc.).

The processing of the nucleic acid analysis program of the present invention can be executed using a computer having a controlling part constituting a nucleic acid analyzing apparatus.

Hereinafter, a hardware configuration and a functional configuration of the nucleic acid analyzing apparatus is described.

<Hardware Configuration of Nucleic Acid Analyzing Apparatus>

Figure 24:
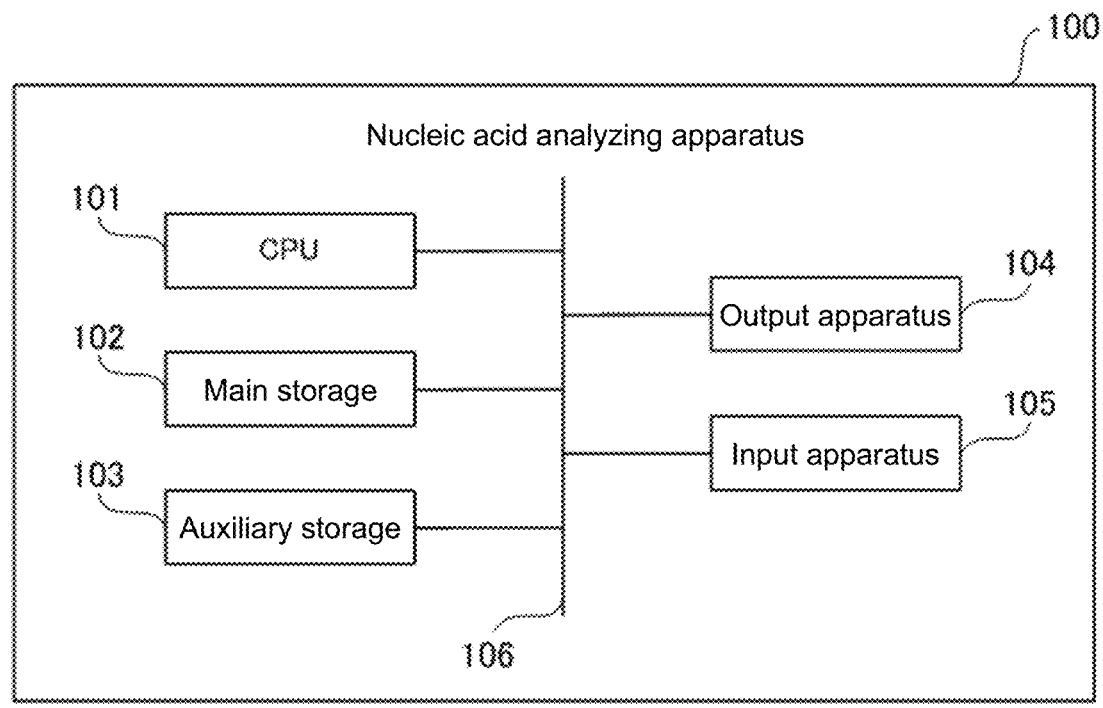
FIG. 24 is a block diagram illustrating one example of a hardware configuration of a nucleic acid analyzing apparatus.

FIG. 24 is a block diagram illustrating one example of a hardware configuration of nucleic acid analyzing apparatus 100.

As illustrated in FIG. 24, the nucleic acid analyzing apparatus 100 has CPU (central processing unit) 101, main storage 102, auxiliary storage 103, output apparatus 104, and input apparatus 105. These parts are connected to each other via bus 106.

The CPU 101 is a processing apparatus that variously performs control or operation. The CPU 101 achieves various functions by running OS (operating system) or a program stored in the main storage 102 or the like. Specifically, the CPU 101 in the present Examples functions as controlling part 130 of the nucleic acid analyzing apparatus 100 by running the nucleic acid analysis program.

The CPU 101 controls the action of the whole nucleic acid analyzing apparatus 100. In the present Examples, an apparatus that controls the action of the whole nucleic acid analyzing apparatus 100 is set to the CPU 101, though the apparatus is not limited thereto. Such an apparatus may be, for example, FPGA (field programmable gate array).

The nucleic acid analysis program or various databases are not necessarily required to be stored in the main storage 102, the auxiliary storage 103, or the like. The nucleic acid analysis program or various databases may be stored in an additional information processing apparatus, etc. connected to the nucleic acid analyzing apparatus 100 via the Internet, LAN (local area network), WAN (wide area network), or the like. The nucleic acid analyzing apparatus 100 may acquire and run the nucleic acid analysis program or various databases from such an additional information processing apparatus.

The main storage 102 stores various programs and stores data, etc. necessary for running these programs.

The main storage 102 has ROM (read only memory) and RAM (random access memory) (not illustrated).

The ROM stores various programs such as BIOS (basic input/output system).

The RAM functions as a scope of work that is developed when various programs stored in the ROM is run by the CPU 101. The RAM is not particularly limited and can be appropriately selected according to the purpose. Examples of the RAM include DRAM (dynamic random access memory) and SRAM (static random access memory).

The auxiliary storage 103 is not particularly limited and can be appropriately selected according to the purpose, as long as various pieces of information can be stored therein. Examples thereof include solid-state drives and hard disk drives. Alternatively, the auxiliary storage 103 may be, for example, a transportable storage such as a CD (compact disc) drive, a DVD (digital versatile disc) drive, or a BD (Blu-ray(R)disc) drive.

The output apparatus 104 can employ a display, a speaker, or the like. The display is not particularly limited, and a display known in the art can be appropriately used. Examples thereof include liquid-crystal displays and organic EL displays.

The input apparatus 105 is not particularly limited as long as the input apparatus can accept various requests for the nucleic acid analyzing apparatus 100. An input apparatus known in the art can be appropriately used. Examples thereof include keyboards, mice, and touch panels.

The hardware configuration as mentioned above can achieve the processing function of the nucleic acid analyzing apparatus 100.

<Functional Configuration of Nucleic Acid Analyzing Apparatus>

Figure 25:
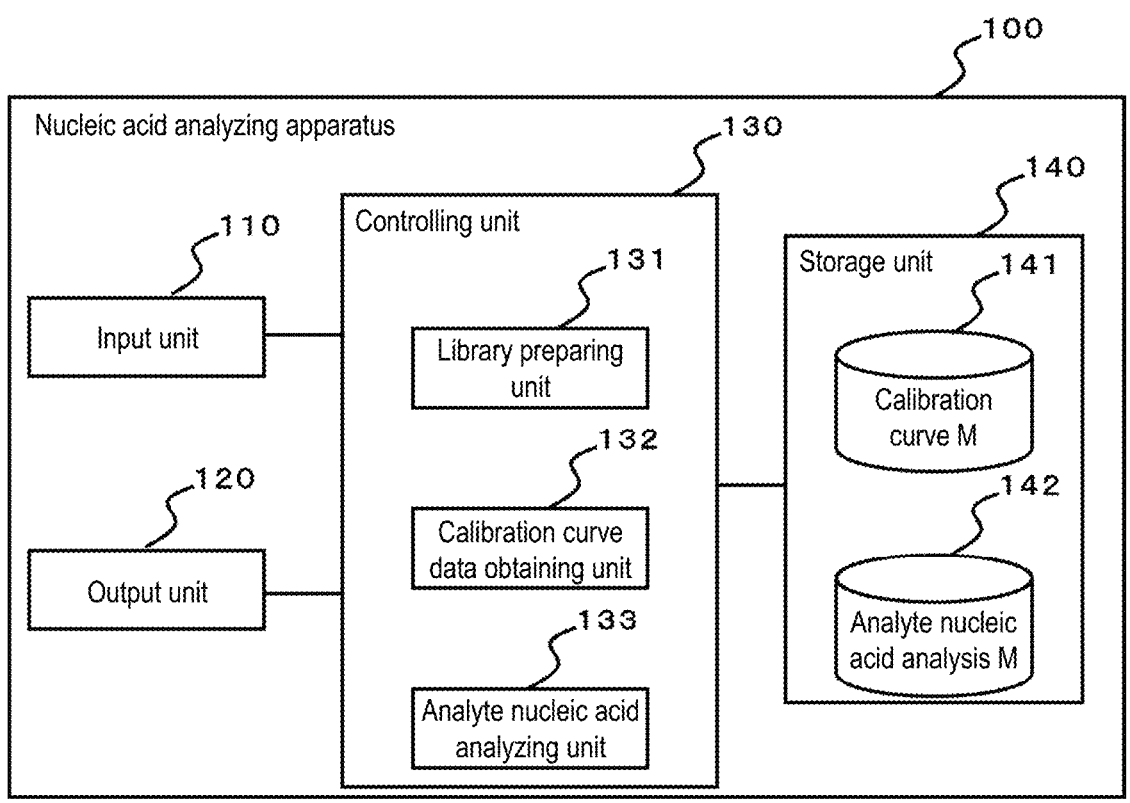
FIG. 25 is a diagram illustrating one example of a functional configuration of the nucleic acid analyzing apparatus.

FIG. 25 is a diagram illustrating one example of a functional configuration of nucleic acid analyzing apparatus 100.

As illustrated in this FIG. 25, the nucleic acid analyzing apparatus 100 has input part 110, output part 120, controlling part 130, and storage part 140.

The controlling part 130 has library preparing part 131, calibration curve data generating part 132, and analyte nucleic acid analyzing part 133. The controlling part 130 controls the whole nucleic acid analyzing apparatus 100.

The storage part 140 has calibration curve database 141 and analyte nucleic acid analysis database 142. Hereinafter, the "database" is also referred to as "DB". Data stored in the storage part may be stored in any of volatile and nonvolatile memories. The memory is also referred to as "M" and may be used in the same meaning as that of "DB".

The library preparing part 131 adjusts the reaction conditions of library preparation based on information on the analyte nucleic acid input from the input part 110.

The calibration curve data generating part 132 generates calibration curve data of the standard nucleic acid based on data of the copy number(s) of the at least one standard nucleic acid of specific copy number(s). The controlling part 130 allows the calibration curve M 141 to store the calibration curve data thus acquired.

The analyte nucleic acid analyzing part 133 uses analyte nucleic acid analysis data stored in the analyte nucleic acid analysis M 142 of the storage part 140 to identify a nucleotide sequence of the analyte nucleic acid while analyzing the number of the nucleotide sequence of the analyte nucleic acid by comparison with the data in the calibration curve M 141.

Figure 26:
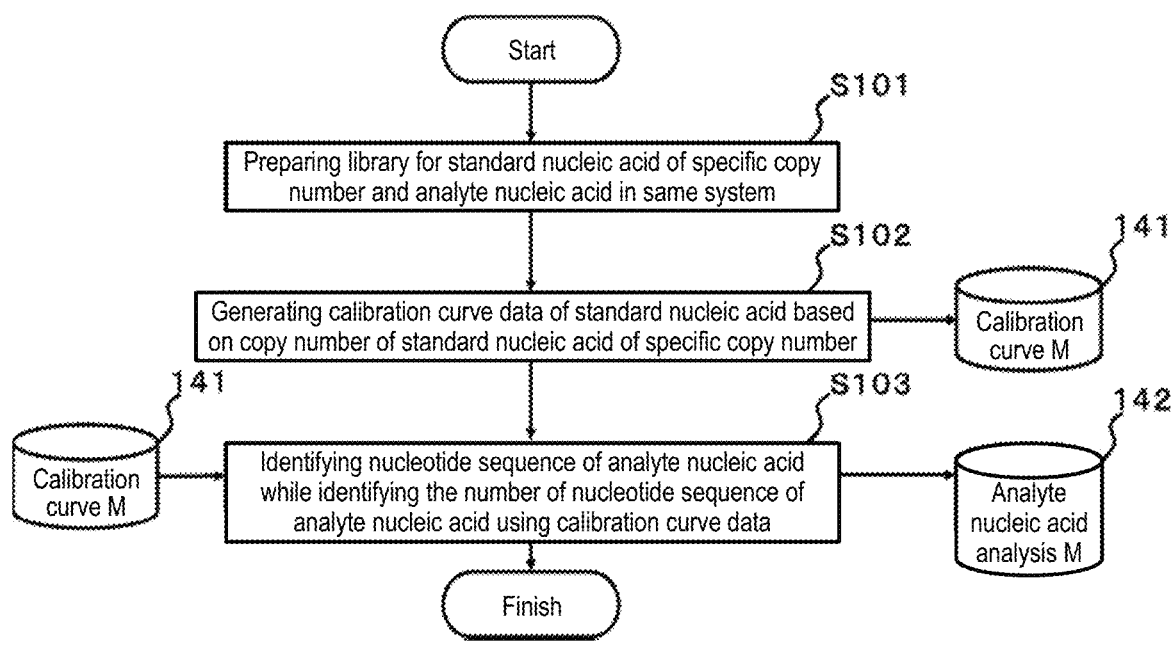
FIG. 26 is a flow chart illustrating one example of program processing of nucleic acid analysis.

Next, the procedure of processing the nucleic acid analysis program of the present invention is illustrated. FIG. 26 is a flow chart illustrating one example of the procedure of processing the nucleic acid analysis program in the controlling part 130 of the nucleic acid analyzing apparatus 100.

In step S101, the library preparing part 131 of the controlling part 130 in the nucleic acid analyzing apparatus 100 adjusts the reaction conditions of library preparation by outputting the reaction conditions to the output part 120, based on information on the standard nucleic acid and the analyte nucleic acid input from the input part 110. The process proceeds to step S102.

In step S102, the calibration curve data generating part 132 of the controlling part 130 in the nucleic acid analyzing apparatus 100 generates calibration curve data of the at least one standard nucleic acid based on the copy number(s) of the at least one standard nucleic acid of specific copy number(s), and allows the calibration curve M 141 to record the acquired results. The process proceeds to step S103. For example, the "read number" of the standard nucleic acid in the system may be used as the calibration curve data.

In step S103, the analyte nucleic acid analyzing part 133 of the controlling part 130 in the nucleic acid analyzing apparatus 100 identifies a nucleotide sequence of the analyte nucleic acid while identifying the number of the nucleotide sequence of the analyte nucleic acid using the generated calibration curve data acquired from the calibration curve M 141, and allows the analyte nucleic acid analysis M 142 to record the analysis data. This processing is terminated.

The processes of S102 and S103 may be performed in parallel.

The device related to the nucleic acid analysis method of the present invention is widely used in bio-related industry, life science industry, and medical industry, etc., and can be suitably used in, for example, apparatus calibration, calibration curve generation, accuracy management for testing apparatuses, accuracy evaluation for PCR apparatuses, and accuracy management for nucleotide sequence analyzing instruments.

The device can be applied to a method specified by an official method or a notified method, etc. when carried out for infectious diseases.

(Device for Library Preparation)

The device for library preparation of the present invention is particularly suitably used for the preparation of the library for use in the nucleic acid analysis method of the present invention, and has at least one standard nucleic acid of specific copy number(s).

The device for library preparation of the present invention is the same as or similar to the device for use in the nucleic acid analysis method of the present invention, so that the description about the device for library preparation is omitted.

The device for library preparation of the present invention can be suitably used in nucleic acid analysis involving a next-generation sequencer.

In the device for library preparation of the present invention, the at least one standard nucleic acid preferably satisfies the expression $CV < 1/\sqrt{x}$ which is represented by a coefficient of variation (CV value) obtained by dividing uncertainty of the specific copy number by a mean of specific copy numbers, and mean x of specific copy numbers of the standard nucleic acid.

<Summary of Data Analysis Method>

In one aspect, the present invention relates to a method for analyzing data of high-throughput sequencing reaction using at least one standard samples comprising a nucleic acid of a specific copy number.

In the present aspect, the "specific copy number" is meant to be a predetermined value as the copy number of the nucleic acid comprised in the standard sample. The specific copy number accepts the presence of uncertainty of the value to some extent (e.g., within ±30%, within ±20%, within ±15%, within ±10%, within ±5%, within ±3%, or within ±1%). The uncertainty can be determined by "determination" described herein.

In the present aspect, the "standard sample" is a sample comprising a nucleic acid of a specific copy number, and is a sample that serves as a reference for determining a threshold in order to analyze output data comprising read derived from at least one sequence sample in the step of splitting output data mentioned later.

The standard sample is not particularly limited and can be appropriately selected according to the purpose. The standard sample may be, for example, a sample comprising the nucleic acid molecule or the nucleic acid described above, for example, a cell. Every cell can be used as the cell, irrespective of whether to be a eukaryotic cell, a prokaryotic cell, a multicellular organism cell, or a unicellular organism cell. These cells may be used alone or may be used in combination of two or more thereof.

In the present aspect, the "sequence sample" means a sample comprising a nucleic acid to be analyzed by the method of the present invention. Examples of the sequence sample include, but are not particularly limited to, samples comprising the nucleic acid molecule or the nucleic acid described above, for example: cells; body fluids such as blood, plasma, serum, saliva, spinal fluid, and tissue exudate; living tissues (e.g., biopsy tissues and tissue preparations such as FFPE), urine, milk, and hair; environmental samples (sea, river, soil, atmosphere, etc.); foods (e.g., meat and fish meat), supplements, pharmaceuticals (e.g., biopharmaceuticals), and production apparatuses thereof; and medical apparatuses.

The "high-throughput sequencing" described herein means sequencing that produces a large number of data than that of so-called first-generation sequencing such as Sanger sequencing. In the high-throughput sequencing, for example, $10^2$ or more, $10^3$ or more, $10^4$ or more, or $10^5$ or more molecules are sequenced at the same time. The high-throughput sequencing described herein includes next-generation sequencing (NGS). The next-generation sequencing includes second-generation sequencing, third-generation sequencing, fourth-generation sequencing, and high-throughput sequencing that will be developed in the future. The next-generation sequencing can utilize various commercially available sequencers and can utilize a sequencer, for example, Miseq, Hiseq, or NexSeq (Illumina, Inc.) for second-generation sequencing, for example, PacBio RS II/Sequel (Pacific Biosciences of California, Inc.) for third-generation sequencing, or, for example, MinION (Oxford Nanopore Technologies Ltd.) for fourth-generation sequencing. The "second-generation sequencing" described herein includes, for example, sequencing in which an adaptor sequence mediates linking to a substrate and serves as a priming site for reaction (for the details, see, for example, Rick Kamps et al., Int. J. Mol. Sci., 2017, 18 (2), p. 308). The "third-generation sequencing" described herein includes, for example, sequencing which involves using single-stranded closed circular DNA called SMRTbell as a template, introducing this template into sequencing units called ZMW, performing nucleic acid replication reaction with polymerase using four fluorescently labeled nucleotides in each ZMW, and performing reaction based on the resulting fluorescence pulse (for the details, see, for example, Anthony Rhoads et al., Genomics Proteomics Bioinformatics, 13, 2015, pp. 278-289). The "fourth-generation sequencing" described herein includes sequencing which is performed via software or the like based on obtained data on change in current caused when a nucleic acid molecule passes through a nanopore or comes closer to a nanopore (for the details, see, for example, Hengyun Lu et al., Genomics Proteomics Bioinformatics, 14, 2016, pp. 265-279).

<Step Comprised in Data Analysis Method>

The method for analyzing data according to the present invention comprises the steps of: a) preparing a library; b) subjecting the library prepared in the step a) to sequencing reaction to obtain output data; and c) dividing the reads in the output data, based on a threshold determined with reference to read number derived from the at least one standard sample in the output data. The method of the present invention may arbitrarily comprise the step of x) filling a sample into a container before the step a). Each step that may be comprised in the method of the present invention is described below in detail.

x) Sample Filling Step

The step of filling a sample into a container (also referred to as the "sample filling step") comprises filling the standard sample(s) and/or the sequence sample(s) into a container. The sample filling method is not particularly limited. For example, each sample can be added in a defined amount either directly without dilution or as a plurality of solutions and/or dispersion liquids prepared by the serial dilution thereof, or can be added based on counting of a micro region and a carrier containing a known number of nucleic acid molecules. The sample filling method can be selected as the best method according to filling accuracy or a filling time required for each level. Determination may be performed after the sample filling. The determination described herein means the experimental decision of the value of uncertainty. In the case of performing determination, uncertainty determined to each filled site can be suitably calculated in the aforementioned filling method or serial dilution preparation method. The sample filling (and the subsequent determination, if involved) can be performed as described in Examples, for example.

Sample Filled Container

The form of the container for sample filling is not particularly limited and has at least one or more filled sites. The shape of the filled site can agree with the shape of a mold of a general thermal cycler in order to perform the subsequent sequencing step. Examples of the material of the filled container include polystyrene, polypropylene, polyethylene, fluororesin, acrylic resin, polycarbonate, polyurethane, polyvinyl chloride, and polyethylene terephthalate. The capacity of the filled site is not particularly limited. The filled site can have a capacity of 1 μL to 1000 μL in consideration of the amount of a sample used in a general nucleic acid detection. The color of the filled site may be any of transparency, semitransparency, coloring, and complete light shielding, etc. The filled container is desirably closed in order to prevent the mixing of foreign matter into or the leakage of fillings. The closing unit may be capable of closing at least one filled site and capable of isolating each filled site such that the filled site can be closed or opened individually, or each filled site may be isolated. The shape of the closing unit may be a cap shape appropriate for the inside wall diameter of the container, or an adhesive film shape that covers a filled site opening. The closing unit may have, for example, an adhesive film shape capable of closing all filled sites at once. The closing unit may differ in adhesion strength between a site that needs to be reopened and a site that does not need to be reopened, so that mistakes made by users can be reduced. The closing unit may have a cut-here line between these sites.

When the method of the present invention does not comprise the sample filling step, for example, a container already filled with a sample can be used in a library preparation step mentioned later to perform the library preparation step.

a) Library Preparation Step

The method of the present aspect comprises the step of preparing a library under a same conditions for the at least one standard sample and at least one sequence sample (also referred to as the "library preparation step"). The details of the library preparation step are as described herein.

The library preparation under the same conditions for the at least one standard sample and at least one sequence sample enables a threshold to be determined based on a read number(s) derived from at least one standard sample in sequencing reaction mentioned later. Based on this threshold, the reads in the output data can be divided into, for example, a sequence worth analyzing and a sequence that can be attributed to an error source, in a splitting step mentioned later.

The library preparation under the same conditions for the at least one standard sample and at least one sequence sample is meant to be library preparation in which the presence or absence and order of each step illustrated above, and conditions thereof (e.g., a reagent concentration and a reaction temperature) are completely or essentially the same. In this context, the phrase "essentially the same" is meant to accept nonessential difference (e.g., experimental errors and minor difference in reaction conditions), though library preparation conditions are uniform in light of the purpose of determining a threshold based on read number derived from the at least one standard sample.

In one embodiment, the library preparation is performed in a same reaction system. The same reaction system includes, for example, the same solution system for library preparation. For example, the library preparation for the at least one standard sample and the at least one sequence sample may be performed in the same well of the sample filled container described above.

b) Step of Obtaining Output Data

The method of the present aspect comprises, after the step a), the step of subjecting the library prepared in the step a) to a sequencing reaction to obtain output data comprising reads derived from the one or more standard samples and the at least one sequence sample.

The details of the sequencing reaction are known to those skilled in the art. The details of the sequencing reaction may differ depending on the type of next-generation sequencing. In second-generation sequencing, for example, an adaptor sequence mediates linking to a substrate and serves as a priming site for sequencing reaction (for the details, see, for example, Rick Kamps et al., supra). Third-generation sequencing involves, for example, using single-stranded closed circular DNA called SMRTbell as a template, introducing this template into sequencing units called ZMW, performing nucleic acid replication reaction with polymerase using four fluorescently labeled nucleotides in each ZMW, and performing sequencing based on the resulting fluorescence pulse (for the details, see, for example, Anthony Rhoads et al., supra). In fourth-generation sequencing, sequencing is performed via software or the like based on obtained data on change in current caused when a nucleic acid molecule passes through a nanopore or comes closer to a nanopore (for the details, see, for example, Hengyun Lu et al., supra).

Various sequencers have been provided in order to perform next-generation sequencing, and any of these sequencers may be used in the sequencing reaction of the present invention. Examples of the sequencers that can be used include, but are not limited to, Miseq, Hiseq, and NexSeq (Illumina, Inc.), PacBio RS II/Sequel (Pacific Biosciences of California, Inc.), and MinION (Oxford Nanopore Technologies Ltd.) described above as well as Ion Torrent PGM™ (Thermo Fisher Scientific Inc.), Genome Sequencer (GS) FLX System (F. Hoffmann-La Roche, Ltd), Support Oligonucleotide Ligation Detection (SOLiD) (Thermo Fisher Scientific Inc.), and HeliScope Gene Sequencing (Helicos BioSciences Corp.).

A collection of sequence information (reads) obtained through the sequencing reaction is obtained as output data. The data thus output can be further analyzed using software or the like, and converted to more significant results such as a read number.

c) Step of Splitting Output Data

The method of the present invention comprises, after the step b), the step of dividing the reads in the output data obtained in the step b), based on a threshold determined with reference to read number(s) derived from the at least one standard sample in the output data, into a read equal to or less than the threshold and a read equal to or more than the threshold (also referred to as the "step of splitting the output data").

The "dividing" or "splitting" described herein means that the reads in the output data are separated into a group of reads having a read number equal to or more than the threshold and a group of reads having a read number equal to or less than the threshold. When there exists a read having the same value as the threshold, this read may be classified into any of the group of reads equal to or more than the threshold and into the group of reads equal to or less than the threshold.

A single threshold may be used, or a plurality of thresholds may be set. The single threshold allows the output data to be split into two groups. When the plurality of thresholds are set, the output data can be splitted into three or more groups.

The threshold may be, for example, the read number(s) derived from the at least one standard sample itself, or may be obtained by multiplying this read number by a predetermined coefficient. By multiplying it by the predetermined coefficient, the threshold can be flexibly set based on the read number(s) derived from the at least one standard sample according to the analysis purpose. The predetermined coefficient may be determined before analysis, or may be determined with reference to analysis results. Those skilled in the art can appropriately set the predetermined coefficient according to the analysis purpose and/or the types of the at least one standard sample and the at least one sequence sample, etc. In the case of, for example, excluding a larger number of unnecessary sequences from the analyte, the predetermined coefficient can be set to be higher. In the case of reducing the risk of excluding necessary sequences, the predetermined coefficient can be set to be lower. The predetermined coefficient can be, but not limited to, for example, 0.01 or more, 0.05 or more, 0.1 or more, 0.2 or more, 0.3 or more, 0.4 or more, 0.5 or more, 0.75 or more, 0.8 or more, or 0.9 or more. Also, the predetermined coefficient can be 100 or less, 50 or less, 10 or less, 5 or less, 4 or less, 3 or less, 2 or less, 1.5 or less, 1.2 or less, or 1.1 or less. The predetermined coefficient may be, for example, 0.01 to 100, 0.1 to 10, 0.3 to 4, 0.5 to 2, 0.8 to 1.2 or 0.9 to 1.1.

In one embodiment, in the step a) of the method of the present invention, a plurality of standard samples comprising the nucleic acid of the same or different specific copy numbers are used. The method of the present embodiment may further comprise, after the step b) and before the step c), the step of selecting a standard sample for determining the threshold in the step c). The method of the present embodiment may have an effect that the standard sample for determining the threshold can be selected from a plurality of samples comprising the nucleic acid at different copy numbers according to the analysis purpose, and thus range of choices of the threshold is widened. Furthermore, use of the plurality of standard samples comprising the nucleic acid at different copy numbers can reduce the risk of producing too high a threshold or too low a threshold.

In one embodiment, in the step a) of the method of the present invention, the same sequence sample is analyzed using a plurality of wells, and a plurality of standard samples comprising the nucleic acid of the same or different specific copy numbers are used, and in the step c), the threshold is determined using data normalized between or among the plurality of wells. The normalization can be performed according to a usual method, and can be performed, for example, by multiplying the read number of the sequence sample in each well by a specific value (or dividing the read number by a specific value) such that the entire read numbers of the wells are the same or substantially the same. Alternatively, the normalization may be performed such that the read numbers derived from the at least one standard sample comprised of the same specific copy number in the wells are the same or substantially the same. Provided that the sequence sample is added in the same amount to the wells, the normalization may be performed such that the sums of read number(s) derived from sequence sample are the same or substantially the same. In the case of normalization based on the sequence sample, when there is one or more wells in which the library preparation for the at least one standard sample and the sequence sample is performed in the same well(s), other wells may comprise no standard sample. Normalization enables the read number to be compared between or among wells, and allows the threshold to be determined with reference to the read number(s) derived from the at least one standard sample from the different wells. In one embodiment, in the step c) of the method of the present invention, a relational expression of the specific copy number(s) and the output read number(s) is drawn based on the data normalized between or among the plurality of standard samples; copy number(s) is estimated from the output read number(s) using an inverse function thereof; and the threshold is determined with reference to the estimated copy number(s). The relational expression is not limited and can be represented by, for example, y=ax+b wherein y represents an output read number, x represents a copy number, a and b each represent a constant, and b may be 0. In the present embodiment, the copy number serving as the threshold is not limited and can be, for example, 200 copies or less, 150 copies or less, 100 copies or less, or 50 copies or less, and, for example, 20 copies or less, 10 copies or less, 5 copies or less, 4 copies or less, 3 copies or less, 2 copies or less, or 1 copy.

The range of the term "plurality" described herein is not limited and can be, for example, 2 or more, 3 or more, 4 or more, 5 or more, or 10 or more and 100 or less, 50 or less or 20 or less.

In one embodiment, in the step a) of the method of the present invention, a plurality of standard samples comprising the nucleic acid of the same specific copy number are used. In the step c) of the method of the present embodiment, the threshold may be determined based on a mean or a median of read numbers derived from the plurality of standard samples. The method of the present embodiment may have an effect that a more highly reliable threshold can be obtained by determining the threshold based on read numbers derived from the plurality of standard samples comprising the nucleic acids of the same specific copy numbers.

The range of the specific copy number of the nucleic acid comprised in the standard sample is not limited. Those skilled in the art can set this range according to the analysis purpose. In the case of, for example, excluding a larger number of unnecessary sequences from the analyte, the specific copy number can be set to be higher. In the case of reducing the risk of excluding necessary sequences, the specific copy number can be set to be lower. The specific copy number can be, but not limited to, for example, 200 copies or less, 150 copies or less, 100 copies or less, or 50 copies or less, and, for example, 20 copies or less, 10 copies or less, 5 copies or less, 4 copies or less, 3 copies or less, 2 copies or less, or 1 copy.

For example, a sequence with a small read number (as in a read having a read number equal to or less than that derived from a standard sample comprising 1 copy of a nucleic acid) may be attributed to various error sources, for example, a sequence derived from an error resulting from sequencing, a sample-derived sequence contaminated after PCR, and a sample-derived sequence of the previous run remaining in a flow cell (in the case of a high-throughput sequencer having reusable flow cells). These errors are mixed into a sample during or after PCR, and are hardly involved in amplification reaction. Hence, these errors are output as a small read number. Thus, for example, sequence(s) derived from such an error and other sequence(s) can be distincted by dividing the reads in the output data based on the threshold determined with reference to read number(s) derived from the at least one standard sample comprising nucleic acid(s) of specific copy number(s).

In one embodiment, in the step c) of the method of the present invention, the output data is analyzed with the read equal to or less than the threshold included therein, without excluding the read equal to or less than the threshold in the output data. In another embodiment, in the step c) of the method of the present invention, the read equal to or less than the threshold in the output data is excluded, and data analysis is conducted on the read equal to or more than the threshold. Whether to include or exclude the read equal to or less than the threshold can be freely determined according to the analysis purpose. In the case of excluding the read equal to or less than the threshold, for example, a sequence that may be derived from various error sources and is unnecessary for analysis can be excluded. For example, the read(s) derived from the at least one sequence sample cannot take a read number equal to or less than that derived from 1 copy of a nucleic acid molecule. Thus, when the at least one standard sample comprises 1 copy of a nucleic acid molecule, every sequence having a read number equal to or less than the read number(s) derived from the at least one standard sample or the threshold determined with reference thereto may be excluded as a sequence not worth analyzing. The sequence not worth analyzing, derived from various error sources as described above is also referred to as a "ghost read" herein. The exclusion of the "ghost read" from the analyte is also referred to as "removing ghost".

<Kit>

In one aspect, the present invention relates to a kit for performing the method described herein. The kit of the present invention may comprise at least one of: a plate comprising at least one standard sample comprising at least one nucleic acid of specific copy number(s) in at least one well; a reagent necessary for library preparation and/or sequencing reaction (e.g., a primer, a buffer, and an enzyme); and an instruction.

<Program>

In one aspect, the present invention relates to a program for allowing a computer to perform the method described herein, or software for performing the method described herein.

The computer for performing the method described herein may be constituted, in terms of a hardware configuration, by CPU which processes acquired output data, RAM which is a main memory, a nonvolatile memory for buffering the acquired output data, and an interface for information communication or powder demand between the computer and an external apparatus. The computer may have a display that presents the output data, if necessary.

An exemplary method for allowing the computer to perform the method described herein is as follows: first, the CPU calls up the program of the present invention to the RAM from the nonvolatile memory. The program of the present invention is a program of splitting the output data, based on a threshold determined with reference to read number(s) derived from the at least one standard sample, into a read equal to or less than the threshold and a read equal to or more than the threshold, and optionally excluding the read equal to or less than the threshold in the output data. This program is input in advance in the nonvolatile memory. Next, the CPU acquires the output data from, for example, an interface such as a sequencer, and the output data is stored in the RAM, addressed, and then buffered to the nonvolatile memory. Subsequently, the CPU sequentially runs the program developed in the RAM, and thereby performs the processing, accumulation, and output of the stored output data. In this way, the program or the software of the present embodiment can be achieved.

EXAMPLES

Hereinafter, the present invention is described with reference to Examples. However, the present invention is not limited by these Examples at all.

Example 1

<Preparation of Device for Library Preparation>

A device for library preparation was prepared as described below.
—Preparation of Standard Nucleic Acid—
—Design of Artificial Nucleotide Sequence—

A plasmid was created to comprise dense nucleic acid sample DNA600-G (manufactured by National Institute of Advanced Industrial Science and Technology (AIST), NMIJ CRM 6205-a; see SEQ ID NO: 6) as an artificial nucleotide sequence, and selective marker URA3 disposed in tandem therewith.

Furthermore, a plasmid was prepared to comprise nucleic acids synthesized so as to have nucleotide sequences complementary to primers MiFish-U (see Non-Patent Document 1; manufacturer name: FASMAC Corp.; see SEQ ID NOs: 7 and 8) at both ends of a 130-bp nucleotide sequence having a GC content ratio of 50%, not forming a higher-order structure at 60° C., and not having a repeat sequence (see SEQ ID NOs: 1 to 5). Since the artificial nucleotide sequences have nucleotide sequences complementary to the primers MiFish-U at both ends, the standard nucleic acids and an analyte nucleic acid can be analyzed using primers having the same nucleotide sequences when fish 12S rRNA contained in the analyte nucleic acid is analyzed.

—Genetically Engineered Yeast—

Budding yeast YIL015W BY4741 (manufactured by ATCC, ATCC4001408) was used in the preparation of recombinants as carrier cells for 1 copy of a specific nucleic acid sequence. One copy of the specific artificial nucleic acid sequence was introduced to yeast genomic DNA by the homologous recombination between the prepared plasmids mentioned above, and the BAR1 region of the carrier cells to prepare a genetically engineered yeast. DNA600-G has uncertainty information on a nucleic acid concentration as product information of DNA600-G.

The production and analysis of the plasmids used were requested to an outsourcing synthesis company (FASMAC Corp.). Briefly, the artificially synthesized nucleic acid having the desired sequence was introduced to E. coli, followed by culture, extraction, and purification according to routine methods to produce the plasmids. The full-length sequences of the produced plasmids were determined using a sequencer to confirm that only 1 copy of the target nucleotide sequence was inserted in 1 plasmid molecule (data not shown).

From genome analysis using a sequencer, a homologously recombinable site in the yeast genomic DNA was confirmed to be only 1 copy (data not shown). PCR was performed on the insertion site of the plasmid sequence inwardly, and the amplification product was read using a sequencer to confirm that only 1 copy of the plasmid sequence was inserted in the insertion site (data not shown).

—Culture and Cell Cycle Control—

To an Erlenmeyer flask containing a 90 mL aliquot of the genetically engineered yeast cultured in 50 g/L of YPD medium (manufactured by Takara Bio Inc., CLN-630409), 900 µL of α1-Mating Factor acetate salt (manufactured by Sigma-Aldrich Co., LLC, T6901-5MG; hereinafter, referred to as "α factor") adjusted to 500 µg/mL using Dulbecco's phosphate buffered saline (manufactured by Thermo Fisher Scientific Inc., 14190-144; hereinafter, referred to as "DPBS") was added.

Subsequently, the flask was incubated at a shaking rate of 250 rpm at a temperature of 28° C. for 2 hours using Bioshaker (manufactured by TAITEC Corp., BR-23FH) so that the yeast was synchronized to the G0/G1 phase to obtain a yeast suspension liquid.

—Fixation—

Forty-five mL of the yeast suspension liquid already confirmed to be synchronized was transferred to a centrifugal tube (manufactured by AS ONE Corp., VIO-50R), which was then centrifuged at a rotational speed of 3000 rpm for 5 minutes using a centrifuge (manufactured by Hitachi, Ltd., F16RN). The supernatant was removed to obtain yeast pellets.

To the obtained yeast pellets, 4 mL of formalin (manufactured by Wako Pure Chemical Industries, Ltd., 062-01661) was added, and the mixture was left standing for 5 minutes and then centrifuged. The supernatant was removed, and the residue was suspended by the addition of 10 mL of ethanol to obtain a fixed yeast suspension liquid.

—Nuclear Staining—

A 200 µL aliquot of the fixed yeast suspension liquid was washed once with DPBS and then resuspended in 480 µL of DPBS.

Next, 20 µL of 20 mg/mL RNase A (manufactured by Nippon Gene Co., Ltd., 318-06391) was added to the suspension, followed by incubation at 37° C. for 2 hours using Bioshaker.

Next, 25 µL of 20 mg/mL proteinase K (manufactured by Takara Bio Inc., TKR-9034) was added to the mixture, followed by incubation at 50° C. for 2 hours using Petite Cool (manufactured by WakenBtech Co., Ltd., Petite Pool MiniT-C).

Finally, 6 µL of 5 mM SYTOX Green Nucleic Acid Stain (manufactured by Thermo Fisher Scientific Inc., 57020) was added to the mixture, and the nuclei were stained for 30 minutes in the shade.

—Dispersion—

The yeast suspension liquid thus stained was dispersed at an output of 30% for 10 seconds using an ultrasonic homogenizer (manufactured by Yamato Scientific Co., Ltd., LUH150) to obtain a yeast suspension liquid.

—Dispensing and Cell Counting—

As described below, the yeast fungus in liquid droplets was counted and discharged at 1 cell per well to prepare a plate having a known cell number. Specifically, the liquid droplet forming apparatus illustrated in FIG. 15 was used. The yeast suspension liquid was sequentially discharged at 10 Hz to the wells of a 96-well plate (trade name: MicroAmp 96-well Reaction plate, manufactured by Thermo Fisher Scientific Inc.) by a discharging head (manufactured by Richo Co., Ltd.) in a piezoelectric application mode as a liquid droplet discharging unit.

The yeast in the discharged liquid droplets was photographed using a highly sensitive camera (manufactured by Tokyo Instruments, Inc., sCMOS pco.edge) as a light receiving unit. The light source used was YAG laser (manufactured by Spectra-Physics, Inc., Explorer ONE-532-200-KE). The taken image was processed using image processing software Image J as a particle counting unit, and the cells were counted to prepare a plate containing one cell in each well (hereinafter, also referred to as a "plate having known cell number(s)").

—Nucleic Acid Extraction—

ColE1/TE having 5 ng/µL ColE1 DNA (manufactured by Wako Pure Chemical Industries, Ltd., 312-00434) was prepared using a Tris-EDTA (TE) buffer. A Zymolyase solution having 1 mg/mL Zymolyase® 100T (manufactured by Nacalai Tesque, Inc., 07665-55) was prepared using ColE1/TE.

The Zymolyase solution was added at 4 µL per well to the prepared plate having known cell number(s), which was then incubated at 37.2° C. for 30 minutes to lyse cell walls (nucleic acid extraction). Then, the lysate was heat-treated at 95° C. for 2 minutes to prepare a reference device (device for library preparation).

Next, in order to consider the reliability of results obtained from the plate having known cell number(s), a plate having a known cell number of 1 is produced to calculate the uncertainty of the cell number of 1. The uncertainty of various copy numbers can be calculated by use of a method given below with respect to each of the specific copy numbers.

—Calculation of Uncertainty—

In the present Example, the uncertainty components used were the number of cells in the liquid droplets, the copy number of the nucleic acid in the cells, the number of cells in the wells, and contamination.

The number of cells in the liquid droplets used was the number of cells in the liquid droplets counted by the image analysis of the liquid droplets discharged by the discharging unit, and the number of cells obtained by microscopic observation with respect to each of the liquid droplets discharged by the discharging unit and landed onto a glass slide.

The copy number of the nucleic acid in the cells (cell cycle) was calculated using the percentage (99.5%) of cells corresponding to the G1 phase of the cell cycle, and the percentage (0.5%) of cells corresponding to the G2 phase. Specifically, the cultured yeast was stained with a nuclear staining agent (SYTOX™ Green Dead Cell Stain, Invitrogen™), and the fluorescence luminance thereof was measured. One copy of DNA is incorporated in the cells at the G1 phase, and 2 copies of DNA are incorporated in the cells at the G2 phase. The luminance is higher at the G2 phase. Therefore, the copy number of the nucleic acid in the cells was calculated based on the luminance.

The number of cells in the wells was counted as the number of discharged liquid droplets landed into the wells. However, in the counting for 96 samples, all the liquid droplets were landed into the wells. Therefore, the number of cells in the wells was excluded as a component from the calculation of the uncertainty.

The contamination was confirmed by 3 trials each involving using 4 µL of a filtrate of the cell suspension liquid in real-time PCR, and examining whether the filtrate is contaminated with a nucleic acid other than the nucleic acid in the cells is contaminated. As a result, all the 3 trials resulted in the lower limit value of detection. Therefore, the contamination was also excluded as a component from the calculation of the uncertainty.

The uncertainty is determined as by determining standard deviation from the measurement value of each component, multiplying the standard deviation by a sensitivity coefficient to unify into the unit of the measurand, and determining combined standard uncertainty based on the unit by the sums-of-squares method from standard uncertainty. The combined standard uncertainty merely includes values in the range of approximately 68% of normal distribution. Therefore, the combined standard uncertainty is doubled so that expanded measurement uncertainty can be obtained as the uncertainty in consideration of the range of approximately 95% of normal distribution. The results are illustrated in the budget sheet of Table 2 below.

uncertainty evaluation. In the present Example, only type A uncertainty evaluation was conducted, so that the probability distribution column was blank.

In Table 2, "Divisor" denotes a number for normalizing the uncertainty obtained from each component.

In Table 2, "Standard uncertainty" denotes a value obtained by dividing "Value (±)" by "Divisor".

In Table 2, "Sensitivity coefficient" denotes a value for use in unification into the unit of the measurand.

Next, a mean of specific copy numbers of the standard nucleic acids (nucleotide sequences) filled into the wells, and the uncertainty thereof were calculated. The results are illustrated in Table 3. The coefficient of variation (CV value) was calculated by dividing the value of the uncertainty by the mean of specific copy numbers.

TABLE 3

| Specific copy number | | Coefficient of variation |
|---|---|---|
| Mean copy | Uncertainty copy | (CV value) % |
| 1.02E+00 | 1.28E-01 | 12.60 |
| 2.03E+00 | 1.81E-01 | 8.91 |
| 4.07E+00 | 2.56E-01 | 6.30 |
| 8.13E+00 | 3.62E-01 | 4.46 |
| 1.63E+01 | 5.12E-01 | 3.15 |
| 2.13E+01 | 5.87E-01 | 2.75 |
| 6.50E+01 | 1.02E+00 | 1.58 |
| 1.30E+02 | 1.45E+00 | 1.11 |

In the method described above, the obtained accuracy of dispensing of the standard nucleic acid of a specific copy number of 1, i.e., 1 copy of the standard nucleic acid (nucleotide sequence) (one yeast), into each well was

TABLE 2

| Symbol | Uncertainty component | Value (±) | Probability distribution | Divisor | Standard uncertainty | Sensitivity coefficient | Standard uncertainty (unit of measurand) |
|---|---|---|---|---|---|---|---|
| u1 | The number of cell in liquid droplet | 0.1037 cells | — | 1 | 0.1037 cells | 1.0290 copies/cell | 0.1067 copies |
| u2 | Copy number of nucleic acid in cell (cell cycle) | 0.0709 copies | — | 1 | 0.0709 copies | — | 0.0709 copies |
| u3 | The number of cell in well | — | — | — | — | — | — |
| u4 | Contamination | — | — | — | — | — | — |
| uc | Combined standard uncertainty | | Normal distribution | | | | 0.1281 copies |
| U | Expanded measurement uncertainty | | Normal distribution (k = 2) | | | | 0.2562 copies |

In Table 2, "Symbol" denotes an arbitrary symbol associated with the uncertainty component.

In Table 2, "Value (±)" denotes the experimental standard deviation of a mean, and is obtained by dividing the calculated experimental standard deviation by the square root of the number of data.

In Table 2, "Probability distribution" denotes the probability distribution of the uncertainty component, and is given a blank for type A uncertainty evaluation and either normal distribution or rectangular distribution for type B ±0.1281 copies. In the case of filing 1 or more copies into each well, the accuracy of filling of the standard nucleic acid (nucleotide sequence) of a specific copy number is determined by stacking this accuracy.

As seen from the results described above, the obtained expanded measurement uncertainty serving as an index for the dispersion of measurement is stored as data on the device. Thus, users in experiments can use the index for uncertainty as a criterion for judging the reliability of the result of measurement with respect to each well. Use of the criterion for judging the reliability described above allows performance of analytical tests to be evaluated with high accuracy.

—Determination of Uncertainty to Each Filled Site—

The aforementioned calculated uncertainty (or coefficient of variation) was determined to each well.

Thus, the mean of specific copy numbers of low-concentration nucleic acid sample series and the uncertainty and the coefficient of variation thereof were able to be calculated and determined to each well.

Example 2

<Practice of Nucleic Acid Analysis Method—1: Calculation of Copy Number of Fish Muscle Tissue 12S rRNA>

In Example 2, NGS analysis was conducted using DNA samples extracted from fish muscle tissues.

First, muscle tissues of 3 species, *Pagrus major*, *Oncorhynchus mykiss*, and *Sardinops melanostictus*, were prepared as the fish muscle tissues, and DNA was extracted therefrom using DNeasy Blood & Tissue Kit (Qiagen N.V.). Each extracted DNA was used as an analyte nucleic acid.

1st PCR Reaction—

A well with a nucleic acid copy number of 1 copy (containing 1 yeast cell), a well with a nucleic acid copy number of 5 copies (containing 5 yeast cells), a well with a nucleic acid copy number of 10 copies (containing 10 yeast cells), and a well with a nucleic acid copy number of 50 copies (containing 50 yeast cells) were each prepared using 3 types of fish 12S rRNA sequences (see SEQ ID NOs: 1 to 3) of artificial nucleotide sequences (standard nucleic acids) 1 to 3 designed in Example 1. Each well was filled with these 3 types of artificial nucleotide sequences (hereinafter, also referred to as artificial 12S sequences). Specifically, the well with a nucleic acid copy number of 1 copy contained 1 yeast cell comprising the artificial nucleotide sequence of SEQ ID NO: 1, 1 yeast cell comprising the artificial nucleotide sequence of SEQ ID NO: 2, and 1 yeast cell comprising the artificial nucleotide sequence of SEQ ID NO: 3. The same holds true for the other wells. Then, 5.0 μL of the analyte nucleic acid was filled into each well for sample filling described above. Then, the fish 12S rRNA sequences of the analyte nucleic acid and the artificial nucleotide sequences were subjected to an amplification reaction by PCR in the same well. The composition of the reaction solution was as follows.

[Composition of Reaction Solution]

| | |
|---|---|
| Distilled water | 1.6 μL |
| KAPA HiFi HotStart ReadyMix (2x) | 12.0 μL |
| Primer F for 1st PCR (10 μM) | 0.7 μL |
| Primer R for 1st PCR (10 μM) | 0.7 μL |
| Fish muscle tissue-derived extracted DNA (sample) | 5.0 μL |
| Yeast DNA (containing artificial nucleotide sequences 1 to 3 and 0.4 U Zymolyase) | 4.0 μL |
| Total | 24.0 μL |

The primers for 1st PCR were MiFish-U (see Non-Patent Document 1) having an added sequence for an annealing reaction of primers for 2nd PCR.

The nucleic acid amplification was performed by PCR using T100™ Thermal Cycler (Bio-Rad Laboratories, Inc.). First, incubation was performed at 95° C. for 3 minutes. Then, 35 temperature cycles each involving 3 steps of 98° C. for 20 seconds, 65° C. for 15 seconds, and 72° C. for 15 seconds were performed. Finally, incubation was performed at 72° C. for 5 minutes, followed by cooling to 4° C. to terminate the reaction.

—2nd PCR Reaction: Binding of Adaptor Sequence—

PCR reaction was performed in order to add a tag for distinction among the samples for sequencing, and an adaptor sequence for application to a sequencing reaction to both ends of the obtained 1st PCR amplification product, to obtain a 2nd PCR reaction product. The composition of the reaction solution was as follows.

[Composition of Reaction Solution]

| | |
|---|---|
| Distilled water | 6.0 μL |
| KAPA HiFi HotStart ReadyMix (2x) | 12.0 μL |
| Primer F for 2nd PCR (10 M) | 1.0 μL |
| Primer R for 2nd PCR (10 μM) | 1.0 μL |
| 1st PCR product | 2.0 μL |
| Total | 20.0 μL |

The nucleic acid amplification was performed by PCR using T100™ Thermal Cycler (Bio-Rad Laboratories, Inc.). First, incubation was performed at 95° C. for 3 minutes. Then, 12 temperature cycles each involving 2 steps of 98° C. for 20 seconds and 72° C. for 15 seconds were performed. Finally, incubation was performed at 72° C. for 5 minutes, followed by cooling to 4° C. to terminate the reaction.

Purification of PCR Product by Agarose Gel Electrophoresis

Electrophoresis was performed at 100 V for 20 minutes using a 2% agarose gel. A band observed at 330 to 400 bp was excised, and the PCR product was purified using FastGene Gel/PCR Extraction Kit (manufactured by Nippon Genetics Co., Ltd.).

—Concentration Measurement of Nucleic Acid Sample—

The 2nd PCR product was quantified using Bioanalyzer 2100 (manufactured by Agilent Technologies, Inc.). The kit used was Agilent DNA7500 kit. Based on the quantification results, the 2nd PCR product was diluted into 10 ng/μL with TE. The diluted 2nd PCR products obtained from four wells were mixed into the same reaction solution.

—Sequencing Reaction Using Next-Generation Sequencer (NGS)—

The obtained 2nd PCR product was analyzed using a next-generation sequencer (apparatus name: Miseq, manufactured by Illumina, Inc.). The data obtained from the next-generation sequencer was analyzed by sequence processing to obtain information on nucleotide sequences and read numbers. The obtained data is illustrated in Table 4. The numerical values in the table denote read numbers.

TABLE 4

| | | 1 (copy/well) | 5 (copy/well) | 10 (copy/well) | 50 (copy/well) |
|---|---|---|---|---|---|
| Sample | Artificial nucleotide sequence 1 (SEQ ID NO: 1) | 18 | 131 | 98 | 624 |
| | Artificial nucleotide sequence 2 (SEQ ID NO: 2) | 69 | 61 | 61 | 636 |

TABLE 4-continued

|  | 1 (copy/well) | 5 (copy/well) | 10 (copy/well) | 50 (copy/well) |
|---|---|---|---|---|
| Artificial nucleotide sequence 3 (SEQ ID NO: 3) | 10 | 72 | 50 | 768 |
| *Pagrus major* | 27431 | 26441 | 26526 | 26309 |
| *Oncorhynchus mykiss* | 15525 | 15111 | 15547 | 14748 |
| *Sardinops melanostictus* | 2006 | 1349 | 1583 | 1390 |
| Others | 5 | 4 | 2 | 8 |

—Normalization of Read—

Data normalized with the sum of reads other than the reads of the artificial 12S sequence as 100,000 reads is illustrated in Table 5. The numerical values in the table denote read numbers.

TABLE 5

|  |  | 1 (copy/well) | 5 (copy/well) | 10 (copy/well) | 50 (copy/well) |
|---|---|---|---|---|---|
| Sample | Artificial nucleotide sequence 1 (SEQ ID NO: 1) | 40 | 305.3 | 224.5 | 1469.8 |
|  | Artificial nucleotide sequence 2 (SEQ ID NO: 2) | 153.4 | 142.2 | 139.7 | 1498.1 |
|  | Artificial nucleotide sequence 3 (SEQ ID NO: 3) | 22.2 | 167.8 | 114.5 | 1809 |
|  | *Pagrus major* | 61002.5 | 61626.9 | 60758.6 | 61969.1 |
|  | *Oncorhynchus mykiss* | 34525.3 | 35219.7 | 35610.9 | 34738 |
|  | *Sardinops melanostictus* | 4461 | 3144.2 | 3625.9 | 3274.1 |
|  | Others | 11.1 | 9.3 | 4.6 | 18.8 |

Based on the read numbers of the artificial 12S sequences 1, 2, and 3 in Table 5, a relational expression between a copy number (x) and an output read number (y) was drawn to obtain the expression y=31.343x (coefficient of determination, $R^2$=0.9612). The copy number of each fish species was estimated according to this expression to obtain Table 6. The numerical values in the table denote copy numbers.

TABLE 6

|  |  | 1 (copy/well) | 5 (copy/well) | 10 (copy/well) | 50 (copy/well) |
|---|---|---|---|---|---|
| Sample | *Pagrus major* | 1946.3 | 1966.2 | 1938.5 | 1977.1 |
|  | *Oncorhynchus mykiss* | 1101.5 | 1123.7 | 1136.2 | 1108.3 |
|  | *Sardinops melanostictus* | 142.3 | 100.3 | 115.7 | 104.5 |
|  | Others | 0.4 | 0.3 | 0.1 | 0.6 |

Example 3

<Practice of Nucleic Acid Analysis Method—2: Measurement of Fish Fauna Using Environmental DNA>

In Example 3, fish fauna was measured using environmental DNA in the Sagami River.

First, water was sampled from the Sagami River and filtered through a filter. DNA was extracted using a DNA extraction kit (trade name: DNeasy Blood & Tissue kit, manufactured by Qiagen N.V.) from the filter used in the filtration. The nucleic acid concentration of the extracted DNA sample (analyte nucleic acid) was quantified using Qubit 3 fluorometer (Invitrogen™)

—1st PCR Reaction—

Using 5 types of fish 12S rRNA sequences (see SEQ ID NOs: 1 to 5) of the artificial nucleotide sequences (standard nucleic acids) 1 to 5 designed in Example 1, wells were filled with 1 yeast cell (copy number=1) comprising the fish 12S rRNA sequence (see SEQ ID NO: 1) of artificial nucleotide sequence 1, 10 yeast cells (copy number=10) comprising the fish 12S rRNA sequence (see SEQ ID NO: 2) of artificial nucleotide sequence 2, 50 yeast cells (copy number=50) comprising the fish 12S rRNA sequence (see SEQ ID NO: 3) of artificial nucleotide sequence 3, 100 yeast cells (copy number=100) comprising the fish 12S rRNA sequence (see SEQ ID NO: 4) of artificial nucleotide sequence 4, or 500 yeast cells (copy number=500) comprising the fish 12S rRNA sequence (see SEQ ID NO: 5) of artificial nucleotide sequence 5, in the same way as in Example 1. The extracted DNA sample collected from the water sample from the Sagami River was filled at 2.0 µL (0.25 ng/µL) to each of the wells to prepare a device in which 5 levels of the standard nucleic acids were disposed. Then, the extracted DNA sample and the artificial nucleotide sequences 1 to 5 in the wells were subjected to an amplification reaction by PCR in the same well. The composition of the reaction solution was as follows.

[Composition of Reaction Solution]

| Distilled water | 1.6 µL |
|---|---|
| KAPA HiFi HotStart ReadyMix (2x) | 12.0 µL |
| Primer F for 1st PCR (10 µM) | 0.7 µL |
| Primer R for 1st PCR (10 µM) | 0.7 µL |
| Sagami River-derived environmental DNA extract (sample) | 5.0 µL |
| Yeast DNA (containing artificial nucleotide sequences 1 to 5 and 0.4 U Zymolyase) | 4.0 µL |
| Total | 24.0 µL |

The primers for 1st PCR were MiFish-U (see Non-Patent Document 1) having an added sequence for an annealing reaction of primers for 2nd PCR.

The standard nucleic acid (artificial nucleotide sequences 1 to 5) amplification was performed by PCR using Thermal Cycler (apparatus name: T100™, manufactured by Bio-Rad Laboratories, Inc.). First, incubation was performed at 95° C. for 3 minutes. Then, 35 temperature cycles each involving 3 steps of 98° C. for 20 seconds, 65° C. for 15 seconds, and 72° C. for 15 seconds were performed. Finally, incubation was performed at 72° C. for 5 minutes, followed by cooling to 4° C. to terminate the reaction.

—Purification of PCR Product Using Beads—

The PCR product was purified using AMPure XP reagent (Beckman Coulter, Inc.). First, the AMPure XP reagent was left standing at room temperature for 30 minutes or longer before use. The AMPure XP reagent was mixed by inversion for 1 minute or longer. Then, 20 µL of the AMPure XP reagent was added to each well that underwent the PCR reaction. The PCR reaction solution and the AMPure XP reagent were thoroughly mixed by pipetting 10 repetitive times. Then, the mixture was left standing at room temperature for 5 minutes. Each well that underwent the PCR reaction was placed in a magnet plate and left standing for 2 minutes. In this state where each well that underwent the PCR reaction was placed in a magnet plate, the PCR reaction solution was removed using a pipette so as to avoid contact with magnetic beads contained in the AM Pure XP reagent. 70% ethanol was added at 200 µL per well, and the mixture was left standing for 30 seconds. Ethanol was removed, and the magnetic beads were washed. The above washing step was repeated once again. The washing step was performed with each well placed in the magnet plate. Each well was taken out of the magnet plate, and 20 µL of an elution buffer (purified water, Tris/acetate, pH 8.0, or Tris/EDTA solution) was added to each well. The magnetic beads and the elution buffer were thoroughly mixed by pipetting 10 repetitive times. Each well was placed in a magnet plate and left standing for 1 minute. The elution buffer was recovered with each well placed in the magnet plate, and transferred to another container. In this operation, transfer to a PCR reaction container is preferred for the next step.

—2nd PCR Reaction: Binding of Adaptor Sequence—

PCR reaction was performed in order to add a tag for distinction among the samples for sequencing, and an adaptor sequence for application to sequencing reaction to both ends of the obtained 1st PCR amplification product, to obtain a 2nd PCR reaction product. The composition of the reaction solution was as follows.

[Composition of Reaction Solution]

| | |
|---|---|
| Distilled water | 6.0 µL |
| KAPA HiFi HotStart ReadyMix (2x) | 10.0 µL |
| Primer F for 2nd PCR (10 M) | 1.0 µL |
| Primer R for 2nd PCR (10 µM) | 1.0 µL |
| 1st PCR product | 2.0 µL |
| Total | 20.0 µL |

The 2nd PCR product amplification was performed using Thermal Cycler (apparatus name: T100(TM), manufactured by Bio-Rad Laboratories, Inc.). First, incubation was performed at 95° C. for 3 minutes. Then, 12 temperature cycles each involving 2 steps of 98° C. for 20 seconds and 72° C. for 15 seconds were performed. Finally, incubation was performed at 72° C. for 5 minutes, followed by cooling to 4° C. to terminate the reaction.

—Purification of PCR Product Using Beads—

This step is the same as that performed after the 1st PCR, so that the description is omitted.

—Concentration Measurement of Nucleic Acid Sample—

The 2nd PCR product was quantified using Bioanalyzer 2100 (manufactured by Agilent Technologies, Inc.). The kit used was Agilent DNA7500 kit. Based on the quantification results, the 2nd PCR product was diluted into 10 ng/µL with TE.

—Sequencing Reaction Using Next-Generation Sequencer (NGS)—

The obtained 2nd PCR product was analyzed using a next-generation sequencer (apparatus name: Miseq, manufactured by Illumina, Inc.). The data obtained from the next-generation sequencer was analyzed by sequence processing to obtain information on nucleotide sequences and read numbers. The obtained data is illustrated in Table 7.

TABLE 7

| Fish species | Copy number | Read number |
|---|---|---|
| *Tridentiger brevispinis* | 9259 | 87984 |
| *Cyprinus carpio* | 459 | 4407 |
| *Rhinogobius kurodai* | 292 | 2824 |
| *Opsariichthys platypus* | 241 | 2344 |
| *Tribolodon hakonensis* | 213 | 2074 |
| *Acanthogobius flavimanus* | 191 | 1866 |
| *Plecoglossus altivelis* | 170 | 1666 |
| *Gymnogobius urotaenia* | 135 | 1332 |
| *Hemibarbus barbus* | 103 | 1027 |
| *Mugil cephalus* | 87 | 879 |
| *Micropterus salmoides* | 47 | 496 |
| *Pungtungia herzi* | 27 | 309 |
| *Cobitis* sp. BIWAE type C | 24 | 281 |
| *Pseudogobio esocinus* | 20 | 243 |
| Others | 161 | 1577 |
| Artificial sequence 1 | 1 | 11 |
| Artificial sequence 2 | 10 | 89 |
| Artificial sequence 3 | 50 | 550 |
| Artificial sequence 4 | 100 | 1112 |
| Artificial sequence 5 | 500 | 4778 |

—Generation of Calibration Curve and Quantification—

Figure 27:
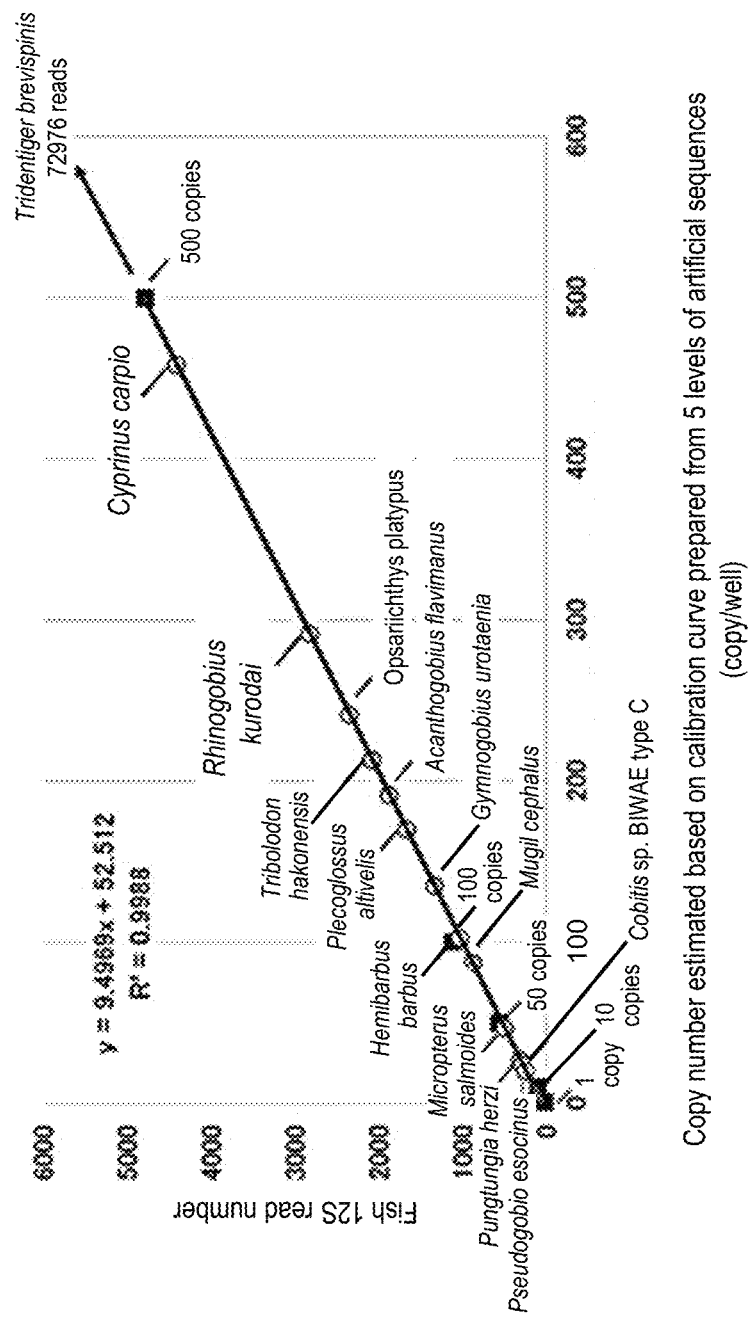
FIG. 27 is a graph illustrating one example of results obtained in Examples.

Based on the results of amplifying the artificial sequences (artificial nucleotide sequences) 1 to 5 of the standard nucleic acids illustrated in Table 7, a calibration curve was generated. The generated calibration curve is illustrated in FIG. 27. In FIG. 27, the ordinate depicts read numbers in Miseq, and the abscissa depicts the numbers of the analyte nucleic acid and the standard nucleic acids (DNA) (copy number/well). The points indicated by square depict the added artificial sequences at 1 copy, 10 copies, 50 copies, 100 copies, and 500 copies, respectively. The calibration curve was generated based on these 5 points (5 levels). The points indicated by circle depict a plot, on the calibration curve, of the read numbers obtained from the standard nucleic acids. As illustrated in FIG. 27, Tridentiger brevispinis was dominant species in the Sagami River and amounted for reads of 70% of the whole samples. The other fish species exhibited reads fewer than 4778 reads, which were the read number of 500 copies, and permitted quantification by interpolation (reliable quantification using the numerical range used in the calibration curve). The copy number of each fish species estimated from the calibration curve is illustrated in Table 7.

Example 4

<Practice of Nucleic Acid Analysis Method—3: Measurement of Fish Fauna Using Environmental DNA>

In Example 4, fish fauna was measured using environmental DNA in the Sagami River. First, water was sampled from the Sagami River and filtered through a filter. DNA was extracted using a DNA extraction kit (trade name: DNeasy Blood & Tissue kit, manufactured by Qiagen N.V.) from the filter used in the filtration. The nucleic acid concentration of the extracted DNA sample (analyte nucleic acid) was quantified using Qubit 3 fluorometer (Invitrogen™).

—1st PCR Reaction—

Using 3 types of fish 12S rRNA sequences (see SEQ ID NOs: 1 to 3) of artificial nucleotide sequences (standard nucleic acids) 1 to 3 designed in Example 1, a well with a nucleic acid copy number of 1 copy (containing 1 yeast cell), a well with a nucleic acid copy number of 5 copies (containing 5 yeast cells), a well with a nucleic acid copy number of 10 copies (containing 10 yeast cells), and a well with a nucleic acid copy number of 50 copies (containing 50 yeast cells) were each prepared. Each well was filled with these 3 types of artificial 12S sequences. Specifically, the well with a nucleic acid copy number of 1 copy contained 1 yeast cell comprising the artificial nucleotide sequence of SEQ ID NO: 1, 1 yeast cell comprising the artificial nucleotide sequence of SEQ ID NO: 2, and 1 yeast cell comprising the artificial nucleotide sequence of SEQ ID NO: 3. The same holds true for the other wells. Then, 5.0 µL of the analyte nucleic acid was filled into each well for sample filling described above. Then, the fish 12S rRNA sequences of the analyte nucleic acid and the artificial 12S sequences were subjected to an amplification reaction by PCR in the same well. The composition of the reaction solution was as follows.

[Composition of Reaction Solution]

| | |
|---|---|
| Distilled water | 1.6 µL |
| KAPA HiFi HotStart ReadyMix (2×) | 12.0 µL |
| Primer F for 1st PCR (10 µM) | 0.7 µL |
| Primer R for 1st PCR (10 µM) | 0.7 µL |
| Sagami River-derived environmental DNA extract (sample) | 5.0 µL |
| Yeast DNA (containing artificial nucleotide sequences 1 to 3 and 0.4 U Zymolyase(R)) | 4.0 µL |
| Total | 24.0 µL |

The primers for 1st PCR were MiFish-U (see Non-Patent Document 1) having an added sequence for an annealing reaction of primers for 2nd PCR.

The nucleic acid amplification was performed by PCR using T100™ Thermal Cycler (Bio-Rad Laboratories, Inc.). First, incubation was performed at 95° C. for 3 minutes. Then, 35 temperature cycles each involving 3 steps of 98° C. for 20 seconds, 65° C. for 15 seconds, and 72° C. for 15 seconds were performed. Finally, incubation was performed at 72° C. for 5 minutes, followed by cooling to 4° C. to terminate the reaction.

—2nd PCR Reaction: Binding of Adaptor Sequence—

PCR reaction was performed in order to add a tag for distinction among the samples for sequencing, and an adaptor sequence for application to a sequencing reaction to both ends of the obtained 1st PCR amplification product, to obtain a 2nd PCR reaction product. The composition of the reaction solution was as follows.

[Composition of Reaction Solution]

| | |
|---|---|
| Distilled water | 6.0 µL |
| KAPA HiFi HotStart ReadyMix (2×) | 10.0 µL |
| Primer F for 2nd PCR (10 M) | 1.0 µL |
| Primer R for 2nd PCR (10 µM) | 1.0 µL |
| 1st PCR product | 2.0 µL |
| Total | 20.0 µL |

The nucleic acid amplification was performed by PCR using T100™ Thermal Cycler (Bio-Rad Laboratories, Inc.). First, incubation was performed at 95° C. for 3 minutes. Then, 12 temperature cycles each involving 2 steps of 98° C. for 20 seconds and 72° C. for 15 seconds were performed. Finally, incubation was performed at 72° C. for 5 minutes, followed by cooling to 4° C. to terminate the reaction.

—Purification of PCR Product by Agarose Gel Electrophoresis—

Electrophoresis was performed at 100 V for 20 minutes using a 2% agarose gel. A band observed at 330 to 400 bp was excised, and the PCR product was purified using FastGene Gel/PCR Extraction Kit (Nippon Genetics Co., Ltd.).

—Concentration Measurement of Nucleic Acid Sample—

The 2nd PCR product was quantified using Bioanalyzer 2100 (manufactured by Agilent Technologies, Inc.). The kit used was Agilent DNA7500 kit. Based on the quantification results, the 2nd PCR product was diluted into 10 ng/µL with TE. The diluted 2nd PCR products obtained from four wells were mixed into the same reaction solution.

—Sequencing Reaction Using Next-Generation Sequencer (NGS)—

The obtained 2nd PCR product was analyzed using a next-generation sequencer (apparatus name: Miseq, manufactured by Illumina, Inc.). The data obtained from the next-generation sequencer was analyzed by sequence processing to obtain information on nucleotide sequences and read numbers. The obtained data is illustrated in Table 8. The numerical values in the table denote read numbers.

TABLE 8

| | | 1 (copy/well) | 5 (copy/well) | 10 (copy/well) | 50 (copy/well) |
|---|---|---|---|---|---|
| Sample | Artificial nucleotide sequence 1 (SEQ ID NO: 1) | 383 | 1668 | 4022 | 16728 |
| | Artificial nucleotide sequence 2 (SEQ ID NO: 2) | 848 | 1268 | 2681 | 14558 |
| | Artificial nucleotide sequence 3 (SEQ ID NO: 3) | 421 | 1932 | 2299 | 15934 |
| | Tribolodon hakonensis | 26731 | 25728 | 12750 | 15232 |
| | Carassius cuvieri | 12099 | 9115 | 5681 | 4859 |
| | Opsariichthys platypus | 6027 | 4993 | 2245 | 2221 |
| | Mugil cephalus | 1237 | 927 | 728 | 307 |
| | Micropterus salmoides | 850 | 788 | 372 | 589 |
| | Tridentiger brevispinis | 457 | 388 | 1227 | 188 |
| | Channa argus | 542 | 1000 | 0 | 113 |
| | Gymnogobius urotaenia | 984 | 106 | 237 | 14 |
| | Pseudorasbora parva | 0 | 654 | 550 | 63 |
| | Odontobutis obscura | 801 | 1 | 213 | 0 |
| | Rhynchocypris lagowskii steindachneri | 367 | 580 | 0 | 0 |
| | Squalidus chankaensis biwae | 246 | 279 | 59 | 351 |
| | Nipponocypris sp. | 203 | 86 | 54 | 434 |
| | Others | 1893 | 566 | 741 | 884 |

—Normalization of Read—

Data normalized with the sum of reads other than the reads of the artificial 12S sequence as 100,000 reads is illustrated in Table 9. The numerical values in the table denote read numbers. A mean and a coefficient of variation (CV) calculated for the artificial 12S sequences 1, 2, and 3 are illustrated in Table 10. The accuracy management of analysis can be appropriately carried out using the mean and the coefficient of variation (CV) in Table 10.

TABLE 9

| Sample | | 1 (copy/well) | 5 (copy/well) | 10 (copy/well) | 50 (copy/well) |
|---|---|---|---|---|---|
| Sample | Artificial nucleotide sequence 1 (SEQ ID NO: 1) | 730.4 | 3689.4 | 16180.6 | 66236.4 |
| | Artificial nucleotide sequence 2 (SEQ ID NO: 2) | 1617.2 | 2804.6 | 10785.7 | 57644 |
| | Artificial nucleotide sequence 3 (SEQ ID NO: 3) | 802.9 | 4273.3 | 9248.9 | 63092.5 |
| | Tribolodon hakonensis | 50977.4 | 56906.5 | 51293.4 | 60312.8 |
| | Carassius cuvieri | 23073.4 | 20161 | 22854.7 | 19239.8 |
| | Opsariichthys platypus | 11493.8 | 11043.8 | 9031.7 | 8794.3 |
| | Mugil cephalus | 2359 | 2050.4 | 2928.8 | 1215.6 |
| | Micropterus salmoides | 1621 | 1742.9 | 1496.6 | 2332.2 |
| | Tridentiger brevispinis | 871.5 | 858.2 | 4936.2 | 744.4 |
| | Channa argus | 1033.6 | 2211.9 | 0 | 447.4 |
| | Gymnogobius urotaenia | 1876.5 | 234.5 | 953.5 | 55.4 |
| | Pseudorasbora parva | 0 | 1446.6 | 2212.7 | 249.5 |
| | Odontobutis obscura | 1527.5 | 2.2 | 856.9 | 0 |
| | Rhynchocypris lagowskii steindachneri | 699.9 | 1282.9 | 0 | 0 |
| | Squalidus chankaensis biwae | 469.1 | 617.1 | 237.4 | 1389.8 |
| | Nipponocypris sp. | 387.1 | 190.2 | 217.2 | 1718.5 |
| | Others | 3610 | 1251.9 | 2981.1 | 3500.3 |

TABLE 10

| | 1 (copy/well) | 5 (copy/well) | 10 (copy/well) | 50 (copy/well) |
|---|---|---|---|---|
| Artificial nucleotide sequence 1 | 730.4 | 3689.4 | 16180.6 | 66236.4 |
| Artificial nucleotide sequence 2 | 1617.2 | 2804.6 | 10785.7 | 57644 |
| Artificial nucleotide sequence 3 | 802.9 | 4273.3 | 9248.9 | 63092.5 |
| Mean | 1050.1 | 3589.1 | 12071.7 | 62324.3 |
| CV | 46.90% | 20.60% | 30.20% | 7.00% |

Figure 29:
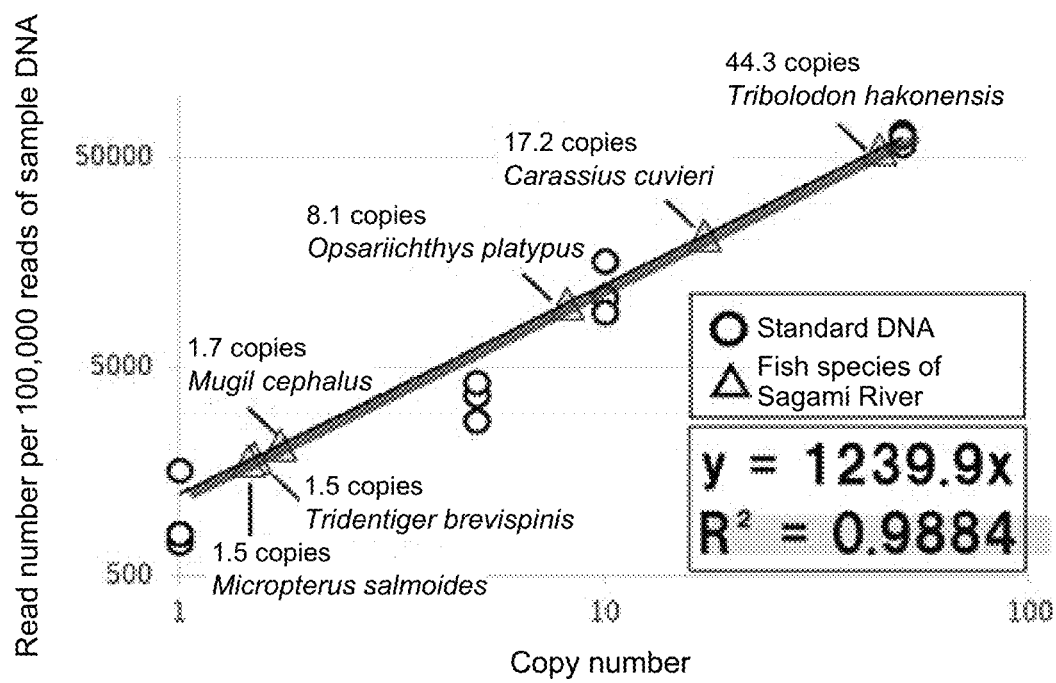
FIG. 29 is a graph illustrating an alternative example of results obtained in Examples (calibration curve of samples from the Sagami River).

Based on the read numbers of the artificial 12S sequences 1, 2, and 3 in Table 9, a relational expression between a copy number (x) and an output read number (y) was drawn to obtain the expression y=1239.9x (coefficient of determination, $R^2$=0.9884). The copy number of each fish species was estimated according to this expression to obtain Table 12. The numerical values in the table denote copy numbers. The accuracy management of analysis can be appropriately carried out using the obtained coefficient of determination, $R^2$, of the calibration curve. The generated calibration curve is illustrated in FIG. 29. The fish species illustrated in FIG. 29 employed an average of four wells, and fish species estimated to have 1 copy or less were excluded for the sake of convenience. The read number and copy number of each fish species used in the generation of FIG. 29 is illustrated in Table 11 for reference.

TABLE 11

| | Name | Read number | Copy number (copy/well) |
|---|---|---|---|
| Sample | Tribolodon hakonensis | 54872.5 | 44.3 |
| | Carassius cuvieri | 21332.2 | 17.2 |
| | Opsariichthys platypus | 10090.9 | 8.1 |
| | Mugil cephalus | 2138.4 | 1.7 |

TABLE 11-continued

| | Name | Read number | Copy number (copy/well) |
|---|---|---|---|
| | Micropterus salmoides | 1798.2 | 1.5 |
| | Tridentiger brevispinis | 1852.6 | 1.5 |

TABLE 12

| Sample | | 1 (copy/well) | 5 (copy/well) | 10 (copy/well) | 50 (copy/well) |
|---|---|---|---|---|---|
| Sample | Artificial nucleotide sequence 1 (SEQ ID NO: 1) | 0.6 | 3 | 13 | 53.4 |
| | Artificial nucleotide sequence 2 (SEQ ID NO: 2) | 1.3 | 2.3 | 8.7 | 46.5 |
| | Artificial nucleotide sequence 3 (SEQ ID NO: 3) | 0.6 | 3.4 | 7.5 | 50.9 |
| | Tribolodon hakonensis | 41.1 | 45.9 | 41.4 | 48.6 |
| | Carassius cuvieri | 18.6 | 16.3 | 18.4 | 15.5 |
| | Opsariichthys platypus | 9.3 | 8.9 | 7.3 | 7.1 |
| | Mugil cephalus | 1.9 | 1.7 | 2.4 | 1 |
| | Micropterus salmoides | 1.3 | 1.4 | 1.2 | 1.9 |
| | Tridentiger brevispinis | 0.7 | 0.7 | 4 | 0.6 |
| | Channa argus | 0.8 | 1.8 | 0 | 0.4 |
| | Gymnogobius urotaenia | 1.5 | 0.2 | 0.8 | 0 |
| | Pseudorasbora parva | 0 | 1.2 | 1.8 | 0.2 |
| | Odontobutis obscura | 1.2 | 0 | 0.7 | 0 |
| | Rhynchocypris lagowskii steindachneri | 0.6 | 1 | 0 | 0 |
| | Squalidus chankaensis biwae | 0.4 | 0.5 | 0.2 | 1.1 |
| | Nipponocypris sp. | 0.3 | 0.2 | 0.2 | 1.4 |
| | Others | 2.9 | 1 | 2.4 | 2.8 |

Example 5

<Practice of Nucleic Acid Analysis Method—4: Measurement of Flora Using Microbial Mixed DNA Sample>

In Example 5, flora was measured using a microbial mixed DNA sample (ZymoBIOMICS Microbial Community DNA Standard (manufactured by Zymo Research Corp.)).

In Example 3, the artificial nucleotide sequences 1 to 5 of the standard nucleic acids were disposed in the same wells as those containing a nucleic acid sample as the analyte nucleic acid. By contrast, in Example 5, nucleic acids having the artificial nucleotide sequences of the standard nucleic acids DNA600-G were disposed in different wells, and amplification results thereabout were combined to generate a calibration curve.

—Preparation of Analyte Nucleic Acid (Nucleic Acid Sample)—

Wells were filled with the DNA600-G-containing yeast prepared in Example 1 in the same way as in Example 1. The yeast was dispensed to 4 different wells at 4 levels of 1 cell (1 copy), 5 cells (5 copies), 10 cells (10 copies), and 50 cells (50 copies), respectively. Next, 2.0 µL (0.5 pg/µL) of the microbial mixed DNA sample was manually filled into each well containing the nucleic acid having the artificial nucleotide sequence of DNA600-G. Then, the microbial mixed DNA sample and the DNA600-G in the wells were subjected to an amplification reaction by PCR in the same well. The composition of the reaction solution was as follows.

[Composition of Reaction Solution]

| | |
|---|---|
| Distilled water | 6.3 μL |
| 10 × Ex Taq buffer | 2.0 μL |
| dNTP (2.5 mM) | 1.6 μL |
| Primer F for 1st PCR for microbial 16S amplification (10 μM) | 1.0 μL |
| Primer R for 1st PCR for microbial 16S amplification (10 μM) | 1.0 μL |
| Primer F for 1st PCR for 600G amplification (10 μM) | 1.0 μL |
| Primer R for 1st PCR for 600G amplification (10 μM) | 1.0 μL |
| Analyte nucleic acid (microbial mixed DNA sample) | 2.0 μL |
| Ex Taq (5 units/μL) | 0.1 μL |
| Standard nucleic acid (containing DNA600-G and 0.4 U Zymolyase) | 4.0 μL |
| Total | 20.0 μL |

The analyte nucleic acid (microbial mixed DNA sample) and the standard nucleic acid (DNA600-G; artificial sequence 6) were amplified by PCR using Thermal Cycler (apparatus name: T100™, manufactured by Bio-Rad Laboratories, Inc.). First, incubation was performed at 94° C. for 2 minutes. Then, 23 temperature cycles each involving 3 steps of 94° C. for 30 seconds, 50° C. for 30 seconds, and 72° C. for 30 seconds were performed. Finally, incubation was performed at 72° C. for 5 minutes, followed by cooling to 4° C. to terminate the reaction.

—Purification of PCR Product Using Beads—

The PCR product was purified using AMPure XP reagent (Beckman Coulter, Inc.). First, the AMPure XP reagent was left standing at room temperature for 30 minutes or longer before use. The AMPure XP reagent was mixed by inversion for 1 minute or longer. Then, 20 μL of the AMPure XP reagent was added to each well that underwent the PCR reaction. The PCR reaction solution and the AMPure XP reagent were thoroughly mixed by pipetting 10 repetitive times. Then, the mixture was left standing at room temperature for 5 minutes. Each well that underwent the PCR reaction was placed in a magnet plate and left standing for 2 minutes. In this state where each well that underwent the PCR reaction was placed in a magnet plate, the PCR reaction solution was removed using a pipette so as to avoid contact with magnetic beads contained in the AM Pure XP reagent. 70% ethanol was added at 200 μL per well, and the mixture was left standing for 30 seconds. Ethanol was removed, and the magnetic beads were washed. The washing step was repeated once again. The washing step was performed with each well placed in the magnet plate. Each well was taken out of the magnet plate, and 20 μL of an elution buffer (purified water, Tris/acetate, pH 8.0, or Tris/EDTA solution) was added to each well. The magnetic beads and the elution buffer were thoroughly mixed by pipetting 10 repetitive times. Each well was placed in a magnet plate and left standing for 1 minute. The elution buffer was recovered with each well placed in the magnet plate, and transferred to another container. In this operation, transfer to a PCR reaction container is preferred for the next step.

—2nd PCR Reaction: Binding of Adaptor Sequence—

PCR reaction was performed in order to add a tag for distinction among the samples for sequencing, and an adaptor sequence for application to a sequencing reaction to both ends of the obtained 1st PCR amplification product, to obtain a 2nd PCR reaction product. The composition of the reaction solution was as follows.

[Composition of Reaction Solution]

| | |
|---|---|
| Distilled water | 10.3 μL |
| 10 × Ex Taq buffer | 2.0 μL |
| dNTP (2.5 mM) | 1.6 μL |
| Primer F for 2nd PCR (10 M) | 1.0 μL |
| Primer R for 2nd PCR (10 μM) | 1.0 μL |
| 1st PCR product | 4.0 μL |
| Ex Taq (5 units/μL) | 0.1 μL |
| Total | 20.0 μL |

The 2nd PCR product amplification was performed using Thermal Cycler (apparatus name: T100™, manufactured by Bio-Rad Laboratories, Inc.). First, incubation was performed at 94° C. for 2 minutes. Then, 8 temperature cycles each involving 3 steps of 94° C. for 30 seconds, 50° C. for 30 seconds, and 72° C. for 30 seconds were performed. Finally, incubation was performed at 72° C. for 5 minutes, followed by cooling to 4° C. to terminate the reaction.

—Purification of PCR Product Using Beads—

This step is the same as that performed after the 1st PCR, so that the description is omitted.

—Concentration Measurement of Nucleic Acid Sample—

The 2nd PCR product was quantified using Bioanalyzer 2100 (manufactured by Agilent Technologies, Inc.). The kit used was Agilent DNA7500 kit. Based on the quantification results, the 2nd PCR product was diluted into 10 ng/μL with TE. The diluted solutions of the 2nd PCR products obtained from 4 wells were mixed into the same reaction solution.

—Sequencing Reaction Using Next-Generation Sequencer (NGS)—

The 2nd PCR product was analyzed using a next-generation sequencer (apparatus name: Miseq, manufactured by Illumina, Inc.). The data obtained from the next-generation sequencer was analyzed by sequence processing to obtain information on nucleotide sequences and read numbers. The data was normalized with the read number obtained as 1,000,000 reads. The sum of the normalized reads of 4 samples is illustrated in Table 13.

TABLE 13

| Species name | Copy number | Read number |
|---|---|---|
| Bacillus subtilis | 48.7 | 91045 |
| Listeria monocytogenes | 28.8 | 53773 |
| Staphylococcus aureus | 29.4 | 55010 |
| Enterococcus faecalis | 21.8 | 40772 |
| Lactobacillus fermentum | 16.7 | 31208 |
| Salmonella enterica | 23.1 | 43099 |
| Escherichia coli | 17.9 | 33426 |
| Pseudomonas aeruginosa | 8.3 | 15583 |
| Others | 1879.1 | 3510155 |
| Artificial sequence 6 | 1 | 2867 |
| Artificial sequence 6 | 5 | 8990 |
| Artificial sequence 6 | 10 | 21155 |
| Artificial seauence 6 | 50 | 92919 |

—Generation of Calibration Curve and Quantification—

Figure 28:
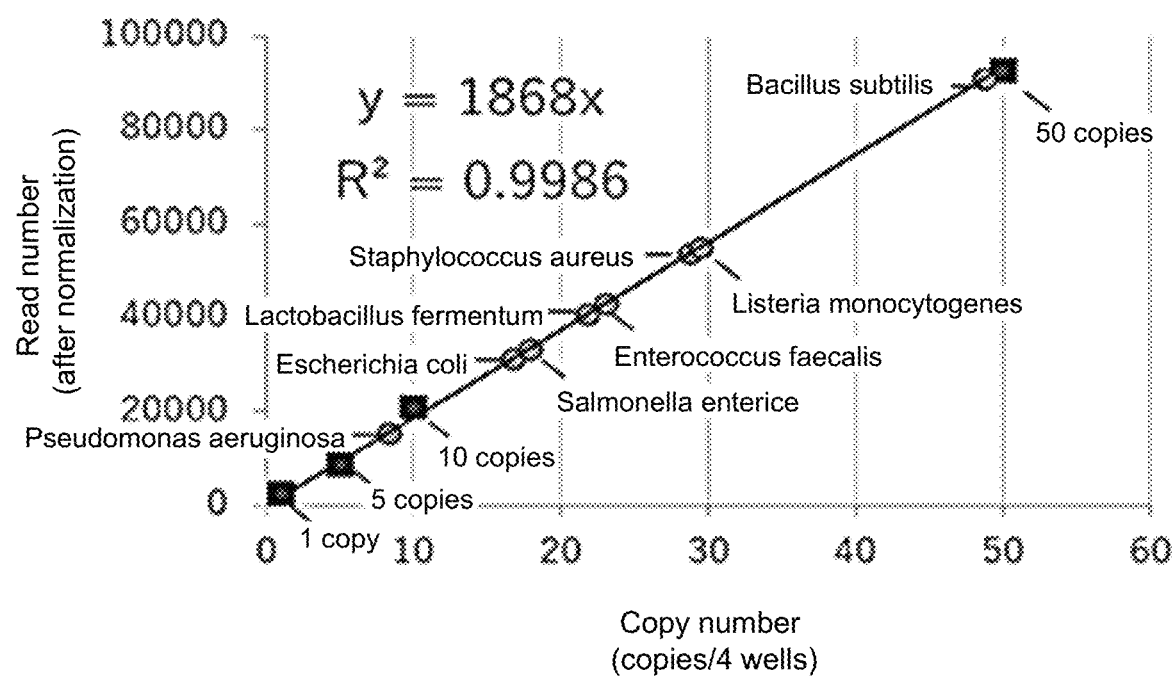
FIG. 28 is a graph illustrating another example of results obtained in Examples.

Based on the results of amplifying the standard nucleic acid DNA600-G (artificial sequence 6) illustrated in Table 13, a calibration curve was generated. The generated calibration curve is illustrated in FIG. 28. In FIG. 28, the ordinate depicts read numbers obtained by adding 4-well read numbers normalized with 1,000,000 reads per well obtained as read numbers in Miseq, and the abscissa depicts DNA numbers (copy number/4 wells). The points indicated by square depict the artificial sequences added to the wells at 1 copy, 5 copies, 10 copies, and 50 copies, respectively.

The calibration curve was drawn based on these 4 points (4 levels). The points indicated by circle depict a plot, on the calibration curve, of the reads obtained from the nucleic acid sample based on the normalized read numbers. Eight types of microbes contained in the microbial mixed DNA sample (analyte nucleic acid) exhibited reads fewer than 92919 reads, which were the read number of 50 copies, and permitted quantification by interpolation (reliable quantification using the numerical range used in the calibration curve). The copy number of each microbe estimated from the calibration curve is illustrated in Table 13.

Example 6

Removing Ghost Read in Sequencing Reaction Using NGS—1

In Example 6, flora was measured using a microbial mixed DNA sample (ZymoBIOMICS Microbial Community DNA Standard (Zymo Research Corp.)).
1st PCR Reaction
Wells for sample filling were filled with the DNA600-G-containing yeast by the same procedures as in Example 1. In this operation, a well with a nucleic acid copy number of 1 copy (containing 1 yeast cell), and a well with a nucleic acid copy number of 10 copies (containing 10 yeast cells) were each prepared. The microbial mixed DNA sample was filled at 2.0 μL per well to the wells for sample filling. In this operation, 0.5 pg/μL of the microbial mixed DNA sample was added to the well with 1 copy of the nucleic acid, and 5 pg/μL of the microbial mixed DNA sample was added to the well with 10 copies of the nucleic acid. Specifically, a well containing 10 pg of the mixed DNA sample and 10 copies of DNA600-G, and a well containing 1 pg of the mixed DNA sample and 1 copy of DNA600-G were each prepared.

Then, the microbial mixed DNA sample and the DNA600-G were subjected to an amplification reaction by PCR in the same well. The composition of the reaction solution was 20 μL in total consisting of 6.3 μL of distilled water, 2.0 μL of 10×Ex Taq buffer, 1.6 μL of dNTP (2.5 mM), 1.0 μL of primer F for 1st PCR for microbial 16S amplification (SEQ ID NO: 9, 10 μM), 1.0 μL of primer R for 1st PCR for microbial 16S amplification (SEQ ID NO: 10, 10 μM), 1.0 μL of primer F for 1st PCR for DNA600-G amplification (SEQ ID NO: 11, 10 μM), 1.0 μL of primer F for 1st PCR for DNA600-G amplification (SEQ ID NO: 12, 10 μM), 2.0 μL of the microbial mixed DNA sample, 0.1 μL of Ex Taq (5 units/pp, and 4.0 μL of yeast DNA containing DNA600-G (containing 0.4 U Zymolyase).

The subsequent nucleic acid amplification, purification of a PCR product using beads, and 2nd PCR reaction followed Example 5 except that the following primers were used in the 2nd PCR reaction: F-1 (SEQ ID NO: 13), F-2 (SEQ ID NO: 14), F-3 (SEQ ID NO: 15), F-4 (SEQ ID NO: 16), F-5 (SEQ ID NO: 17), F-6 (SEQ ID NO: 18), F-7 (SEQ ID NO: 19), F-8 (SEQ ID NO: 20), R-1 (SEQ ID NO: 21), and R-2 (SEQ ID NO: 22).

The subsequent nucleic acid amplification, concentration measurement of the nucleic acid sample, and sequencing reaction using NGS followed Example 5.
<Threshold Setting with Reference to Read Number of Specific Copy Number, and Analysis>
The obtained reads were summarized in Table 14 (reads that seemed to be obviously derived from contamination were excluded in advance from the reads).

TABLE 14

| Microbe name | Raw data | After ghost removal |
|---|---|---|
| Bacillus subtilis | 25631 | 25631 |
| Listeria monocytogenes | 30523 | 30523 |
| Staphylococcus aureus | 24574 | 24574 |
| Enterococcus faecalis | 16067 | 16067 |
| Lactobacillus fermentum | 15169 | 15169 |
| Salmonella enterica | 14534 | 14534 |
| Escherichia coli | 14411 | 14411 |
| Pseudomonas aeruginosa | 7580 | 7580 |
| Acinetobacter | 643 | 0 |
| Bacillus firmus | 1014 | 0 |
| DNA600-G | 1574 | 0 |
| Others | 953 | 0 |

Table 14 shows raw data as well as data obtained by removing sequence data equal to or less than the read number of DNA600-G from the raw data (after removing ghost). The removing ghost means that a read that is derived from various error sources and is unnecessary for analysis is removed.

Figure 30:
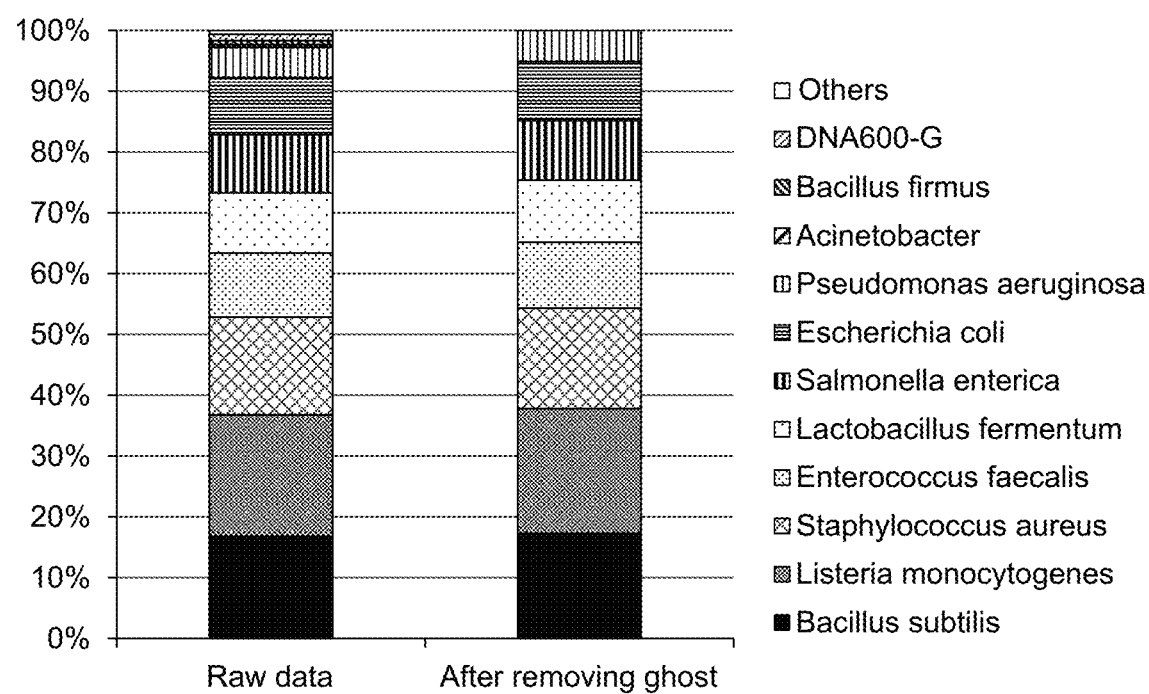
FIG. 30 shows the percentages of sequences of reads obtained with NGS in Example 6.

The raw data also comprised a large number of sequences other than those derived from 8 types of microbes (in Table 14, *Bacillus subtilis* through *Pseudomonas aeruginosa*) contained in the microbial mixed DNA sample. However, when excluding sequences having read numbers equal to or less than that of 10 copies of DNA600-G, the reads of two types of microbes, *Acinetobacter* and *Bacillus firmus*, and the reads of "Others" were removed. A stacked bar graph of the percentages of the sequences is illustrated in FIG. 30.

The reads of "Others" were also removed with reference to the read number of 1 copy of DNA600-G (data not shown). Two types of microbes, *Acinetobacter* and *Bacillus firmus*, had a read number at the similar level as that of DNA600-G. Therefore, their reads were able to be removed when the read number of DNA600-G was multiplied by 2.0 to 3.0 as a coefficient (data not shown).

Example 7

Removing Ghost Read in Sequencing Reaction Using NGS—2

In Example 7, NGS analysis was conducted using DNA samples extracted from fish muscle tissues.
DNA Extraction Reaction
Muscle tissues of 3 species, *Pagrus major, Oncorhynchus mykiss*, and *Sardinops melanostictus*, were prepared as the fish muscle tissues, and DNA was extracted therefrom using DNeasy Blood & Tissue Kit (Qiagen N.V.).
1st PCR Reaction
Wells for sample filling were filled with the yeasts containing artificial 12S sequences by the same procedures as in Example 1. The artificial 12S sequences were artificial nucleotide sequences (see SEQ ID NOs: 1 to 5) of nucleic acids that were synthesized so as to have nucleotide sequences capable of binding to primers MiFish-U (see M. Miya et al., 2015, R. Soc. Open Sci., 22: 2 (7); manufacturer name: FASMAC Corp.; see SEQ ID NOs: 7 and 8) at both ends of a 130-bp nucleotide sequence having a GC content ratio of approximately 50%, not forming a higher-order structure at 60° C., and not having a repeat sequence. Since the artificial nucleotide sequences have nucleotide sequences capable of binding to the primers MiFish-U at both ends, the standard nucleic acids and an analyte nucleic acid can be analyzed using primers having the same nucleotide sequences when fish 12S rRNA contained in the analyte nucleic acid is analyzed. For filling, a well with a nucleic acid copy number of 1 copy (containing 1 yeast cell), a well with a nucleic acid copy number of 5 copies (containing 5 yeast cells), a well with a nucleic acid copy number of 10 copies (containing 10 yeast cells), and a well with a nucleic acid copy number of 50 copies (containing 50 yeast cells) were each prepared. Each well was filled with these 3 types of yeasts comprising artificial 12S sequences. Specifically, the well with a nucleic acid copy number of 1 copy contained 1 yeast cell comprising the artificial nucleotide sequence of SEQ ID NO: 1, 1 yeast cell comprising the artificial nucleotide sequence of SEQ ID NO: 2, and 1 yeast cell comprising the artificial nucleotide sequence of SEQ ID NO: 3. The same holds true for the other wells. Then, 5.0 µL of the fish muscle tissue-derived DNA sample was filled into each well for sample filling described above.

The subsequent nucleic acid amplification, purification of a PCR product using beads, and 2nd PCR reaction followed Example 5 except that the following primers were used in the 2nd PCR reaction: F-1 (SEQ ID NO: 13), F-2 (SEQ ID NO: 14), F-3 (SEQ ID NO: 15), F-4 (SEQ ID NO: 16), F-5 (SEQ ID NO: 17), F-6 (SEQ ID NO: 18), F-7 (SEQ ID NO: 19), F-8 (SEQ ID NO: 20), R-1 (SEQ ID NO: 21), and R-2 (SEQ ID NO: 22).

The subsequent nucleic acid amplification, concentration measurement of the nucleic acid sample, and sequencing reaction using NGS followed Example 5 except that purification of a PCR product by agarose gel electrophoresis was performed according to Example 4 after the nucleic acid amplification and before the concentration measurement of the nucleic acid sample.

<Threshold Setting with Reference to Read Number of Specific Copy Number, and Analysis>

The obtained reads were summarized in Table 15.

TABLE 15

| Subject | 1 copy | 5 copies | 10 copies | 50 copies |
|---|---|---|---|---|
| Pagrus major | 27431 | 26441 | 26526 | 26309 |
| Oncorhynchus mykiss | 15525 | 15111 | 15547 | 14748 |
| Sardinops melanostictus | 2006 | 1349 | 1583 | 1390 |
| Carassius cuvieri | 1 | 0 | 0 | 0 |
| Seriola quinqueradiata | 3 | 1 | 1 | 1 |
| Phellodendron amurense | 0 | 0 | 0 | 5 |
| Pagrus auriga | 0 | 2 | 0 | 2 |
| Pagrus major | 1 | 1 | 1 | 0 |
| Sequence 15 | 18 | 131 | 98 | 624 |
| Sequence 16 | 69 | 61 | 61 | 636 |
| Sequence 17 | 10 | 72 | 50 | 768 |

The raw data also comprised a large number of sequences other than those derived from 3 types of fish species (*Pagrus major*, *Oncorhynchus mykiss*, and *Sardinops melanostictus*) contained in the fish muscle tissue-derived DNA samples. However, their read numbers were equal to or less than that of 1 copy of the artificial DNA. These were assessed as ghost reads and were able to be removed.

Example 8

Removing Ghost Read in Sequencing Reaction Using NGS—3

In Example 8, fish fauna was measured using environmental DNA in the Sagami River. First, water was sampled from the Sagami River and filtered through a filter. The filter used in the filtration was chopped, and DNA was extracted using a DNA extraction kit (DNeasy Blood & Tissue kit, manufactured by Qiagen N.V.). The nucleic acid concentration of the extracted DNA sample (analyte nucleic acid) was quantified using Qubit 4 fluorometer (Invitrogen™).

The subsequent procedures followed Example 6 to obtain information on sequences and read numbers from the water sample from the Sagami River.

<Threshold Setting with Reference to Read Number of Specific Copy Number, and Analysis>

The obtained reads were summarized in Table 16.

TABLE 16

| Subject | 1 copy | After ghost removal |
|---|---|---|
| Tribolodon hakonensis | 26731 | 26731 |
| Carassius cuvieri | 12099 | 12099 |
| Opsariichthys platypus | 6027 | 6027 |
| Mugil cephalus | 1237 | 1237 |
| Micropterus salmoides | 850 | 850 |
| Tridentiger brevispinis | 457 | 0 |
| Channa argus | 542 | 0 |
| Gymnogobius urotaenia | 984 | 984 |
| Odontobutis obscura | 801 | 801 |
| Rhynchocypris lagowskii steindachneri | 367 | 0 |
| Squalidus chankaensis biwae | 246 | 0 |
| Nipponocypris sp. | 203 | 0 |
| Others | 1893 | 0 |
| Sequence 15 | 383 | 0 |
| Sequence 16 | 848 | 0 |
| Sequence 17 | 421 | 0 |

From the sequences derived from the fish species illustrated in Table 16, sequences having a read number equal to or less than the average read number (550.7 reads) of 1 copy of the artificial DNA were able to be excluded.

Data normalized with the sum of reads other than the reads of the artificial 12S sequence as 100,000 reads is illustrated in Table 17. A read number that fell below the average read number (1050 reads) of 1 copy of the artificial DNA was indicated in boldface type.

TABLE 17

| Subject | 1 copy | 5 copies | 10 copies | 50 copies |
|---|---|---|---|---|
| Tribolodon hakonensis | 50977.4 | 56906.5 | 51293.4 | 60312.8 |
| Carassius cuvieri | 23073.4 | 20161.0 | 22854.7 | 19239.8 |
| Opsariichthys platypus | 11493.8 | 11043.8 | 9031.7 | 8794.3 |
| Mugil cephalus | 2359.0 | 2050.4 | 2928.8 | 1215.6 |
| Micropterus salmoides | 1621.0 | 1742.9 | 1496.6 | 2332.2 |
| Tridentiger brevispinis | 871.5 | 858.2 | 4936.2 | 744.4 |
| Channa argus | 1033.6 | 2211.9 | 0 | 447.4 |
| Gymnogobius urotaenia | 1876.5 | 234.5 | 953.5 | 55.4 |
| Pseudorasbora parva | 0 | 1446.6 | 2212.7 | 249.5 |
| Odontobutis obscura | 1527.5 | 2.2 | 856.9 | 0 |
| Rhynchocypris lagowskii steindachneri | 699.9 | 1282.9 | 0 | 0 |
| Squalidus chankaensis biwae | 469.1 | 617.1 | 237.4 | 1389.8 |
| Nipponocypris sp. | 387.1 | 190.2 | 217.2 | 1718.5 |
| Others | 3610.0 | 1251.9 | 2981.1 | 3500.3 |
| Sequence 15 | 730.4 | 3689.4 | 16180.6 | 66236.4 |
| Sequence 16 | 1617.2 | 2804.6 | 10785.7 | 57644.0 |
| Sequence 17 | 802.9 | 4273.3 | 9248.9 | 63092.5 |

Based on the read numbers of the sequences 15, 16, and 17 in Table 17, a relational expression between a copy number (x) and an output read number (y) was drawn to obtain the expression y=1223.9x (coefficient of determination, $R^2$=0.9884). The copy number of each fish species was estimated according to this expression to obtain Table 18. An estimated copy number of less than 1 copy was indicated in boldface type.

TABLE 18

| Subject | 1 copy | 5 copies | 10 copies | 50 copies |
|---|---|---|---|---|
| *Tribolodon hakonensis* | 41.1 | 45.9 | 41.4 | 48.6 |
| *Carassius cuvieri* | 18.6 | 16.3 | 18.4 | 15.5 |
| *Opsariichthys platypus* | 9.3 | 8.9 | 7.3 | 7.1 |
| *Mugil cephalus* | 1.9 | 1.7 | 2.4 | 1.0 |
| *Micropterus salmoides* | 1.3 | 1.4 | 1.2 | 1.9 |
| *Tridentiger brevispinis* | 0.7 | 0.7 | 4.0 | 0.6 |
| *Channa argus* | 0.8 | 1.8 | 0.0 | 0.4 |
| *Gymnogobius urotaenia* | 1.5 | 0.2 | 0.8 | 0.0 |
| *Pseudorasbora parva* | 0.0 | 1.2 | 1.8 | 0.2 |
| *Odontobutis obscura* | 1.2 | 0.0 | 0.7 | 0.0 |
| *Rhynchocypris lagowskii steindachneri* | 0.6 | 1.0 | 0.0 | 0.0 |
| *Squalidus chankaensis biwae* | 0.4 | 0.5 | 0.2 | 1.1 |
| *Nipponocypris* sp. | 0.3 | 0.2 | 0.2 | 1.4 |
| Others | 2.9 | 1.0 | 2.4 | 2.8 |
| Sequence 15 | 0.6 | 3.0 | 13.0 | 53.4 |
| Sequence 16 | 1.3 | 2.3 | 8.7 | 46.5 |
| Sequence 17 | 0.6 | 3.4 | 7.5 | 50.9 |

As mentioned above, the method of the present invention was illustrated to be able to exclude sequences derived from various error sources according to a clear criterion.

For example, aspects of the present invention include the followings:

<1> A method for analyzing at least one nucleic acid, comprising:

a library preparation step of preparing a library comprising at least one standard nucleic acid of specific copy number(s) and at least one analyte nucleic acid in a same system;

a calibration curve data generation step of generating calibration curve data based on the copy number(s) of the at least one standard nucleic acid of specific copy number(s); and an analyte nucleic acid analysis step of identifying at least one nucleotide sequence of the analyte nucleic acid while identifying the number(s) of the at least one nucleotide sequence of the at least one analyte nucleic acid using the calibration curve data.

<2> The method for analyzing at least one nucleic acid according to <1>, wherein the at least one standard nucleic acid comprises the standard nucleic acids having different nucleotide sequences of specific copy numbers different from each other in a same system.

<3> The method for analyzing at least one nucleic acid according to <1> or <2>, wherein the at least one standard nucleic acid comprises the standard nucleic acids having different nucleotide sequences of specific copy numbers different from each other in two or more different systems, and the obtained calibration curve data from the at least one standard nucleic acid is normalized and combined.

<4> The method for analyzing at least one nucleic acid according to any of <1> to <3>, wherein the at least one standard nucleic acid comprises DNA.

<5> The method for analyzing at least one nucleic acid according to any of <1> to <4>, wherein the at least one analyte nucleic acid comprises at least any one of DNA and cDNA.

<6> The method for analyzing at least one nucleic acid according to any of <1> to <5>, wherein the preparing a library is performed using same primers for the at least one standard nucleic acid and the at least one analyte nucleic acid.

<7> The method for analyzing at least one nucleic acid according to any of <1> to <5>, wherein the preparing the library is performed using different primers for the at least one standard nucleic acid and the at least one analyte nucleic acid.

<8> A program for analyzing at least one nucleic acid, which allows a computer to execute the processes of:

with respect to a library comprising at least one standard nucleic acid of specific copy number(s) and at least one analyte nucleic acid prepared in a same system, generating calibration curve data on the at least one standard nucleic acid by a calibration curve data generating unit based on data on the at least one standard nucleic acid of specific copy number(s); and identifying nucleotide sequence(s) of the at least one analyte nucleic acid while identifying the number of the nucleotide sequence(s) of the at least one analyte nucleic acid using the calibration curve data, by an analyte nucleic acid analyzing unit.

<9> A device for library preparation for use in the method for analyzing at least one nucleic acid according to any of <1> to <7> or the method according to any of <1'> to <10'> below, the device having at least one standard nucleic acid of specific copy number(s).

<10> The device for library preparation according to <9>, wherein the at least one standard nucleic acid satisfies the expression $CV<1/\sqrt{x}$ which is represented by a coefficient of variation (CV value) obtained dividing uncertainty of the specific copy number(s) by a mean of specific copy numbers, and mean x of specific copy numbers of the at least one standard nucleic acid.

<11> The device for library preparation according to <9> or <10>, wherein the at least one standard nucleic acid of the specific copy number(s) is disposed by an inkjet mode.

The method for analyzing at least one nucleic acid according to any of <1> to <7>, the program for analyzing at least one nucleic acid according to <8>, and the device for library preparation according to any of <9> to <11> may solve the conventional problems described above and attain the object of the present invention.

The present invention also encompasses, but is not limited to, the following embodiments.

<1'> A method for analyzing data of high-throughput sequencing reaction using at least one standard sample comprising a nucleic acid of specific copy number(s), the method comprising: a) preparing a library for the at least one standard sample and at least one sequence sample under a same condition; b) subjecting the library prepared in the step a) to a sequencing reaction to obtain output data comprising reads derived from the at least one standard sample and the at least one sequence sample; and c) dividing the reads in the output data, based on a threshold determined with reference to read number(s) derived from the at least one standard sample in the output data, into at least one read equal to or less than the threshold and at least one read equal to or more than the threshold.

<2'> The method according to <1'>, wherein the preparing the library from the at least one standard sample and the at least one sequence sample in the step a) is performed in a same reaction system.

<3'> The method according to <1'> or <2'>, wherein the at least one nucleic acid comprises DNA.

<4'> The method according to any of <1'> to <3'>, wherein the threshold is obtained by multiplying read number(s) derived from the at least one standard sample obtained in the step b) by a predetermined coefficient.

<5'> The method according to any of <1'> to <4'>, wherein a plurality of standard samples comprising the nucleic acids of the same or different specific copy numbers are used in the step a), and the method further comprises selecting a standard sample to determine the threshold in the step c).

<6'> The method according to any of <1'> to <5'>, wherein the same sequence sample is analyzed using a plurality of wells, and a plurality of standard samples comprising the nucleic acids of the same or different specific copy numbers are used in the step a), and data is normalized among the plurality of wells, and the determined threshold is applied to the plurality of wells for analysis in the step c).

<7'> The method according to <6'>, wherein the method comprises drawing a relational expression of the specific copy number(s) and the output read number(s) based on the data normalized among the plurality of standard samples to estimate copy number(s) from the output read number(s) using an inverse function of the relational expression; and determining the threshold with reference to the estimated copy number(s).

<8'> The method according to any of <1'> to <7'>, wherein a plurality of standard samples comprising the nucleic acids of the same specific copy number are used in the step a), and the threshold is determined based on a mean or a median of read numbers of the plurality of standard samples in the step c).

<9'> The method according to any of <1'> to <8'>, wherein the specific copy number is 200 copies or less.

<10'> The method according to <9'>, wherein the specific copy number is 10 copies or less.

<11'> The method according to any of <1'> to <10'>, wherein the read equal to or less than the threshold in the output data is excluded, and data analysis is conducted on the read equal to or more than the threshold in the step c).

<12'> A kit for performing a method according to any of <1'> to <11'> or <1> to <7>.

<13'> A program for allowing a computer to perform a method according to any of <1'> to <11'> or <1> to <7>.

DESCRIPTION OF THE REFERENCE NUMERAL

1: Device
2: Base material
3: Well
4: Nucleic acid
5: Closing component

CITATION LIST

Patent Document 1: JP Patent Publication (Kokai) No. 2015-204813
Patent Document 2: JP Patent Publication (Kohyo) No. 2018-514207
Non-Patent Document 1: MiFish, a set of universal PCR primers for metabarcoding environmental DNA from fishes: detection of more than 230 subtropical marine species. M. Miya, et al., 2015

All publications, patents and patent applications cited herein are incorporated herein by reference in their entirety.
[Sequence Listing]

What is claimed is:

1. A method for analyzing data of high-throughput sequencing reaction using at least one standard sample comprising a nucleic acid of specific copy number(s), the method comprising:
   a) preparing a library for the at least one standard sample and at least one sequence sample under a same condition, wherein the library is prepared with a base material that comprises a plurality of filled sites and is formed by
       discharging one or more cell suspension liquid droplets into at least one of a first set of filled sites, a cell of the cell suspension having the nucleic acid of the at least one standard sample, wherein each of the at least one of the first set of filled sites having the one or more cell suspension liquid droplets discharged therein has a specific copy number of the nucleic acid of the at least one standard sample;
       counting a number of cells in the one or more cell suspension liquid droplets after discharging of the liquid droplets into the at least one of the first set of filled sites;
       filling a sample comprising a nucleic acid of the at least one sequence sample into at least one of a second set of filled sites;
       extracting the nucleic acid from the cell of the cell suspension in each of the at least one of the first set of filled sites and, optionally, extracting the at least one sequence sample, wherein a coefficient of variation (CV), which is the standard deviation of the specific copy number divided by an average copy number x, satisfies $CV < 1/\sqrt{x}$ for the average copy number;
   b) subjecting the library prepared in the step a) to a sequencing reaction to obtain output data comprising reads derived from the at least one standard sample and the at least one sequence sample; and
   c) separating the reads in the output data into a first group of reads having at least one read less than at least one threshold and a second group having at least one read more than the at least one threshold, wherein if the reads in the output data are equal to the at least one threshold, they are optionally included in the first group or the second group, wherein the at least one threshold is selected from the group consisting of a read number, the read number multiplied by a predetermined coefficient, the mean or median of read numbers, and a normalized value thereof.

2. The method according to claim 1, wherein the preparing the library for the at least one standard sample and the at least one sequence sample in the step a) is performed in a same reaction system.

3. The method according to claim 1, wherein the at least one nucleic acid comprises DNA.

4. The method according to claim 1, wherein the at least one threshold is obtained by multiplying read number(s) derived from the at least one standard sample obtained in the step h) by the predetermined coefficient.

5. The method according to claim 1, wherein a plurality of standard samples comprising nucleic acids of the same or different specific copy numbers are used in the step a), and the method further comprises selecting a standard sample to determine the at least one threshold in the step c).

6. The method according to claim 1,
   wherein the same sequence sample is analyzed using a plurality of filled sites, and a plurality of standard samples comprising nucleic acids of the same or different specific copy numbers are used in the step a), and data is normalized among the plurality of filled sites, and the at least one threshold is applied to the plurality of filled sites for analysis in the step c).

7. The method according to claim 6, wherein the method comprises drawing a relational expression of the specific copy number(s) and the output read number(s) based on the data normalized among the plurality of standard samples to estimate copy number(s) from the output read number(s) using an inverse function of the relational expression; and determining the at least one threshold with reference to the estimated copy number(s).

8. The method according to claim 1, wherein a plurality of standard samples comprising nucleic acids of the same specific copy number are used in the step a), and the at least one threshold is determined based on a mean or a median of read numbers of the plurality of standard samples in the step c).

9. The method according to claim 1, wherein the specific copy number is 200 copies or less.

10. The method according to claim 9, wherein the specific copy number is 10 copies or less.

11. The method according to claim 1, wherein data from the first group is excluded, and data analysis is conducted on the data from the second group.

\* \* \* \* \*